(12) United States Patent
Patel et al.

(10) Patent No.: US 11,707,467 B2
(45) Date of Patent: Jul. 25, 2023

(54) (17-ß)-3-OXOANDROST-4-EN-17YL TRIDECANOATE COMPOSITIONS AND METHODS OF THEIR PREPARATION AND USE

(71) Applicant: Lipocine Inc., Salt Lake City, UT (US)

(72) Inventors: Mahesh V. Patel, Salt Lake City, UT (US); Nachiappan Chidambaram, Sandy, UT (US); Satish Kumar Nachaegari, Salt Lake City, UT (US); Srinivasan Venkateshwaran, Salt Lake City, UT (US); Joel Frank, Sandy, UT (US); Amy Jo Portlock, Riverton, UT (US)

( * ) Notice: Subject to any disclaimer, the term of this patent is extended or adjusted under 35 U.S.C. 154(b) by 0 days.

(21) Appl. No.: 16/367,091

(22) Filed: Mar. 27, 2019

(65) Prior Publication Data

US 2019/0350943 A1  Nov. 21, 2019

Related U.S. Application Data

(63) Continuation of application No. 15/507,754, filed as application No. PCT/US2015/047579 on Aug. 28, 2015, now abandoned.

(60) Provisional application No. 62/043,343, filed on Aug. 28, 2014.

(51) Int. Cl.
*A61K 31/5685* (2006.01)
*C07J 1/00* (2006.01)

(52) U.S. Cl.
CPC ......... *A61K 31/5685* (2013.01); *C07J 1/0025* (2013.01)

(58) Field of Classification Search
CPC .. C12Q 1/6804; C12Q 1/6806; C12Q 1/6809; C12Q 1/6844; C12Q 1/6883; C12Q 2600/154; A61K 31/5685; C07J 1/0025
USPC ...................................................... 514/182
See application file for complete search history.

(56) References Cited

U.S. PATENT DOCUMENTS

| | | |
|---|---|---|
| 2,680,749 A | 6/1954 | Cawley et al. |
| 2,742,487 A | 4/1956 | Robledano |
| 3,097,139 A | 7/1963 | Thorp |
| 3,097,144 A | 7/1963 | Banker |
| 3,164,520 A | 1/1965 | Huber |
| 3,266,991 A | 8/1966 | Wettstein et al. |
| 3,510,561 A | 5/1970 | Koh |
| 4,098,802 A | 7/1978 | van der Vies |
| 4,147,783 A * | 4/1979 | van der Vies .......... A61K 9/14 514/171 |
| 4,156,719 A | 5/1979 | Sezaki et al. |
| 4,177,188 A | 12/1979 | Hansen et al. |
| 4,196,188 A | 4/1980 | Besins |
| 4,220,599 A | 9/1980 | van der Vies |
| 4,239,754 A | 12/1980 | Sache et al. |
| 4,388,307 A | 6/1983 | Cavanak |
| 4,439,432 A | 3/1984 | Peat |
| 4,572,915 A | 2/1986 | Crooks |
| 4,579,730 A | 4/1986 | Kidron et al. |
| 4,628,052 A | 12/1986 | Peat |
| 4,628,098 A | 12/1986 | Nohara et al. |
| 4,654,327 A | 3/1987 | Teng |
| 4,656,161 A | 4/1987 | Herr |
| 4,658,944 A | 4/1987 | Kogure et al. |
| 4,689,333 A | 8/1987 | Nohara et al. |
| 4,695,450 A | 9/1987 | Bauer |
| 4,703,042 A | 10/1987 | Bodor |
| 4,713,246 A | 12/1987 | Begum et al. |
| 4,717,569 A | 1/1988 | Harrison et al. |
| 4,717,596 A | 1/1988 | Barbee et al. |
| 4,719,239 A | 1/1988 | Muller et al. |
| 4,727,109 A | 2/1988 | Schmidt et al. |
| 4,731,384 A | 3/1988 | Dell |
| 4,795,327 A | 1/1989 | Gaylord et al. |
| 4,832,952 A | 5/1989 | Hersh et al. |
| 4,834,965 A | 5/1989 | Martani et al. |
| 4,849,227 A | 7/1989 | Cho |
| 4,867,984 A | 9/1989 | Patel |
| 4,874,795 A | 10/1989 | Yesair |
| 4,880,634 A | 11/1989 | Speiser |
| 4,895,726 A | 1/1990 | Curtet et al. |
| 4,897,269 A | 1/1990 | Mezei |
| 4,900,734 A | 2/1990 | Maxson et al. |
| 4,925,672 A | 5/1990 | Gremm |
| 4,944,949 A | 7/1990 | Story |
| 4,961,890 A | 10/1990 | Boyer |
| 4,963,540 A | 10/1990 | Maxson et al. |
| 4,994,439 A | 2/1991 | Longenecker et al. |
| 5,014,656 A | 5/1991 | Leptich et al. |
| 5,023,108 A | 6/1991 | Bageria et al. |
| 5,026,560 A | 6/1991 | Makino et al. |

(Continued)

FOREIGN PATENT DOCUMENTS

| | | |
|---|---|---|
| CA | 2295028 | 1/1999 |
| CA | 2302735 | 1/2000 |

(Continued)

OTHER PUBLICATIONS

LGC Purity of Testosterone Undecanoate, pp. 1-6, 99.5% purity. Release date May 28, 2015.*
Pfeil et al.; "Current and Future Testosterone Delivery Systems for Treatment of the Hypogonadal Male;" Expert Opinion on Drug Delivery; (Apr. 2008); pp. 471-481; vol. 5, No. 4; <doi: 10.1517/17425247.5343471>.
Baert et al.; "Analytical, biopharmaceutical and regulatory evaluation of topical testosterone preparations"; European Journal of Pharmaceutics and Biopharmaceutics; May 2009; p. 275-281; vol. 72(1).
Gonzalo-Lumbrerars et al.; "HPLC method development for testosterone propionate and cipionate in oil-based injectables"; J. Pharm. Biomed. Anal.; Jul. 15, 2005; p. 757-762; vol. 38(4).
Pozo et al.; "Quantification of testosterone undecanoate in human hair by liquid chromatography-tandem mass spectrometry"; Biomed. Chrom.; Aug. 2009; p. 873-880; vol. 23(8).

(Continued)

*Primary Examiner* — Umamaheswari Ramachandran
(74) *Attorney, Agent, or Firm* — Michael R. Schramm

(57) ABSTRACT

Described here are substantially pure (17-β)-3-Oxoandrost-4-en-17-yl tridecanoate compositions, methods of their preparation and uses thereof.

16 Claims, 29 Drawing Sheets

(56) References Cited

U.S. PATENT DOCUMENTS

| | | |
|---|---|---|
| 5,035,891 A | 7/1991 | Runkel et al. |
| 5,045,321 A | 9/1991 | Makino et al. |
| 5,057,319 A | 10/1991 | Gottwald et al. |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |
| 5,120,710 A | 6/1992 | Liedtke |
| 5,140,021 A | 8/1992 | Maxon et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Geyer et al. |
| 5,384,133 A | 1/1995 | Boyes et al. |
| 5,389,382 A | 2/1995 | List et al. |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | DeBoeck et al. |
| 5,560,931 A | 10/1996 | Eickhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wright |
| 5,633,015 A | 5/1997 | Gillis et al. |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savatano et al. |
| 5,686,105 A | 11/1997 | Keim et al. |
| 5,688,761 A | 11/1997 | Owen et al. |
| 5,698,155 A | 12/1997 | Grosswald et al. |
| 5,698,217 A * | 12/1997 | Wilking ................ A61K 9/703 424/448 |
| 5,707,648 A | 1/1998 | Yiv |
| 5,717,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,916,589 A | 6/1999 | Hauer et al. |
| 5,922,355 A | 7/1999 | Parikh et al. |
| 5,948,773 A | 9/1999 | Akiyama et al. |
| 5,948,825 A | 9/1999 | Takahshi et al. |
| 5,962,014 A | 10/1999 | Hauer et al. |
| 5,962,017 A | 10/1999 | Hauer et al. |
| 5,965,161 A | 10/1999 | Oshlack |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kerc et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamm et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |
| 6,228,400 B1 | 5/2001 | Lee et al. |
| 6,248,363 B1 | 6/2001 | Patel et al. |
| 6,255,100 B1 | 7/2001 | Ko et al. |
| 6,267,985 B1 | 7/2001 | Chen et al. |
| 6,287,594 B1 | 9/2001 | Wilson |
| 6,294,192 B1 | 9/2001 | Patel et al. |
| 6,296,876 B1 | 10/2001 | Odidi et al. |
| 6,299,904 B1 | 10/2001 | Shimizu et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder et al. |
| 6,328,994 B1 | 12/2001 | Shimizu et al. |
| 6,340,471 B1 | 1/2002 | Kershman et al. |
| 6,342,246 B2 | 1/2002 | Johnson et al. |
| 6,361,796 B1 | 3/2002 | Rudnic et al. |
| 6,368,634 B1 | 4/2002 | Remon |
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambhul et al. |
| 6,444,225 B1 | 9/2002 | Sherman |
| 6,447,806 B1 | 9/2002 | Gassmann et al. |
| 6,451,339 B2 | 9/2002 | Patel et al. |

(56) References Cited

U.S. PATENT DOCUMENTS

| | | |
|---|---|---|
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |
| 6,468,559 B1 | 10/2002 | Chen et al. |
| 6,475,519 B1 | 11/2002 | Minzer et al. |
| 6,503,894 B1 | 1/2003 | Dudley et al. |
| 6,531,139 B1 | 3/2003 | Gao et al. |
| 6,569,463 B2 | 5/2003 | Patel et al. |
| 6,589,552 B2 | 7/2003 | Stamm et al. |
| 6,589,562 B1 | 7/2003 | Shefer et al. |
| 6,623,755 B2 | 9/2003 | Chen et al. |
| 6,630,134 B1 | 10/2003 | Klein |
| 6,652,880 B1 | 11/2003 | Aylwin et al. |
| 6,665,880 B2 | 11/2003 | Pope |
| 6,660,286 B1 | 12/2003 | Lambert et al. |
| 6,667,048 B1 | 12/2003 | Lambert et al. |
| 6,692,766 B1 | 2/2004 | Rubinstein et al. |
| 6,696,482 B2 | 2/2004 | Schemoy et al. |
| 6,720,001 B2 | 4/2004 | Chen et al. |
| 6,737,082 B1 | 5/2004 | Darder |
| 6,761,903 B2 | 7/2004 | Chen et al. |
| 6,881,745 B2 | 4/2005 | Hayes et al. |
| 6,887,493 B2 | 5/2005 | Shefer et al. |
| 6,923,988 B2 | 5/2005 | Patel et al. |
| 6,913,244 B1 | 7/2005 | Atkinson et al. |
| 6,977,083 B1 | 12/2005 | Huebler et al. |
| 6,982,281 B1 | 1/2006 | Chen et al. |
| 7,025,979 B2 | 4/2006 | Neischlag et al. |
| 7,138,389 B2 | 11/2006 | Amory et al. |
| 7,374,779 B2 | 5/2008 | Chen et al. |
| 7,658,944 B2 | 2/2010 | Holm et al. |
| 7,718,640 B2 | 5/2010 | Hubler et al. |
| 8,241,664 B2 | 4/2012 | Dudley et al. |
| 8,338,395 B2 | 12/2012 | Hubler et al. |
| 8,492,369 B2 | 7/2013 | Dudley et al. |
| 8,778,922 B2 | 7/2014 | Giliyar et al. |
| 8,828,428 B1* | 9/2014 | Dudley .................. A61P 15/00 424/456 |
| 8,865,695 B2 | 10/2014 | Giliyar et al. |
| 9,034,858 B2 | 5/2015 | Giliyar et al. |
| 9,205,057 B2 | 12/2015 | Giliyar et al. |
| 9,358,241 B2 | 6/2016 | Giliyar |
| 9,480,690 B2 | 11/2016 | Giliyar et al. |
| 9,498,485 B2* | 11/2016 | Patel .................... A61K 31/568 |
| 9,757,389 B2* | 9/2017 | Patel .................... A61K 31/568 |
| 2001/0018069 A1 | 8/2001 | Johnson et al. |
| 2002/0006443 A1 | 1/2002 | Curatolo et al. |
| 2002/0013304 A1 | 1/2002 | Wilson et al. |
| 2002/0058066 A1 | 5/2002 | Tomohira et al. |
| 2002/0068693 A1 | 6/2002 | Jeng et al. |
| 2002/0102301 A1 | 8/2002 | Schwarz |
| 2002/0103139 A1 | 8/2002 | Weisspapir et al. |
| 2002/0183296 A1 | 12/2002 | Dudley |
| 2003/0022875 A1 | 1/2003 | Wilson et al. |
| 2003/0072798 A1 | 4/2003 | Schwarz et al. |
| 2003/0077297 A1 | 4/2003 | Chen et al. |
| 2003/0082215 A1 | 5/2003 | Lemut et al. |
| 2003/0104048 A1 | 6/2003 | Patel et al. |
| 2003/0180352 A1 | 9/2003 | Patel et al. |
| 2003/0181431 A1 | 9/2003 | Hodgen |
| 2003/0186892 A1 | 10/2003 | Taneja |
| 2003/0228358 A1 | 12/2003 | Perlman et al. |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0002482 A1 | 1/2004 | Dudley et al. |
| 2004/0048896 A1 | 3/2004 | Phillips |
| 2004/0127476 A1 | 7/2004 | Kershaman et al. |
| 2005/0031693 A1 | 2/2005 | Babcock et al. |
| 2005/0032762 A1* | 2/2005 | Hubler ................. A61K 31/565 424/731 |
| 2005/0070516 A1 | 3/2005 | Wilson |
| 2005/0080075 A1 | 4/2005 | Nichols et al. |
| 2005/0096296 A1 | 5/2005 | Fikstad et al. |
| 2005/0096365 A1 | 5/2005 | Fikstad et al. |
| 2005/0100608 A1 | 5/2005 | Ebert |
| 2005/0101517 A1 | 5/2005 | De Nijs et al. |
| 2005/0171193 A1 | 8/2005 | Chen et al. |
| 2005/0176692 A1 | 8/2005 | Amory et al. |
| 2005/0209345 A1 | 9/2005 | Charman |
| 2005/0220825 A1 | 10/2005 | Funke et al. |
| 2005/0269251 A1 | 12/2005 | Cork |
| 2005/0287203 A1 | 12/2005 | De Nijs et al. |
| 2005/0287212 A1 | 12/2005 | Dong et al. |
| 2006/0003002 A1 | 1/2006 | Fikstad et al. |
| 2006/0034937 A1 | 2/2006 | Patel |
| 2006/0051406 A1 | 3/2006 | Parmar |
| 2006/0106004 A1 | 5/2006 | Brody et al. |
| 2006/0142257 A1 | 6/2006 | Nieschlag |
| 2007/0110777 A1 | 5/2007 | Joabsson et al. |
| 2007/0134336 A1 | 6/2007 | Worle et al. |
| 2007/0154533 A1 | 7/2007 | Dudley |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2008/0317859 A1 | 12/2008 | Sournac et al. |
| 2009/0074859 A1 | 3/2009 | Patel |
| 2010/0136105 A1 | 6/2010 | Chen et al. |
| 2010/0137271 A1 | 6/2010 | Chen et al. |
| 2010/0148675 A1 | 6/2010 | Meijer et al. |
| 2010/0173882 A1 | 7/2010 | Giliyar et al. |
| 2010/0266645 A1 | 10/2010 | Liang et al. |
| 2011/0039814 A1 | 2/2011 | Huatan et al. |
| 2011/0142945 A1 | 6/2011 | Chen et al. |
| 2011/0251167 A1 | 10/2011 | Dudley et al. |
| 2011/0263552 A1 | 10/2011 | Dhindra et al. |
| 2012/0135074 A1 | 5/2012 | Chandrashekar |
| 2012/0148675 A1 | 6/2012 | Chickmath et al. |
| 2012/0244215 A1 | 9/2012 | Giliyar et al. |
| 2012/0322780 A1 | 12/2012 | Giliyar et al. |
| 2013/0022674 A1 | 1/2013 | Dudley et al. |
| 2013/0052263 A1 | 2/2013 | Fikstad et al. |
| 2013/0225544 A1* | 8/2013 | Nachaegari .......... A61K 9/4866 514/178 |
| 2014/0288039 A1* | 9/2014 | Nachaegari .......... A61K 9/4858 514/178 |
| 2014/0303130 A1 | 10/2014 | Giliyar et al. |
| 2014/0303132 A1* | 10/2014 | Nachaegari .......... A61K 31/568 514/181 |
| 2014/0323452 A1 | 10/2014 | Nachaegari et al. |
| 2014/0323453 A1 | 10/2014 | Nachaegari et al. |
| 2015/0038475 A1 | 2/2015 | Chickmath et al. |
| 2015/0224059 A1 | 8/2015 | Giliyar |
| 2015/0273067 A1 | 10/2015 | Patel |
| 2016/0074416 A1 | 3/2016 | Giliyar et al. |

FOREIGN PATENT DOCUMENTS

| | | |
|---|---|---|
| CN | 101217963 A | 7/2008 |
| DE | 10108614 | 9/2002 |
| EP | 0036145 | 5/1985 |
| EP | 0184942 | 6/1986 |
| EP | 0537070 | 4/1993 |
| EP | 0981328 | 3/2000 |
| EP | 0988858 | 3/2000 |
| EP | 0724877 | 6/2000 |
| EP | 1103252 | 5/2001 |
| EP | 0904064 | 10/2001 |
| EP | 1624855 | 12/2004 |
| EP | 1879456 | 1/2008 |
| EP | 2000130 | 12/2008 |
| EP | 2558073 A1 | 10/2011 |
| FR | 2647346 | 11/1990 |
| FR | 2758459 | 7/1998 |
| GB | 1264677 | 2/1973 |
| GB | 2098865 | 12/1982 |
| GB | 2228198 | 8/1990 |
| JP | S52-66616 | 6/1977 |
| JP | S57-70824 | 5/1982 |
| JP | 01139526 | 6/1989 |
| JP | 5194209 | 8/1993 |

(56) References Cited

FOREIGN PATENT DOCUMENTS

| | | |
|---|---|---|
| JP | 07041422 | 2/1995 |
| JP | H07-508724 | 9/1995 |
| JP | 09241152 | 9/1997 |
| JP | 11049664 | 2/1999 |
| JP | 11152227 | 6/1999 |
| JP | 2001500368 | 1/2001 |
| JP | 2001508445 | 6/2001 |
| JP | 2001514626 | 9/2001 |
| JP | 2002510311 | 4/2002 |
| JP | 2002520377 | 7/2002 |
| JP | 2003500368 | 1/2003 |
| JP | 2008540451 | 11/2008 |
| WO | WO 82/01649 | 5/1982 |
| WO | WO 84/02076 | 6/1984 |
| WO | WO 88/00059 | 1/1988 |
| WO | WO 92/18147 | 10/1992 |
| WO | WO 93/02664 | 2/1993 |
| WO | WO 93/06921 | 4/1993 |
| WO | WO 93/25192 | 12/1993 |
| WO | WO 94/25068 | 11/1994 |
| WO | WO 95/01785 | 1/1995 |
| WO | WO 95/01786 | 1/1995 |
| WO | WO 95/24893 | 9/1995 |
| WO | WO 95/34287 | 12/1995 |
| WO | WO 96/17597 | 6/1996 |
| WO | WO 97/04749 | 2/1997 |
| WO | WO 94/08610 | 4/1997 |
| WO | WO 97/40823 | 11/1997 |
| WO | WO 97/48382 | 12/1997 |
| WO | WO 98/00116 | 1/1998 |
| WO | WO 98/30205 | 7/1998 |
| WO | WO 98/33512 | 8/1998 |
| WO | WO 98/38984 | 9/1998 |
| WO | WO 98/50077 | 11/1998 |
| WO | WO 98/56357 | 12/1998 |
| WO | WO 99/00111 | 1/1999 |
| WO | WO 99/29300 | 6/1999 |
| WO | WO 99/40904 | 8/1999 |
| WO | WO 99/44584 | 9/1999 |
| WO | WO 99/48498 | 9/1999 |
| WO | WO 00/003753 | 1/2000 |
| WO | WO 00/016749 | 3/2000 |
| WO | WO 00/025772 | 5/2000 |
| WO | WO 00/037057 | 6/2000 |
| WO | WO 00/050007 | 8/2000 |
| WO | WO 00/057859 | 10/2000 |
| WO | WO 00/057918 | 10/2000 |
| WO | WO 00/059482 | 10/2000 |
| WO | WO 00/059512 | 10/2000 |
| WO | WO 00/076482 | 10/2000 |
| WO | WO 00/071163 | 11/2000 |
| WO | WO 00/072825 | 12/2000 |
| WO | WO 01/001960 | 1/2001 |
| WO | WO 01/012155 | 2/2001 |
| WO | WO 01/021154 | 3/2001 |
| WO | WO 01/028555 | 4/2001 |
| WO | WO 01/049262 | 7/2001 |
| WO | WO 01/037808 | 5/2002 |
| WO | WO 02/039983 | 5/2002 |
| WO | WO 03/068186 | 8/2003 |
| WO | WO 2004/087052 | 10/2004 |
| WO | WO 2004/105694 | 12/2004 |
| WO | WO 2005/041929 | 5/2005 |
| WO | WO 2006/013369 | 2/2006 |
| WO | WO 2006/113505 | 10/2006 |
| WO | WO 2006/119498 | 11/2006 |
| WO | WO 2007/018943 | 2/2007 |
| WO | WO 2007/100614 A2 | 9/2007 |
| WO | WO 2010/081032 | 7/2010 |
| WO | WO 2010/102737 | 9/2010 |
| WO | WO 2011/082384 | 7/2011 |
| WO | WO 2011/129812 A1 | 10/2011 |
| WO | WO 2012/075081 | 7/2012 |

OTHER PUBLICATIONS

Webster et al.; "Validation of Pharmaceutical Potency Determinations by Quantitative Nuclear Magnetic Resonance Spectrometry"; Appl Spectrosc.; May 2010; p. 537-542; vol. 64(5).

Bugay; "Characterization of the solid-state: spectroscopic techniques"; Adv Drug Deliv Rev.; May 16, 2001; p. 43-65; vol. 48(1).

Blystone et al.; "Toxicity and carcinogenicity of androstenedione in F344/N rats and B6C3F2 mice"; Food Chem Toxicol; Sep. 2011; p. 2116-2124; doi: 10.1016/j.fct.2011.05.026.EpubMay 30, 2011.

Tarumi et al.; "Andriostenedione induces abnormalities in morphology and function of developing oocytes, which impairs oocyte meiotic competence"; Fertil Steril.; Feb. 2012; p. 469-476; vol. 97(2); doi: 10.1016/j.fertnstert.2011.11.040.

A.T. Burbello et al., Sovremennye lekarstvennyesredstava S-Pb "Neva," 2004, p. 567.

Addo et al.; Non Polar Extracts of Serum From Males Contain Covert Radioimmunoassayable Testosterone; Steroids; (Sep. 1989); p. 257-269; vol. 54(3).

Alvarez et al.; "The Role of Calcium Ions and Bile Salts on the Pancreatic Lipase-Catalyzed Hydrolysis of Triglyceride Emulsions Stabilized with Lecithin"; Pharmaceutical Research, (1989); p. 449-457; vol. 6(6).

Andriol® Testocaps™; Consumer Medicine Information; (Sep. 2003).

Androderm® Product Label and Medication Guide; 1995; Labeler—Watson Pharma, Inc.; Revised Nov. 2013; 23 pages.

Androgel® Product Label and Medication Guide; May 2013; Labeler—AbbVie Inc.; Revised Oct. 2013; 28 pages.

Atkinson et al.; Long Term Experience with Testosterone Replacement Through Scrotal Skin; Testosterone: Action, Deficiency and Substitution; Nieschlag, E. and Behre, HM, Eds.; 1998; pp. 365-388.

Aungst; "Intestinal Permeation Enhancers," Journal of Pharmaceutical Sciences; (2000); p. 429-442; vol. 89(4).

Bagchus et al.; "Important Effect of Food on the Bioavailability of Oral Testosterone Undecanoate"; Pharmacotherapy (2003); p. 319-325; vol. 23(3).

Baluom et al.; "The Importance of Intestinal Residence Time of Absorption Enhancer on Drug Implication on Formulative Considerations"; International Journal of Pharmaceutics; (1998); p. 21-30; vol. 176.

Bates et al.; "Bioavailability of Micronized Griseofulvin from Corn Oil-in-Water Emulsion, Aqueous Suspension, and Commercial Tablet Dosage Forms in Humans"; Journal of Pharmaceutical Sciences; (1975); p. 793-797; vol. 64(5).

Beatch et al.; "Ventricular Fibrillation, an Uncontrolled Arrhythmia Seeking New Targets"; Drug Dev. Res; (2002); p. 45-52; vol. 55.

Bernkop-Schnurch; "The Use of Inhibitory Agents to Overcome the Enzymatic Barrier to Perorally Administered Therapeutic Peptides and Proteins"; Journal of Controlled Release; p. 1-16; vol. 52.

Bhargava et al., Using Microemulsions for Drug Delivery; Pharmaceutical Technology; (Mar. 1987); p. 46-53.

Cantrill; Which Testosterone Replacement Therapy; Clinical Endocrinol; (1984); p. 97-107; vol. 21.

Charman et al.; "Physicochemical and Physiological Mechanisms for the Effects of Food on Drug Absorption: The Role of Lipids and pH"; Journal of Pharmaceutical Sciences; (1997); p. 269-282; vol. 86(3).

Constantidides; Lipid Microemulsion for Improving Drug Dissolution and Oral Absorption: Physical and Biopharmaceutical Aspect; Pharmaceutical Research; (1995); p. 1561-1572; vol. 12(11).

Depo-Testosterone® Product Label and Medication Guide; Sep. 2006; Labeler—Pharmacia & Upjohn Company; Revised Aug. 2013; 12 pages.

Emulsion; IUPAC Compendim of Chemical Terminology, $2^{nd}$ Ed., 1997.

Frey et al.; Bioavailability of Oral Testosterone in Males; Eur. J. Pharmacol.; (1979); p. 345-349; vol. 16.

Gennaro; Surfactant Properties in Solution and Micelle Fromation, Colloidal Dispersions; Remington's Pharmaceutical Sciences; (1985); p. 293-300; Chapter 20.

(56) References Cited

OTHER PUBLICATIONS

Goncharova et al.; "Preparation of Testosterone Esters"; Pharmaceutical Chemistry Journal; (Jul. 1973); p. 427-428; vol. 7(7).
Gooren, LJG "A ten year safety study of the oral androgen testosterone undecanoate." J. Androl., 1994; p. 212-215; vol. 15.
Graham-Smith et al., "The Oxford Reference-book in clinical Pharmacoloty and Pharmacotherapy," M. Meditsina Publishers, 2000, pp. 25, 136-137 (incl. Eng version).
Healthlink; What are the symptoms of Hypogonadism?; [retrieved from on-line website (http://www.healthline.com/health/hypogonadism#Overview 1), last visit on Apr. 14, 2015]. 1 page.
Hong, B.S., et al., Recent trends in the treatment of testosterone deficiency syndrome. International Journal of Urology, (2007) 14; 981-985.
Horter et al.; "Influence of Physiochemical Properties on Dissolution of Drugs in the Gastrointestinal Tract"; Advanced Drug Delivery Reviews; (1997); p. 3-14; vol. 25.
Houwing et al.; "Pharmacokinetic Study in Women of Three Different Doses of a New Formulation of Oral Testosterone Undecanoate, Andriol Testocaps", Pharmacotherapy; (2003); p. 1257-1265; vol. 23(10).
Humberstone et al.; "Lipid-based Vehicles for the Oral Delivery of Poorly Water Soluble Drugs"; Advanced Drug Delivery Reviews; (1997) p. 103-128.
Hutchison; "Digestable Emulsions and Microemulsions for Optimum Oral Delivery of Hydrophobic Drugs"; Bulletin Technique Gattefosse; (1994); p. 67-74; vol. 87.
Javanbakht et al; Pharmacokinetics of a Novel Testosterone Matrix Transdermal System in Health, Premenopaula Women and Women Infected with the Human Immunodeficiency Virus; Journal of Clinical Endocrinology & Metabolism; (2000); p. 2395-401; vol. 85(7).
Johnson; "Gastrointestinal Physiology"; Department of Physiology; University of Texas Medical School; (1997); p. 25-26, 93 106, 133-134, 136-137; Houston, Texas.
Julien; A Primer of Drug Action; (2001); p. 5-6; Ninth Edition.
Kalinchenko; Testosteron-korol' Gormonov 1 Gormon Korolei; The Journal; Sex and Life; (2004); p. 12-22; Retrieved on Mar. 26, 2010; http://www.laz.med.ru/interesting/publications/testosterone.html.
Langer; "New Methods of Drug Delivery"; Science; (Sep. 1990); p. 1527-1533; vol. 249(4976).
Lecluyse et al.; "In Vitro Models for Selection of Development Candidates. Permeability Studies to Define Mechanisms of Absorption Enhancement"; Advanced Drug Delivery Reviews; p. 163-183; vol. 23.
Leichtnam et al.; "Testosterone Hormone Replacement Therapy: State-of-the-Art and Emerging Technology"; Pharma. Res.; (2006); p. 1117-1132; vol. 23(6).
Lopezberestein and Fidler (eds.); Liposomes in the Therapy of Infectious Disease and Cancer; 1989; p. 353-365; Liss; New York.
MacGregor et al.; "Influence of Lipolysis on Drug Absorption From the Gastro-intestinal Tract"; Advanced Drug Delivery Reviews; (1997); p. 33-46; vol. 25.
Maisey et al; Clinical Efficacy of Testosterone Undercanoate in Male Hypogonadism; Clinical Endocrinology; (1981); p. 625-629; vol. 14.
McAuley et al; Oral Administration of Micronized Progesterone: A Review and More Experience; Pharmacotherapy; (May 1996); pp. 453-457; vol. 16(3).
Meiner et al.; Clinical Trials: Design, Conduct and Analysis; Monographs in Epidemiology and Biostatistis; (1986); vol. 8.
Merck Index, "Vitamin E" and "Vitamin E Acetate", Monographs 9931 and 9932, Merck & Co., Inc., 1989, p. 1579-1580; $11^{th}$ Edition.
Merck Index; "Fenofibrate" (Monograph 3978); Merck & Co., Inc.; (2006); p. 679-680; $14^{th}$ Edition.
Merck Index, 12th Ed., "Shellac", Monograph 8623, Merck & Co. 1996, pp. 8526.
Merck Index, 12th Ed., "Testosterone", Monograph 9322, Merck & Co. 1996, pp. 9326.

Merriam-Webster Dictionary; Granule; Retrieved Dec. 17, 2009; http://www.mw.com/dictionary/granule.
Mittal et al.; The Wide World of Micelles; International Business Machines Corporation and School of Pharmacy; University of Wisconsin, Madison; Wisconsin; (1976); pp. 1-21; vol. 1.
Moellering; "Vancomycin: A 50-Year Reassessment". Clinical Infectious Diseases. 2006; 42:S3-S4.
Muranishi; "Absorption Enhancers"; Critical Reviews in Therapeutic Drug Carrier Systems; (1990); p. 1-33; vol. 7(1).
Muranishi; "Potential Absorption of Heparin from the Small Intestine and the Large Intestine in the Presence of Monoolein Mixed Micelles"; Chem. Pharm. Bull.; (1977); p. 1159-1161; vol. 24(5).
Nieschlag et al.; "Plasma Androgen Levels in Men after Oral Administration of Testosterone or Testosterone Undecanoate"; Acta Endocrinologica; (1975); p. 366-374; vol. 79(2); (Abstract).
Noguchi et al; The Effect of Drug Lipophilicity and Lipid Vehicles on the Lympathics Absorption of Various Testosterone Esters; International Journal of Pharmaceutics; (1985); pp. 173-184; vol. 24.
Osol ed.; Remington's Pharmaceutical Sciences; (1975); p. 327-339, 1452-1456; $15^{th}$ edition.
Perchersky, A.V., et al. "Androgen administration in middle-aged and ageing men: effects of oral testosterone undecanoate on dihydrotestosterone, oestradiol and prostate volume." International Journal of Andrology, 25: 119-125 (2002).
Pouton; "Formulation of Self-Emulsifying Drug Delivery Systems"; Advanced Drug Delivery Reviews; (1997); p. 47-58; vol. 25.
Reymond et al.; "In Vitro Model for Ciclosporin Intestinal Absorption in Lipid Vehicles"; Pharmaceutical Research; p. 677-679; vol. 5(10).
S1 Sec Filing (Securities and Exchange Commission) for Clarus Therapeutics, Inc.; Filed May 23, 2014 with the Securities and Exchange Commission; 207 pages.
Saudek et al.; "A preliminary trial of the programmable implantable medication system for insulin delivery"; N. End J. Med; (Aug. 31, 1989); p. 574-579; vol. 321.
Schnabel et al.; "The effect of food composition on serum testosterone levels after oral administration of Andriol Testocaps"; Clinical Endocrinology; (2007); p. 579-585; vol. 66(4).
Schott; "Comments on Hydrophile-Lipophile Balance Systems"; J.Pharm.Sci.; (1990); p. 87-88; vol. 79(1).
sciencelab.com; Material Safety Data Sheet Glyceryl monooleate MSDS; www.sciencelab.com; (Oct. 2005); p. 1-5.P.
Sefton; "Implantable pumps"; Crit. Rev. Biomed. Eng.; (1987); p. 201-240; vol. 14(3); (Abstract).
Seidman et al.; "Testosterone replacement therapy for hypogonadal men with SSRI-refractory depression"; Journal of Affective Disorders; (1998); p. 157-161; vol. 48.
Shackleford et al., Contribution of Lymphatically Transported Testosterone Undecanoate to the Systemic Exposure of Testosterone after Oral Administration of Two Andriol Formulations in Conscious Lymph Duct-Cannulated Dogs. The Journal of Pharmacology and Experimental Therapeutics. vol. 306, No. 3 (2003).
Shanghai Pi Chemicals Ltd.; "Material Safety Data Sheet: Testosterone Undecanoate"; http://www.pipharm.com/products/msds-13457.pdf (2007); retrieved from internet Jun. 3, 2009.
Stedman's Medical Dictionary; "Surfactants"; (2006); $28^{th}$ Edition; Williams & Wilkins Co.
Stedman's Medical Dictionary; $22^{nd}$ Ed.; Hydroxy Acid and Vitamin E; (1973); pp. 595 and 14000.
Stedman's Medical Dictionary; $22^{nd}$ Ed.; Surfactants; (1972); p. 1225; Williams and Wilkins Co.
Stedman's Medical Dictionary; Dehydro-e-epiandrosterone, Dehydroisoandroteron, and Steroid; (1972); pp. 329 and 1195-1197; $22^{nd}$ Ed.; Williams & Wilkins Co.
Swerdoff, et al; "Long Term pharmaceokinetics of transdermal testosterone gel in hypogonadal men". J. Clin Endocrinol, Metab., 2000, 85:4500-4510.
Tarr et al.; "Enhanced Intestinal Absorption of Cyclosporine in Rats Through the Reduction of Emulsion Droplet Size"; Pharmaceutical Research; (1989); p. 40-43; vol. 6(1).

(56) References Cited

OTHER PUBLICATIONS

Tauber et al.; "Absolute bioavailability of testosterone after oral administration of testosterone-undecanoate and testosterone"; Eur. J. Drug Metab. Pharmacokinetics; (1986); p. 145-149; vol. 11(2); (Abstract).

Tenover, JL, "The Androgen-Deficient Aging Male: Current Treatment Options"; Reviews in Urology, 2003, vol. 5, Suppl. 1, S22-S28.

Testim® Product Label and Medication Guide; Sep. 2009; Labeler—A-S Medications Solutions LLC; Revised Jun. 2013; 17 pages.

Merck Index, "Alpha Tocopherol"; Monograph 09571, Merck & Co., 2001-2004.

Merck Index, "Carvedilo"; Monograph 01888, Merck & Co., 2001/2004.

Merck Index, "Risperidone"; Monograph 08316, Merck & Co., 2001-2004.

Merck Index, "Ziprasidone"; Monograph 10224, Merck & Co., 2001-2004.

Merck Index, 12$^{th}$ Ed., "Amiodarone", Monograph 504, Merck & Co., 1996, p. 84.

Torpac Inc. Metric Table for Capsule; 2000; (retrieved online Sep. 2014); http://www.torpac.com ; 3 pages; Fairfield, New Jersey.

Treat et al.; "Liposomes in the Therapy of Infectious Diseases and Cancer"; Lopez-Berestein and Fidler (eds.); (1989); p. 353-365. Liss, New York.

Tso, et al.; "Intestinal Absorption and Lymphatic Transport of a High y-Linolenic Acid Canola Oil in Lymph Fistula Sprague-Dawlwy Rats"; American society for Nutritional Sciences, 2002, pp. 218-221.

Wang, et al.; "Long-term testosterone gel (AndroGel®) treatment maintains beneficial effects on sexual function and mood, lean and fat mass and bone mineral density in hypogonadal men"; J. Clin. Metab., 2004, 89-2085-2098.

Wilson et al.; "The Behaviour of Fats and Oils in the Upper G.I. Tract"; Bulletin Technique Gattefosse; (1997); p. 13-18; vol. 90.

Winnie; "Dependence of Intestinal Absorption in Vivo on the Unstirred Layer"; Archives of Pharmacology; (1978); p. 175-181; vol. 304.

Yassin et al.; "Long-acting testosterone undecanoate for parenteral testosterone therapy"; Therapy, Future Drugs, 2006, 3(6): 709-721.

Yin et al., "Dietary Fat Modules Testosterone Pharmacokinetics of a New Self-Emulsifying Formulation of Oral Testosterone Undercanoate in Hypogonadal Men." Submitted Journal of Andrology, submitted Mar. 23, 2012, published ahead of print on Jul. 12, 2012.

Yin et al.; "Reexamination of Pharmacokinetics of Oral Testosterone Undercanoate in Hypogonadal Men with a New Self-Emulsifying Formulation"; Journal of Andrology; 2012; p. 190-201; vol. 33(2).

\* cited by examiner

IMPURITIES

(17-ß)-3-OXOANDROST-4-EN-17YL TRIDECANOATE COMPOSITIONS AND METHODS OF THEIR PREPARATION AND USE

CROSS-REFERENCE TO RELATED APPLICATIONS

This application is a continuation of U.S. patent application Ser. No. 15/507,754, filed Feb. 28, 2017, which is a national stage entry under 35 U.S.C. § 371 of PCT Application No. PCT/US2015/047579, filed Aug. 28, 2015, which claims the benefit of U.S. Provisional Application No. 62/043,343 filed Aug. 28, 2014, each of which is incorporated herein by reference in their entirety.

FIELD OF THE INVENTION

Disclosed herein are pharmaceutical compositions having or made from pure (17-β)-3-Oxoandrost-4-en-17-yl tridecanoate for administration to mammals, e.g., humans, in need thereof.

BACKGROUND

Worldwide marketing authorizations for pharmaceutical products set forth strict requirements for the stability and purity of pharmaceutical products regarding an active pharmaceutical ingredient (API) also known as drug or a prodrug of an API (also referred to herein as API) and its content. It is also critical that pure drug or prodrug is used in preparation of compositions or dosage forms of drugs or prodrugs to enable safe and effective use in treatment of appropriate disease conditions. Moreover, it is also important to limit all drug or prodrug related materials (starting impurities in the drug or prodrug, degradation product(s) derived from aging through chemical interaction between components of a composition or dosage form upon storage) to acceptable levels that are safe and do not limit shelf life of the composition or dosage form to an unacceptably short time.

A study recently found a number of (17-β)-hydroxy-4-androsten-3-one (also known as testosterone) replacement therapy products on the market that have problems with impurities (Baert et al. Volume 72, Issue 1, May 2009, Pages 275-281). (17-β)-3-Oxoandrost-4-en-17-yl tridecanoate is a novel ester prodrug of (17-β)-hydroxy-4-androsten-3-one that has demonstrated promise in early testing in treating mammals in need of (17-β)-hydroxy-4-androsten-3-one, a critical hormone useful for treating numerous conditions in males and females.

Due to its unique structure, (17-β)-3-Oxoandrost-4-en-17-yl tridecanoate is particularly prone to decomposition as a result of reactions such as oxidation, reduction, cleavage of the ester moiety; oxidation of the steroid ring system; cleavage of one or more rings of the steroid ring system; rearrangement of the steroid ring; dealkylation of the steroid ring; dealkylation of the ester; or a combination thereof. Thus, the preparation and identification of substantially pure (17-β)-3-Oxoandrost-4-en-17-yl tridecanoate and stable compositions and methods associated with use of stable (17-β)-3-Oxoandrost-4-en-17-yl tridecanoate is challenging. Furthermore, (17-β)-3-Oxoandrost-4-en-17-yl tridecanoate has a unique dosing regimen with a different unit dosage form and daily dose requirement for effectiveness as compared to conventional prodrugs of (17-β)-hydroxy-4-androsten-3-one reported to date. Therefore, a significant challenge that is unique to (17-β)-3-Oxoandrost-4-en-17-yl tridecanoate relates to absolute levels of allowable impurities and degradation products for safe use in therapeutic settings.

Impurities in (17-β)-3-Oxoandrost-4-en-17-yl tridecanoate can pose a number of problems to patients receiving (17-β)-3-Oxoandrost-4-en-17-yl tridecanoate for therapy. Since (17-β)-3-Oxoandrost-4-en-17-yl tridecanoate possesses a steroid core ring system, alteration of this molecule by decomposition or failure to remove synthetic by-products may result in exposing patients to potentially harmful agents. Compounds with steroid ring cores are often biologically active. For example, androstenedione (having a steroid core ring system similar to that of (17-β)-hydroxy-4-androsten-3-one but having the hydroxyl group as a keto group) induces abnormalities in morphology and function of developing oocytes in female mice. (Fertil Steril. 2012 February; 97(2):469-76. doi: 10.1016/j.fertnstert.2011.11.040) and androstenedione is carcinogenic in male and female mice Food Chem Toxicol. 2011 September; 49(9):2116-24. doi: 10.1016/j.fct.2011.05.026. Epub 2011 May 30.

Thus, there is a need for substantially pure (17-β)-3-Oxoandrost-4-en-17-yl tridecanoate and compositions (e.g., bulk drug substance, pharmaceutical, or unit dosage forms) containing substantially pure (17-β)-3-Oxoandrost-4-en-17-yl tridecanoate, which can be stored for prolonged periods without deterioration in their quality, decrease in potency below a specified limit, as well as an increase of the concentration of decomposition products above acceptable limits. Moreover, there is even more critical need to prepare compositions and dosage forms that are stable upon storage for up to two years (or more) and are safe, with adequate potency (e.g., at least 80%) and acceptable (17-β)-3-Oxoandrost-4-en-17-yl tridecanoate related substances in the compositions independent of using substantially pure starting (17-β)-3-Oxoandrost-4-en-17-yl tridecanoate prodrug. (17-β)-3-Oxoandrost-4-en-17-yl tridecanoate has the propensity to degrade or decompose. For example, (17-β)-3-Oxoandrost-4-en-17-yl tridecanoate has the propensity to convert to (17-β)-Hydroxy-4-androsten-3-one (or otherwise decompose) due to hydrolysis upon storage or interaction with components of the composition or dosage forms that are acidic, hygroscopic, have an unsaturated moiety in their structure and contaminants or catalyst in the prodrug or excipients. Loss of potency of these compositions, especially those containing lipid additives (with associated free radicals) could compromise product performance.

Thus, there is a need for (17-β)-3-Oxoandrost-4-en-17-yl tridecanoate products having acceptable levels of impurities, especially since this molecule has not yet received market authorization. Moreover, methods of stabilizing and inclusion of stabilizing agents that limit loss of potency of the compositions made with substantially (17-β)-3-Oxoandrost-4-en-17-yl tridecanoate prodrug is particularly needed for compositions (and dosage forms) for safe and effective human use. Ensuring safe levels of impurities and maintaining potency and stability of compounds like (17-β)-3-Oxoandrost-4-en-17-yl tridecanoate is no small task given the daily dose requirements and the chronic therapeutic use of such agents.

SUMMARY

Provided herein is substantially pure (17-β)-3-Oxoandrost-4-en-17-yl tridecanoate pharmaceutical ingredient and compositions containing substantially pure (17-β)-3-Oxoandrost-4-en-17-yl tridecanoate. In one embodiment, a substantially pure API or composition can have greater than 80% potency. Substantially pure (17-β)-3-Oxoandrost-4-en-17-yl tridecanoate includes (17-β)-3-Oxoandrost-4-en-17-yl tridecanoate substantially free of synthetic impurities, decomposition impurities, or both. In one embodiment an API or composition that is substantially free of impurities can have less than 20% of total impurities (known and unknown). The compositions of substantially pure (17-β)-3-Oxoandrost-4-en-17-yl tridecanoate include substantially pure (17-β)-3-Oxoandrost-4-en-17-yl tridecanoate pharmaceutical ingredient, pharmaceutical compositions comprised of or prepared from substantially pure (17-β)-3-Oxoandrost-4-en-17-yl tridecanoate pharmaceutical ingredient and a pharmaceutically acceptable carrier, and unit dosage forms comprised of or prepared from substantially pure (17-β)-3-Oxoandrost-4-en-17-yl tridecanoate pharmaceutical ingredient and a pharmaceutically acceptable carrier. Substantially pure (17-β-3-Oxoandrost-4-en-17-yl tridecanoate is useful for administration to a subject (e.g., mammalian; human) to provide safe and effective levels of (17-β)-3-Oxoandrost-4-en-17-yl tridecanoate and (17-β)-hydroxy-4-androsten-3-one. For example, substantially pure (17-β)-3-Oxoandrost-4-en-17-yl tridecanoate can be used to treat a subject having hypogonadism or any other disorder, disease or conditions associated with low levels of (17-β)-hydroxy-4-androsten-3-one or that can be improved or prevented with (17-β)-hydroxy-4-androsten-3-one. Substantially pure (17-β)-3-Oxoandrost-4-en-17-yl tridecanoate is useful in pharmaceutical applications and has exceptional safety characteristics as well as stability.

DETAILED DESCRIPTION OF THE INVENTION

Figure 1A:
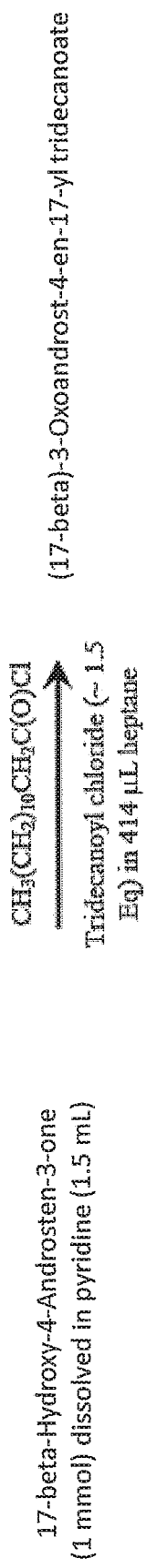
FIG. 1A shows a non-limiting example of a synthetic scheme for (17-β)-3-Oxoandrost-4-en-17-yl tridecanoate.
Figure 1B:
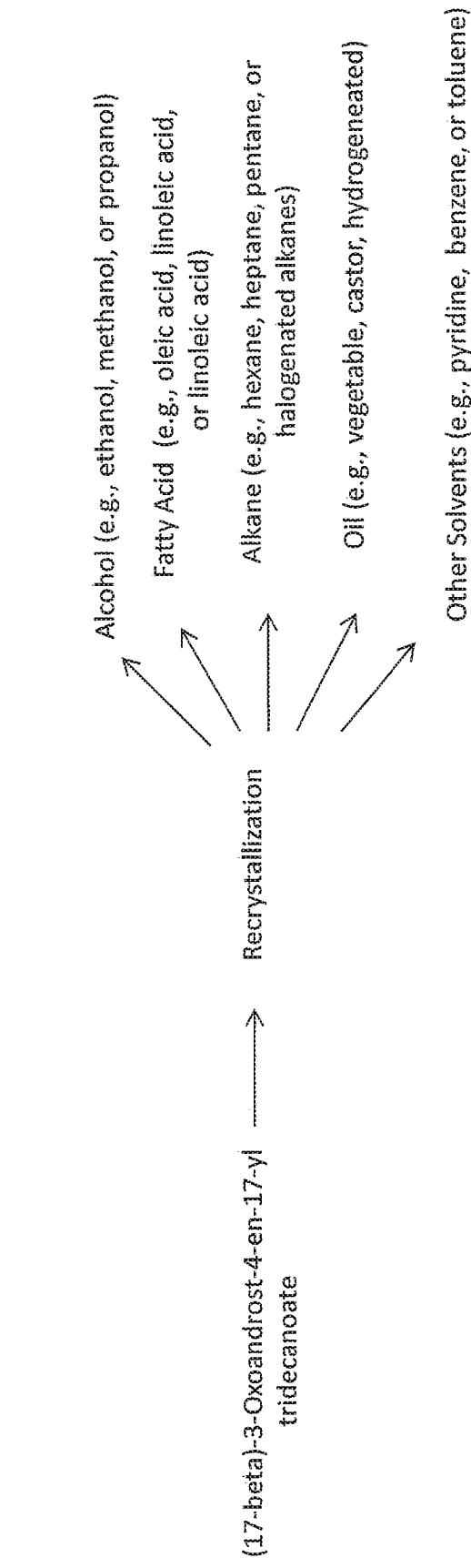
FIG. 1B shows non-limiting examples of crystallization of (17-β)-3-Oxoandrost-4-en-17-yl tridecanoate.
Figure 2:
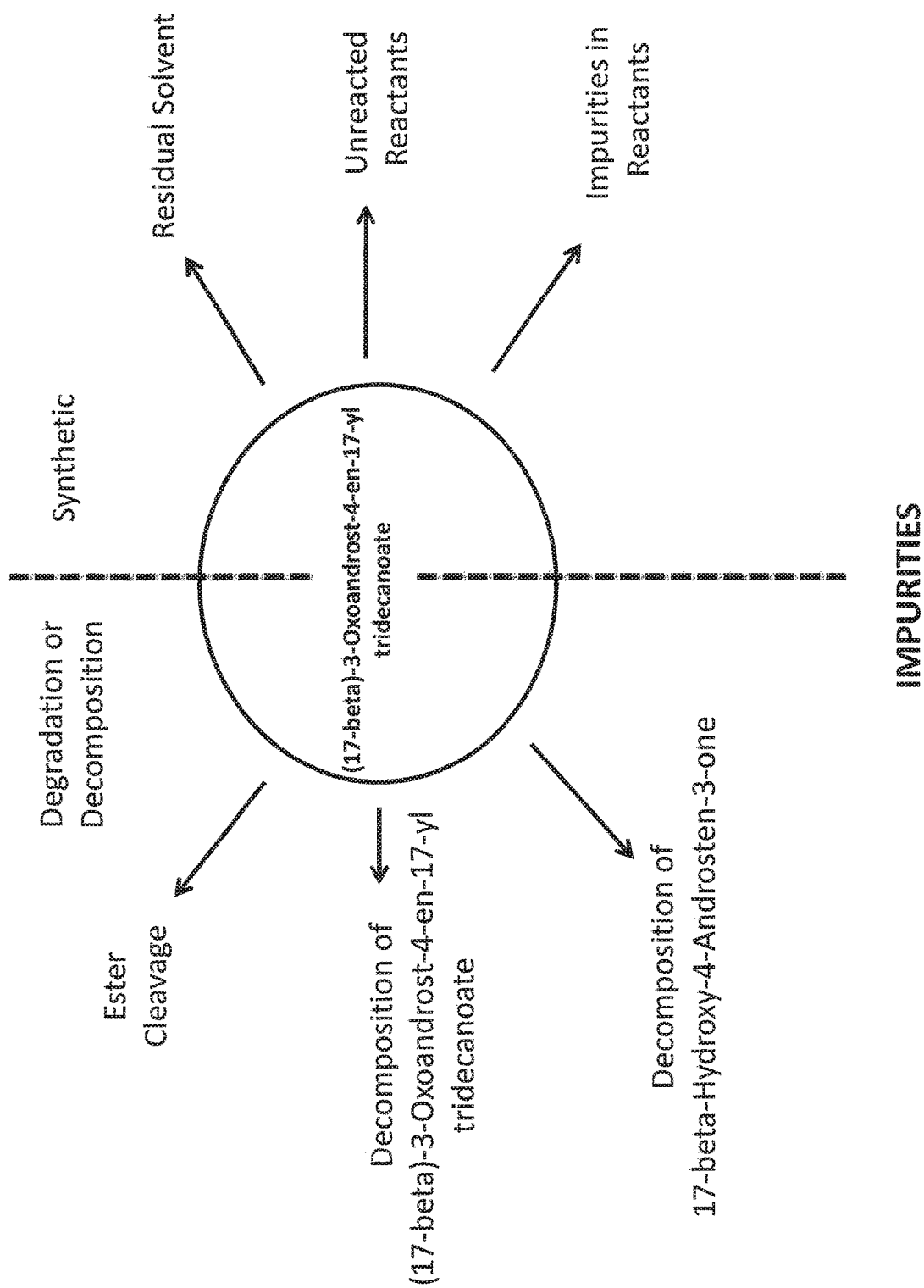
FIG. 2 shows general classification of potential impurities in (17-β)-3-Oxoandrost-4-en-17-yl tridecanoate samples.

As described herein, substantially pure compositions of (17-β)-3-Oxoandrost-4-en-17-yl tridecanoate are provided that are free of synthetic impurities, decomposition impurities, or both. The substantially pure compositions of (17-β)-3-Oxoandrost-4-en-17-yl tridecanoate described herein include hulk prodrug, pharmaceutical compositions having substantially pure (17-β)-3-Oxoandrost-4-en-17-yl tridecanoate and unit dosage forms having substantially pure (17-β)-3-Oxoandrost-4-en-17-yl tridecanoate. The compositions described herein may further include a stabilizing agent or are stored under stabilizing conditions. Additionally, methods of using substantially pure compositions of (17-β)-3-Oxoandrost-4-en-17-yl tridecanoate are described, including methods of treatment (e.g., treating a disease, disorder or condition in an individual), and methods of producing or preparing compositions. The pharmaceutical compositions described herein have substantially pure (17-β)-3-Oxoandrost-4-en-17-yl tridecanoate and a pharmaceutically acceptable carrier. Unit dosage forms can be formed from the pharmaceutical compositions e.g., tablet or capsule (soft gel or hard gel).

Definitions

It should be noted that, the singular forms "a," "an," and, "the" include plural references unless the context clearly dictates otherwise. Thus, for example, reference to "an excipient" includes reference to one or more of such excipients, and reference to "the carrier" includes reference to one or more of such carriers.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

In this specification, "comprises," "comprising," "comprised of," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

As used herein, "active pharmaceutical ingredient" refers to (17-β)-3-Oxoandrost-4-en-17-yl tridecanoate. The biological active metabolite of (17-β)-3-Oxoandrost-4-en-17-yl tridecanoate is (17-β)-Hydroxy-4-Androsten-3-one which is produced in vivo by de-esterification. Another important biologically active metabolite is (17-β)-hydroxy-5α-androstan-3-one with an IUPAC name of (5S,8R,9S,10S,13S,14S,17S)-17-hydroxy-10,13-dimethyl-1,2,4,5,6,7,8,9,11,12,14,15,16,17-tetradecahydrocyclopenta[a]phenanthren-3-one (CAS No. 521-18-6).

As used herein, the term "(17-β)-Hydroxy-4-Androsten-3-one" refers to a chemical having an IUPAC name of (8R,9S,10R,13S,14 S,17S)-17-Hydroxy-10,13-dimethyl-1,2,6,7,8,9,11,12,14,15,16,17-dodecahydrocyclopenta[a]phenanthren-3-one and a CAS number of 58-22-0. (17-β)-3-Oxoandrost-4-en-17-yl tridecanoate refers to a compound having the (17-β)-Hydroxy-4-Androsten-3-one core structure but the hydroxyl group is esterified with tridecanoic acid e.g., (17-β)-Hydroxy-4-Androsten-3-one esterified with a straight chain saturated 13 carbon long alkanoic acid called tridecanoic acid Tridecanoic acid is the IUPAC name for the alkanoic acid having CAS number 638-53-9.

As used herein, "impurity" or "impurities" refer to a chemical or chemical that is not (17-β)-3-Oxoandrost-4-en-17-yl tridecanoate but is derived from the synthesis, preparation, processing, degradation or decomposition of (17-β)-3-Oxoandrost-4-en-17-yl tridecanoate. Typically, the impurity is a synthetic impurity or a decomposition impurity. Impurities typically can be derived from decomposition, degradation or the chemical reaction of (17-β)-3-Oxoandrost-4-en-17-yl tridecanoate which can be referred to as related compounds or "RC" or "RCs". Other impurities can be present as described herein and are typically synthetic by-products, solvents, etc., derived from the manufacturing or processing of the API. Although synthetic and decomposition impurities are used to categorize classes described herein, they are not mutually exclusive and it is not always certain where or how a particular impurity arises.

As used herein, "substantially pure" refers to a composition having an active pharmaceutical ingredient which meets applicable regulatory requirements in terms of potency. In this context, potency refers to the comparison of a reference standard deemed to be 100% potent by any number of techniques including NMR, elemental analysis, IR, chromatography (e.g., HPLC) and the such. In one definition, potency is defined in terms of the definition provided by a compendium e.g., the United States Pharmacopeia, European Pharmacopeia or other national or regional Pharmacopeia. Potency can be determined by one of ordinary skill in the art in view of the definition in the compendium or as described herein. In one embodiment, the substantially pure (17-β)-3-Oxoandrost-4-en-17-yl tridecanoate or related compositions has greater than 80%, 85%, 90%, 95%, 96%, 97%, 98% or 99% potency.

As used herein, "substantially free of impurities" refers to a composition having active pharmaceutical ingredient which meets applicable regulatory requirements for levels of impurities (e.g., below a specific level). Depending on the context, substantially free of impurities can refer to all impurities or a specific impurity which is 50% or less, 40% or less, 30% or less, 20% or less, 10% or less, 5% or less, 3% or less, 2% or less, 1% or less, 0.5% or less, 0.3% or less, 0.2% or less, or 0.1% or less by total weight of active pharmaceutical ingredient and the specific impurity or impurities (or total impurities). Unless otherwise specified percent impurity is calculated as the (total weight of a specific impurity or impurities)/(total weight of API+weight of specific impurity or impurities)*100. In some instances, other methods beside weight are used to characterize impurities, like area under the curves of HPLC traces or NMR signals which can be used to calculate percent impurities also. The impurities can be decomposition impurities, synthetic impurities, or any other impurity. The synthetic impurities, in some aspects, refers to those identified in the examples, figures, or elsewhere herein.

As used herein, "substantially free of synthetic impurities" refers to a composition having (17-β)-3-Oxoandrost-4-en-17-yl tridecanoate which meets applicable regulatory requirements for levels of impurities (e.g., below a specific level) where the impurity is related to synthesis and/or processing of (17-β)-3-Oxoandrost-4-en-17-yl tridecanoate.

Depending on the context, substantially free of synthetic impurities can refer to all synthetic impurities or a specific synthetic impurity which is 50% or less, 40% or less, 30% or less, 20% or less, 10% or less, 5% or less, 3% or less, 2% or less, 1% or less, 0.5% or less, 0.3% or less, 0.2% or less, or 0.1% or less by total weight of (17-β)-3-Oxoandrost-4-en-17-yl tridecanoate and the specific synthetic impurity or impurities. The synthetic impurities, in some aspects, refer to those identified in the examples, figures, or elsewhere herein. Synthetic impurities of (17-β)-3-Oxoandrost-4-en-17-yl tridecanoate include, but are not limited to, starting materials, by-products (from reactions of reagents or other materials), side-products (from reaction of impurities in reagents or other materials), intermediates, degradation (or decomposition) products, reagents, ligands, catalysts, residual solvents (e.g., from the synthesis, purification or processing of API). Specific synthetic impurities include, 17-β-Hydroxy-4-Androsten-3-one, tridecanoic acid (or a salt form thereof), tridecanoyl chloride, etc. or a non-API compound derived therefrom, pyridine, heptane, heptanes, etc.

As used herein, "substantially free of decomposition impurities" refers to a composition having (17-β)-3-Oxoandrost-4-en-17-yl tridecanoate which meets applicable regulatory requirements for levels of impurities related to the decomposition (including degradation) of (17-β)-3-Oxoandrost-4-en-17-yl tridecanoate (e.g., below a specific level). Depending on the context, free of decomposition impurities can refer to all decomposition impurities or a specific synthetic impurity which is 50% or less, 40% or less, 30% or less, 20% or less, 10% or less, 5% or less, 3% or less, 2% or less, 1% or less, 0.5% or less, 0.3% or less, 0.2% or less, or 0.1% or less by total weight of (17-β)-3-Oxoandrost-4-en-17-yl tridecanoate and the specific or known decomposition impurity or unknown or unspecified impurities. The decomposition impurities, in some aspects, refer to those identified in the examples, figures, or elsewhere herein. Decomposition impurities include, but are not limited to (17-β)-hydroxy-4-androsten-3-one, an oxidation product of (17-β)-3-Oxoandrost-4-en-17-yl tridecanoate, an oxidation product of 17-β-Hydroxy-4-Androsten-3-one, or other decomposition products.

In one embodiment, the impurity is 3-Oxoandrost-1,4-dien-17β-yl tridecanoate, 3-Oxoandrost-4,6-dien-17β-yl tridecanoate, 17 beta-hydroxy androst-4-en-3-one tridecylenate (e.g., tridec-12-enoate), 3-Oxoandrost-4-en-17α-yl tridecanoate, 4-Androstene-3,17-dione, 17α-hydroxyandrost-4-en-3one, 4-Androstene-3β,17β-diol, androsta-1,4-dien-3,17-dione, 17β-hydroxyandrosta-4,6-dien-3-one, 17β-hydroxy-5α-androstan-3-one, or 17β-hydroxyandrost-1,4-dien-3-one.

In one embodiment, the impurity is as shown in any of the Figures.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

Provided herein are compositions containing substantially pure (17-β)-3-Oxoandrost-4-en-17-yl tridecanoate. The substantially pure (17-β)-3-Oxoandrost-4-en-17-yl tridecanoate can be substantially free of impurities. Impurities of compositions containing (17-β)-3-Oxoandrost-4-en-17-yl tridecanoate include, but are not limited to, synthetic impurities, decomposition impurities, or both. In one aspect, the substantially pure (17-β)-3-Oxoandrost-4-en-17-yl tridecanoate is substantially free of impurities specifically disclosed herein or in any of the Figures.

In one embodiment, a substantially pure (17-β)-3-Oxoandrost-4-en-17-yl tridecanoate composition is provided that is at least 80%, 85% or 90% substantially pure (17-β)-3-Oxoandrost-4-en-17-yl tridecanoate. According to an aspect of this embodiment, the composition comprises at least 95% substantially pure (17-β)-3-Oxoandrost-4-en-17-yl tridecanoate. In a more specific aspect, the composition comprises at least 97% substantially pure (17-β)-3-Oxoandrost-4-en-17-yl tridecanoate. In another more specific aspect, the composition comprises at least 98% substantially pure (17-β)-3-Oxoandrost-4-en-17-yl tridecanoate. In another more specific aspect, the composition comprises at least 99% substantially pure (17-β)-3-Oxoandrost-4-en-17-yl tridecanoate. In another more specific aspect, the composition comprises at least 99.5% substantially pure (17-β)-3-Oxoandrost-4-en-17-yl tridecanoate. In a specific aspect, the substantially pure (17-β)-3-Oxoandrost-4-en-17-yl tridecanoate is substantially free of impurities. In one embodiment, substantially pure (17-β)-3-Oxoandrost-4-en-17-yl tridecanoate is a white crystalline or amorphous powder. In one aspect, at least 1 g, 10 g, 50 g, 100 g, 500 g, 1 kg, 5 kg, 10 kg, 50 kg, 100 kg, 500 kg, 1000 kg, 5000 kg 10,000 kg, 50,000 kg of substantially pure (17-β)-3-Oxoandrost-4-en-17-yl tridecanoate is provided. In one aspect, the substantially pure (17-β)-3-Oxoandrost-4-en-17-yl tridecanoate is substantially free of impurities specifically disclosed herein or in any of the Figures.

In another embodiment, a pharmaceutical composition is provided which comprises or is prepared from (17-β)-3-Oxoandrost-4-en-17-yl tridecanoate that is at least 80%, 85% or 90% substantially pure (17-β)-3-Oxoandrost-4-en-17-yl tridecanoate and a pharmaceutically acceptable carrier. According to an aspect of this embodiment, the pharmaceutical composition comprises or is prepared from (17-β)-3-Oxoandrost-4-en-17-yl tridecanoate that is at least 95% substantially pure (17-β)-3-Oxoandrost-4-en-17-yl tridecanoate and a pharmaceutically acceptable carrier. In a more specific aspect, the pharmaceutical composition comprises or is prepared from (17-β)-3-Oxoandrost-4-en-17-yl tridecanoate that is at least 97% substantially pure (17-β)-3-Oxoandrost-4-en-17-yl tridecanoate and a pharmaceutically acceptable carrier. In another more specific aspect, the pharmaceutical composition comprises or is prepared from (17-β)-3-Oxoandrost-4-en-17-yl tridecanoate that is at least 98% substantially pure (17-β)-3-Oxoandrost-4-en-17-yl tridecanoate and a pharmaceutically acceptable carrier. In another more specific aspect, the pharmaceutical composition comprises or is prepared from (17-β)-3-Oxoandrost-4-en-17-yl tridecanoate that is at least 99% substantially pure (17-β)-3-Oxoandrost-4-en-17-yl tridecanoate and a pharmaceutically acceptable carrier. In another more specific aspect, the pharmaceutical composition comprises or is prepared from (17-β)-3-Oxoandrost-4-en-17-yl tridecanoate that is at least 99.5% substantially pure (17-β)-3-Oxoandrost-4-en-17-yl tridecanoate and a pharmaceutically acceptable carrier. In a specific aspect, the pharmaceutical composition comprises or is prepared from substantially pure (17-β)-3-Oxoandrost-4-en-17-yl tridecanoate that is a white crystalline or amorphous powder. Pharmaceutical compositions of this embodiment are suitable for any form of administration. For example, the pharmaceutical formulations can be formulated for enteral, parenteral, or topical administration. In one aspect, the substantially pure (17-β)-3-Oxoandrost-4- en-17-yl tridecanoate is substantially free of impurities. In one aspect, the substantially pure (17-β)-3-Oxoandrost-4-en-17-yl tridecanoate is substantially free of impurities specifically disclosed herein or in any of the Figures.

In yet another embodiment, a unit dosage form is provided which comprises or is prepared from (17-β)-3-Oxoandrost-4-en-17-yl tridecanoate that is at least 80%, 85% or 90% substantially pure (17-β)-3-Oxoandrost-4-en-17-yl tridecanoate and a pharmaceutically acceptable carrier. According to an aspect of this embodiment, the unit dosage form comprises or is prepared from (17-β)-3-Oxoandrost-4-en-17-yl tridecanoate and that is at least 95% substantially pure (17-β)-3-Oxoandrost-4-en-17-yl tridecanoate and a pharmaceutically acceptable carrier. In a more specific aspect, the unit dosage form comprises or is prepared from substantially pure (17-β)-3-Oxoandrost-4-en-17-yl tridecanoate that is at least 97% substantially pure (17-β)-3-Oxoandrost-4-en-17-yl tridecanoate and a pharmaceutically acceptable carrier. In another more specific aspect, the unit dosage form comprises or is prepared from (17-β)-3-Oxoandrost-4-en-17-yl tridecanoate that is at least 98% substantially pure (17-β)-3-Oxoandrost-4-en-17-yl tridecanoate and a pharmaceutically acceptable carrier. In another more specific aspect, the unit dosage form comprises or is prepared from (17-β)-3-Oxoandrost-4-en-17-yl tridecanoate that is at least 99% substantially pure (17-β)-3-Oxoandrost-4-en-17-yl tridecanoate and a pharmaceutically acceptable carrier. In another more specific aspect, the unit dosage form comprises or is prepared from (17-β)-3-Oxoandrost-4-en-17-yl tridecanoate that is at least 99.5% substantially pure (17-β)-3-Oxoandrost-4-en-17-yl tridecanoate and a pharmaceutically acceptable carrier. In a specific aspect, the unit dosage form comprises or is prepared from pharmaceutical ingredient, (17-β)-3-Oxoandrost-4-en-17-yl tridecanoate, that is a white crystalline or amorphous powder. Unit dosage forms of this embodiment are suitable for any form of administration. For example, the unit dosage form of the compositions of this invention can be formulated for enteral, parenteral, or topical administration. In one aspect, the substantially pure (17-β)-3-Oxoandrost-4-en-17-yl tridecanoate is substantially free of impurities. In one aspect, the substantially pure (17-β)-3-Oxoandrost-4-en-17-yl tridecanoate is substantially free of impurities specifically disclosed herein or in any of the Figures.

In one embodiment, a substantially pure (17-β)-3-Oxoandrost-4-en-17-yl tridecanoate composition is provided. According to this embodiment, the composition comprises at least 95% (17-β)-3-Oxoandrost-4-en-17-yl tridecanoate. In a more specific aspect, the composition comprises at least 97% (17-β)-3-Oxoandrost-4-en-17-yl tridecanoate. In another more specific aspect, the composition comprises at least 98% (17-β)-3-Oxoandrost-4-en-17-yl tridecanoate. In another more specific aspect, the composition comprises at least 99% (17-β)-3-Oxoandrost-4-en-17-yl tridecanoate. In another more specific aspect, the composition comprises at least 99.5% (17-β)-3-Oxoandrost-4-en-17-yl tridecanoate. In a specific aspect, the active pharmaceutical ingredient is a white crystalline or amorphous powder. According to one aspect of this embodiment, the substantially pure (17-β)-3-Oxoandrost-4-en-17-yl tridecanoate comprises less than 20%, 15% or 10% impurities (e.g., total impurities (known+unknown)). In a more specific aspect, the (17-β)-3-Oxoandrost-4-en-17-yl tridecanoate comprises less than 5% total impurities. In another more specific aspect, the (17-β)-3-Oxoandrost-4-en-17-yl tridecanoate comprises less than 3% total impurities. In another more specific aspect, the (17-β)-3-Oxoandrost-4-en-17-yl tridecanoate comprises less than 2% total impurities. In another more specific aspect, the (17-β)-3-Oxoandrost-4-en-17-yl tridecanoate comprises less than 1% total impurities. In another more specific aspect, the (17-β)-3-Oxoandrost-4-en-17-yl tridecanoate comprises less than 5% 17-β-Hydroxy-4-Androsten-3-one. In another more specific aspect, the (17-β)-3-Oxoandrost-4-en-17-yl tridecanoate comprises less than 3% 17-β-Hydroxy-4-Androsten-3-one. In another more specific aspect, the (17-β)-3-Oxoandrost-4-en-17-yl tridecanoate comprises less than 2% 17-β-Hydroxy-4-Androsten-3-one. In another more specific aspect, the (17-β)-3-Oxoandrost-4-en-17-yl tridecanoate comprises less than 1% 17-β-Hydroxy-4-Androsten-3-one. In another more specific aspect, the (17-β)-3-Oxoandrost-4-en-17-yl tridecanoate comprises less than 0.5% 17-β-Hydroxy-4-Androsten-3-one. In another specific aspect, the (17-β)-3-Oxoandrost-4-en-17-yl tridecanoate comprises less than 20000 ppm of a solvent (e.g., ethanol). In another more specific aspect, the (17-β)-3-Oxoandrost-4-en-17-yl tridecanoate comprises less than 10000 ppm of a solvent (e.g., ethanol). In another more specific aspect, the (17-β)-3-Oxoandrost-4-en-17-yl tridecanoate comprises less than 5000 ppm of a solvent (e.g., ethanol). In another more specific aspect, the (17-β)-3-Oxoandrost-4-en-17-yl tridecanoate comprises less than 3000 ppm of a solvent (e.g., ethanol). In another more specific aspect, the (17-β)-3-Oxoandrost-4-en-17-yl tridecanoate comprises less than 2000 ppm ethanol. In another more specific aspect, the (17-β)-3-Oxoandrost-4-en-17-yl tridecanoate comprises less than 1500 ppm of a solvent (e.g., ethanol). In a specific aspect, the (17-β)-3-Oxoandrost-4-en-17-yl tridecanoate is a white crystalline or amorphous powder. In one specific aspect, the (17-β)-3-Oxoandrost-4-en-17-yl tridecanoate composition comprises less than 3% or 2% of a single unknown impurity. In one specific aspect, the (17-β)-3-Oxoandrost-4-en-17-yl tridecanoate composition comprises less than 1% of a single unknown impurity. In one specific aspect, the (17-β)-3-Oxoandrost-4-en-17-yl tridecanoate composition comprises less than 0.5% of a single unknown impurity. In one specific aspect, the (17-β)-3-Oxoandrost-4-en-17-yl tridecanoate composition comprises less than 0.1% of a single unknown impurity. In one specific aspect, the (17-β)-3-Oxoandrost-4-en-17-yl tridecanoate composition comprises less than 5% of a single known impurity. In one specific aspect, the (17-β)-3-Oxoandrost-4-en-17-yl tridecanoate composition comprises less than 3% of a single known impurity. In one specific aspect, the (17-β)-3-Oxoandrost-4-en-17-yl tridecanoate composition comprises less than 2% of a single known impurity. In one specific aspect, the (17-β)-3-Oxoandrost-4-en-17-yl tridecanoate composition comprises less than 1% of a single known impurity. In one specific aspect, the (17-β)-3-Oxoandrost-4-en-17-yl tridecanoate composition comprises less than 0.5% of a single known impurity. In one aspect, the substantially pure (17-β)-3-Oxoandrost-4-en-17-yl tridecanoate is substantially free of impurities specifically disclosed herein or in any of the Figures.

As used herein, an impurity is "known" if its structure or chemical identity is known and an impurity is "unknown" if its structure or chemical identity is known.

Thus, substantially pure (17-β)-3-Oxoandrost-4-en-17-yl tridecanoate pharmaceutical ingredient or composition or dosage form comprising (17-β)-3-Oxoandrost-4-en-17-yl tridecanoate which is useful for dosing of 300-400, 400-500, 500-600, 600-700, 700-800, 800-900, 900-1000, 1000-1100, 1100-1200, 1200-1300, 1300-1400, 1400-1500, 1500-1600, 1600-1700, 1700-1800, 1900-2000, 2000-2500, 2500-3000, 3000-3500, 3500-4000, or 5000 or more mg per day to an individual, has greater than 80%, 85%, 90%, 95%, 98%, or 99% potency is provided. In one aspect, substantially pure (17-β)-3-Oxoandrost-4-en-17-yl tridecanoate substantially free of impurities is provided. In another aspect, substantially pure (17-β)-3-Oxoandrost-4-en-17-yl tridecanoate of having less than 20, 15, 10, 9, 8, 7, 6, 5, 4, 3, 2, or 1% of total impurities (known+unknown) is provided. In one aspect, substantially pure (17-β)-3-Oxoandrost-4-en-17-yl tridecanoate having less than 10, 9, 8, 7, 6, 5, 4, 3, 2, or 1% of total unknown impurities is also provided. In one aspect, substantially pure (17-β)-3-Oxoandrost-4-en-17-yl tridecanoate substantially free of any single known impurity is provided. In another aspect, substantially pure (17-β)-3-Oxoandrost-4-en-17-yl tridecanoate having less than 10, 5, 2, 1, or 0.5% of any single known impurity is provided. In another aspect, substantially pure (17-β)-3-Oxoandrost-4-en-17-yl tridecanoate substantially free of any single unknown impurity is provided. In one aspect, substantially pure (17-β)-3-Oxoandrost-4-en-17-yl tridecanoate having less than 5, 4, 3, 2, 1, 0.5 or 0.2% or less of any single unknown impurity is provided. In one aspect, substantially pure (17-β)-3-Oxoandrost-4-en-17-yl tridecanoate safe for administration to a human subject is provided (e.g., male or female). In one aspect, the substantial pure (17-β)-3-Oxoandrost-4-en-17-yl tridecanoate is safe for chronic administration (e.g., more than 1, 2, 3, or 4 weeks; more than 1, 2, 3, 4, 6, 9, 12 months; more than 1, 2, 3, 4, or 5 years) at daily doses of 300 mg to 1500 mg (e.g., 300 to 1000 mg or 400 mg to 900 mg) to a human. In one aspect, the substantial pure (17-β)-3-Oxoandrost-4-en-17-yl tridecanoate is safe for administration as a testosterone replacement therapy to a hypogonadal male. In one aspect, the substantially pure (17-β)-3-Oxoandrost-4-en-17-yl tridecanoate is stable. In some aspects, stable refers to a composition meeting one or more of the purity or impurity profiles described herein. In one aspect, the substantially pure (17-β)-3-Oxoandrost-4-en-17-yl tridecanoate having less than 20, 15, 10, 5 or 2% or less decomposition product of (17-β)-3-Oxoandrost-4-en-17-yl tridecanoate is provided. In one aspect, the substantially pure (17-β)-3-Oxoandrost-4-en-17-yl tridecanoate has less than 20, 15, 10, 5 or 2% or less decomposition product of (17-β)-3-Oxoandrost-4-en-17-yl tridecanoate at 90 days at 20-25° C. is provided. In a related aspect, substantially pure (17-β)-3-Oxoandrost-4-en-17-yl tridecanoate of the previous sentence wherein the decomposition product of (17-β)-3-Oxoandrost-4-en-17-yl tridecanoate results from oxidation, reduction, cleavage of the ester moiety; oxidation of the steroid ring system; cleavage of one or more rings of the steroid ring system; rearrangement of the steroid ring; dealkylation of the steroid ring; dealkylation of the ester; or a combination thereof is provided. In one aspect, the substantially pure comprises more than 80, 85, 90, 95, 98, 99, 99.5 or 99.8% substantially (17-β)-3-Oxoandrost-4-en-17-yl tridecanoate. In one aspect, the substantially pure (17-β)-3-Oxoandrost-4-en-17-yl tridecanoate comprises less than 10, 5, 4, 3, 2, 1, or 0.5% 17-β-Hydroxy-4-Androsten-3-one. In one aspect, the substantially pure (17-β)-3-Oxoandrost-4-en-17-yl tridecanoate comprising less than 50,000, 25000, or 15000 PPM of residual solvent (e.g., ethanol). In one aspect, a pharmaceutical composition comprising a pharmaceutically acceptable carrier and substantially pure (17-β)-3-Oxoandrost-4-en-17-yl tridecanoate is provided. In one aspect, the pharmaceutical composition is stable or total impurities, total unknown impurities, any single known impurity, or any single unknown impurity does not increase above acceptable levels after 1 month, 3 months, 6 months, 9 months, one year, or two years at a specified temperature (e.g., 20, 25, 37, 40 or 60° C.) with no more than 10% or 20% decomposition or 10 or 20% loss in potency of (17-β)-3-Oxoandrost-4-en-17-yl tridecanoate. In one aspect, the pharmaceutical composition comprises a stabilizing agent. In one aspect, the pharmaceutical composition comprises a pharmaceutically acceptable stabilizing agent which is an antioxidant, bufferant, complexing agent or dessicant. In one aspect, the pharmaceutical composition is formulated for topical, enteral or parenteral administration. In one aspect, the pharmaceutical composition is formulated for oral, buccal, sublingual, or sublabial administration. In one aspect, the pharmaceutical composition is formulated for nasal, rectal or vaginal administration. In one aspect, the pharmaceutical composition is formulated for intravenous, subcutaneous, intramuscular, intradermal, intraspinal, intrathecal, or intra-arterial administration. In one aspect, the pharmaceutical composition is a liquid, solution, suspension, dispersion, solid, semi-solid, a gel, a lotion, paste, foam, spray, emulsion, syrup, or ointment. In one aspect, the pharmaceutical composition is formulated as a tablet or capsule. In one aspect, the pharmaceutical composition is formulated as a tincture, patch, injectable, tablet, capsule, sprinkle, aggregate, granule, drink, or powder. In one aspect, a unit dosage form comprising a pharmaceutically acceptable carrier and the substantially pure (17-β)-3-Oxoandrost-4-en-17-yl tridecanoate described herein which is useful for dosing up to 2000 mg per day to an individual, has greater than 80%, 85%, 90%, 95%, 98%, or 99% potency and a pharmaceutically acceptable carrier is provided. In one aspect, the unit dosage form comprises a stabilizing agent. In one aspect, the unit dosage form comprises a pharmaceutically acceptable stabilizing agent which is an antioxidant, bufferant, complexing agent or desiccant. In one aspect, the unit dosage form is formulated for topical, parenteral or enteral administration. In one aspect, the unit dosage form is a solid, a semi-solid, a gel, a lotion, a paste, tincture, foam, spray, suspension, dispersion, syrup, patch, or ointment. In one aspect, the unit dosage form is formulated for an oral route of administration. In one aspect, the unit dosage form is a tablet or capsule. In one aspect, the unit dosage form comprises or is prepared from at least 3, 5, 10, 15, 30, 25, 30, 40, 50, 60, 75, 100, 125, 150, 175, 200, 225, 250, 275 or 300 mg of substantially pure (17-β)-3-Oxoandrost-4-en-17-yl tridecanoate. In one aspect, the substantially pure (17-β)-3-Oxoandrost-4-en-17-yl tridecanoate is substantially free of impurities. In one aspect, the substantially pure (17-β)-3-Oxoandrost-4-en-17-yl tridecanoate is substantially free of impurities specifically disclosed herein or in any of the Figures.

Synthetic Impurities

Figure 3:
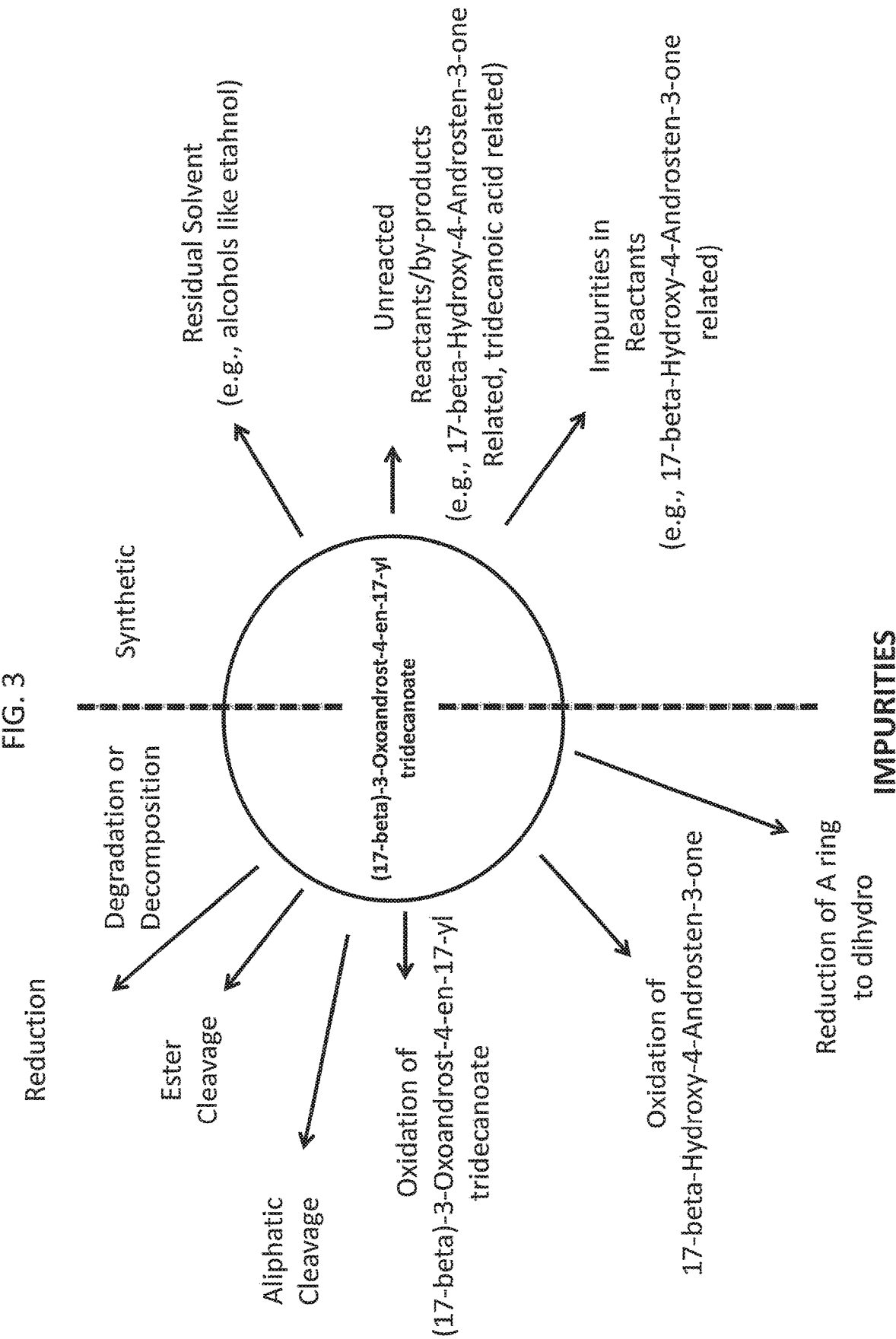
FIG. 3 shows a classification of potential impurities in (17-β)-3-Oxoandrost-4-en-17-yl tridecanoate samples.
Figure 4:
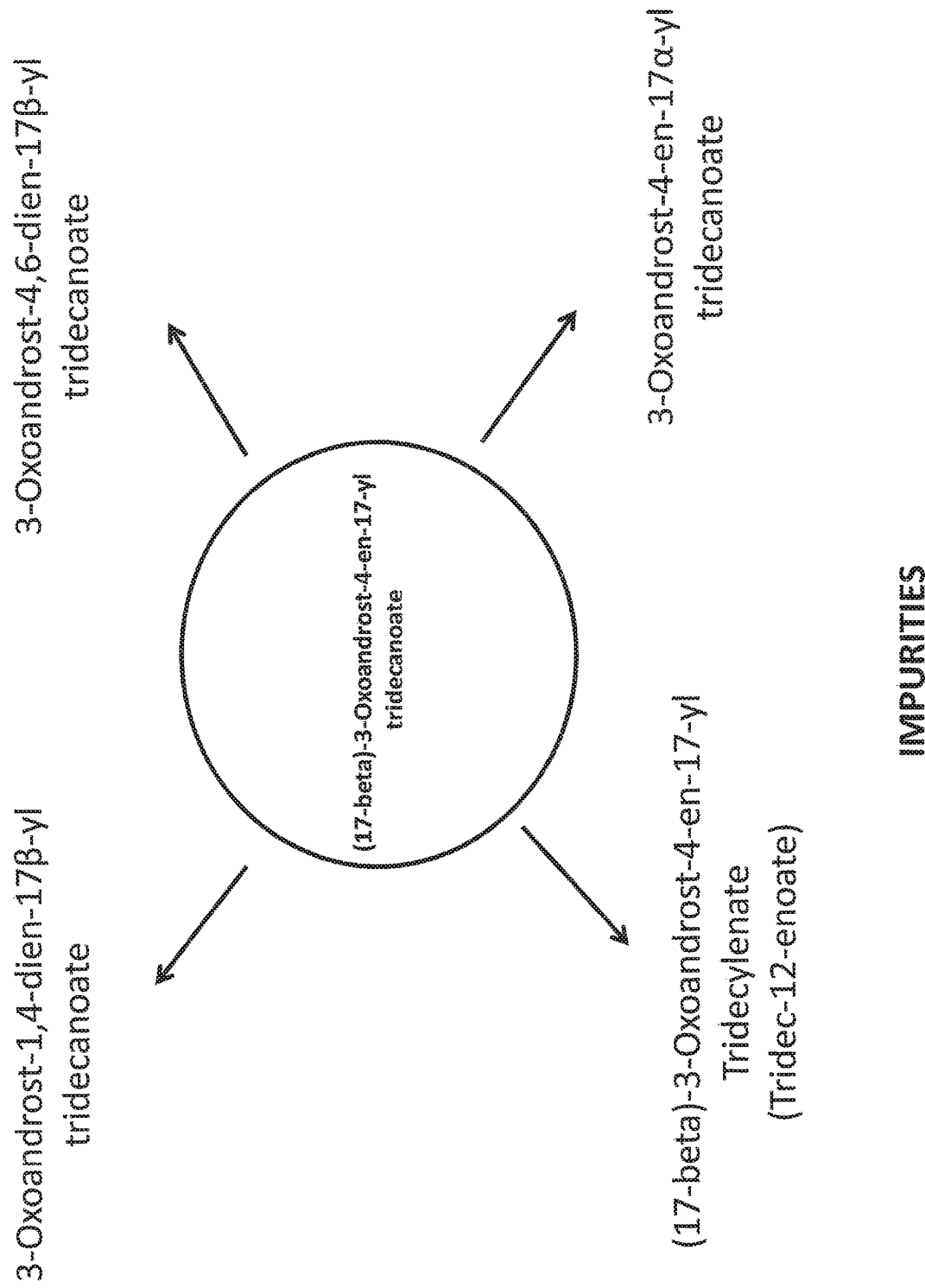
FIG. 4 shows a classification of potential impurities related to (17-β)-3-Oxoandrost-4-en-17-yl tridecanoate samples.
Figure 5:
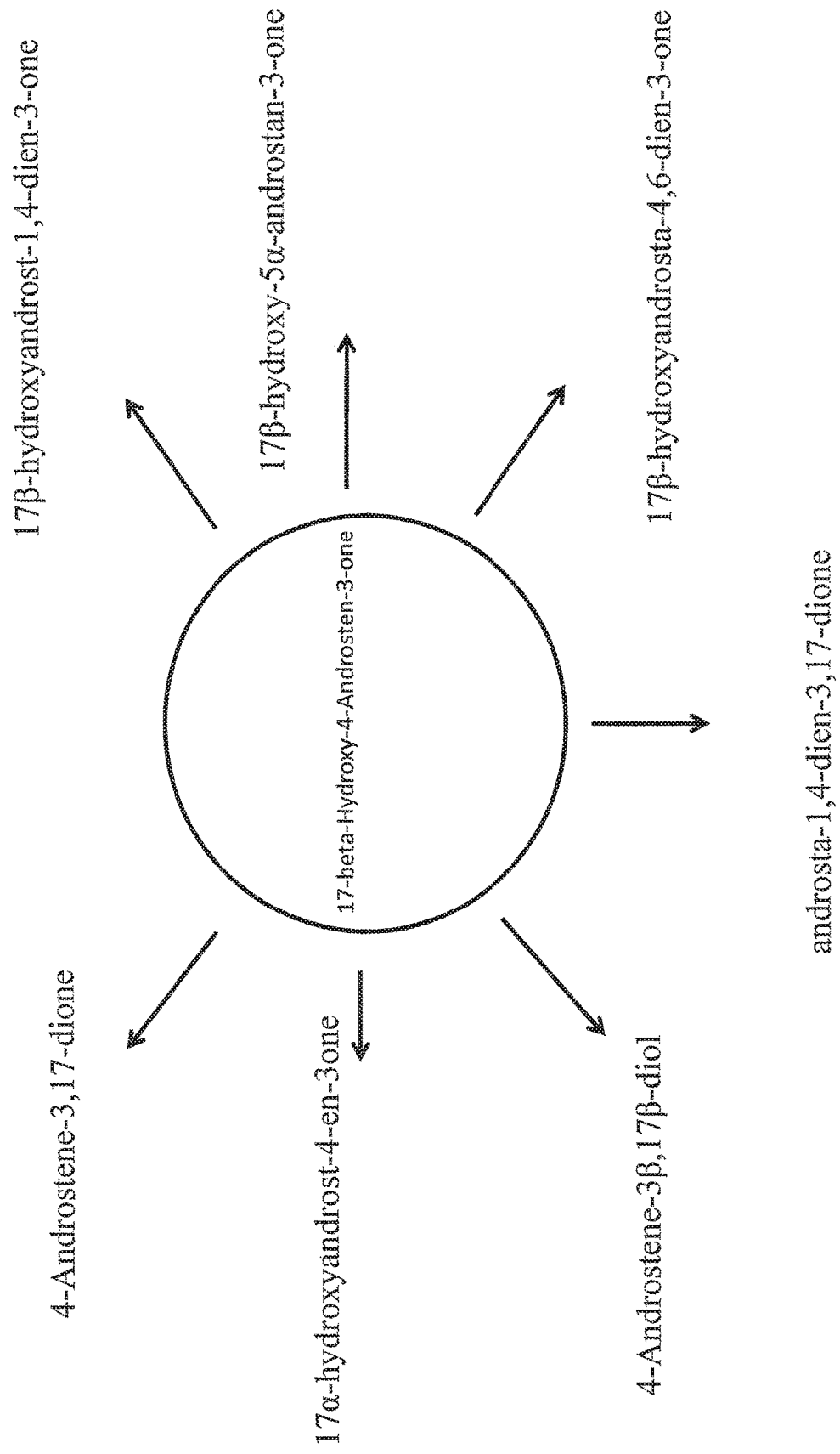
FIG. 5 shows a classification of potential impurities related to (17-β)-3-Oxoandrost-4-en-17-yl tridecanoate samples.

Provided herein are compositions containing (17-β)-3-Oxoandrost-4-en-17-yl tridecanoate substantially free of synthetic impurities. Synthetic impurities of compositions containing (17-β)-3-Oxoandrost-4-en-17-yl tridecanoate include, but are not limited to, residual solvents, unreacted reactants, unreacted impurities in reactants, reaction products of impurities in reactants, and impurities created during synthesis, work up, or both. See FIG. 3.

In one embodiment, a composition having substantially pure (17-β)-3-Oxoandrost-4-en-17-yl tridecanoate is provided. According to an aspect of this embodiment, the composition comprises at least 95% substantially pure (17-β)-3-Oxoandrost-4-en-17-yl tridecanoate. In a more specific aspect, the composition comprises at least 97% substantially pure (17-β)-3-Oxoandrost-4-en-17-yl tridecanoate. In another more specific aspect, the composition comprises at least 98% substantially pure (17-β)-3-Oxoandrost-4-en-17-yl tridecanoate. In another more specific aspect, the composition comprises at least 99% substantially (17-β)-3-Oxoandrost-4-en-17-yl tridecanoate. In another more specific aspect, the composition comprises at least 99.5% substantially pure (17-β)-3-Oxoandrost-4-en-17-yl tridecanoate. In a specific aspect, the API is a crystalline or amorphous powder. In one aspect, a substantially pure (17-β)-3-Oxoandrost-4-en-17-yl tridecanoate substantially free of synthetic impurity (A): 17-β-Hydroxy-4-Androsten-3-one or a synthetic reaction by-product thereof is provided. In one aspect, a substantially pure (17-β)-3-Oxoandrost-4-en-17-yl tridecanoate substantially free of synthetic impurity (B): tridecanoic acid, tridecanoate, tridecanoyl chloride or a non-API synthetic reaction by-product thereof is provided. In one aspect, a substantially pure (17-β)-3-Oxoandrost-4-en-17-yl tridecanoate substantially free of synthetic impurity (C): Ethanol, pyridine, heptanes, heptanes, or a combination thereof is provided. In one aspect, a substantially pure (17-β)-3-Oxoandrost-4-en-17-yl tridecanoate substantially free of synthetic impurity (D): (17-β)-3-Oxoandrost-4-en-17-yl undecanoate is provided. In one aspect, a substantially pure (17-β)-3-Oxoandrost-4-en-17-yl tridecanoate substantially free of synthetic impurity (E): (17-β)-3-Oxoandrost-4-en-17-yl decanoate is provided. In one aspect, a substantially pure (17-β)-3-Oxoandrost-4-en-17-yl tridecanoate substantially free of synthetic impurity (F): (17-β)-3-Oxoandrost-4-en-17-yl dodecanoate is provided. In one aspect, a substantially pure (17-β)-3-Oxoandrost-4-en-17-yl tridecanoate substantially free of synthetic impurity (E): (17-β)-3-Oxoandrost-4-en-17-yl tetradecanoate is provided. According to some aspect, substantially free of an impurity in this paragraph refers to less than 10%, 7%, 5%, 3%, 3%, 1%, 0.5%, 0.1%, 0.05%, or 0.01% of any specific impurity referred to this paragraph or their combined total. In a specific aspect, the sum total of all these Impurities (Synthetic Impurity A, B, C, D, or E) compared to the amount of (17-β)-3-Oxoandrost-4-en-17-yl tridecanoate in a sample as determined by HPLC (e.g., at about 240 nm or another appropriate wavelength) is no more than 20%, 15%, 10%, 5%, 4%, 3%, 7%, 1%, 0.75%, 0.50%, 0.25%, 0.20%. 0.10%, or 0.50%. In another specific aspect, the total of any one of these synthetic impurity A, B, C, D, or E as described above as compared to the amount of (17-β)-3-Oxoandrost-4-en-17-yl tridecanoate in a sample as determined by HPLC (e.g., at about 240 nm or 242 nm another appropriate wavelength) is no more than 2%, 1.5%, 1.0%, 0.50%, 0.40%, 0.30%, 0.20%, 0.10%, 0.075%, 0.050%, 0.025%, 0.020%, 0.010%, or 0.0050%.

Decomposition or Degradation
(17-β)-3-Oxoandrost-4-En-17-Yl Tridecanoate or Incompatibility Thereof with Carrier of the Composition or Related Impurities Provided herein are compositions containing substantially pure (17-β)-3-Oxoandrost-4-en-17-yl tridecanoate substantially free of decomposition impurities. Decomposition impurities of compositions containing (17-β)-3-Oxoandrost-4-en-17-yl tridecanoate include, but are not limited to, decomposition of (17-β)-3-Oxoandrost-4-en-17-yl tridecanoate in e.g., bulk (17-β)-3-Oxoandrost-4-en-17-yl tridecanoate, pharmaceutical compositions or formulations, or in unit dosage forms. Decomposition impurities include, but are not limited to impurities resulting from cleavage of the ester moiety, oxidation of functional groups on the steroid polycyclic core, dealkylation of the ester, etc. In some aspects, stabilized compositions are provided herein. Such stabilized compositions can be e.g., compositions stored under specific environmental conditions, have stabilizing agents (e.g., an antioxidant), or both. The stabilized composition can be (17-β)-3-Oxoandrost-4-en-17-yl tridecanoate, a composition such as a pharmaceutical composition comprising (17-β)-3-Oxoandrost-4-en-17-yl tridecanoate and a pharmaceutically acceptable carrier, a unit dosage form having (17-β)-3-Oxoandrost-4-en-17-yl tridecanoate and a pharmaceutically acceptable carrier and the such. In one embodiment, substantially pure (17-β)-3-Oxoandrost-4-en-17-yl tridecanoate is provided substantially free of Decomposition Impurity (1): (17-β-Hydroxy-4-Androsten-3-one. In one aspect, substantially pure (17-β)-3-Oxoandrost-4-en-17-yl tridecanoate is provided that is substantially free of Decomposition Impurity (2): hydroxylated at position 6 (out of the plane) of the FIG. 6. In one aspect, substantially pure (17-β)-3-Oxoandrost-4-en-17-yl tridecanoate is provided that is substantially free of Decomposition Impurity (3): hydroxylated at position 6 (in the plane) of the FIG. 6. In one aspect, a substantially pure (17-β)-3-Oxoandrost-4-en-17-yl tridecanoate substantially free of Decomposition Impurity (1), (2), or (3) or a combination thereof as described above is provided. In a specific aspect, the sum total of all these Decomposition Impurities (Decomposition Impurity 1, 2, and 3) compared to the amount of (17-β)-3-Oxoandrost-4-en-17-yl tridecanoate in a sample as determined by HPLC (e.g., at about 240 or 242 nm or another appropriate wavelength) is no more than 20%, 15%, 10%, 5%, 4%, 3%, 2%, 1%, 0.75%, 0.50%, 0.25%, 0.20%, 0.10%, or 0.50%. In another specific aspect, the total of any one of Decomposition Impurities (1), (2), and (3) described above as compared to the amount of (17-β)-3-Oxoandrost-4-en-17-yl tridecanoate in a sample as determined by HPLC (e.g., at about 240 or 242 nm or another appropriate wavelength) is no more than 2%, 1.5%, 1.0%, 0.50%, 0.40%, 0.30%, 0.20%, 0.10%, 0.075%, 0.050%, 0.025%, 0.020%, 0.010%, or 0.0050%. In one aspect, substantially pure (17-β)-3-Oxoandrost-4-en-17-yl tridecanoate substantially free of related compound (RC) impurity 1, 2, 3, 4, 5, 6, 7, 8, 9, 10, or 11 as identified in Example 5 (see e.g., FIGS. 13-15). In a specific aspect, the sum total of all these impurities compared to the amount of (17-β)-3-Oxoandrost-4-en-17-yl tridecanoate in a sample as determined by HPLC (e.g., at about 240 or 242 nm or another appropriate wavelength) is no more than 20%, 15%, 10%, 5%, 4% 3%, 2%, 1%, 0.75%, 0.50%, 0.25%, 0.20%, 0.10%, or 0.50%, In another specific aspect, the total of any one of these impurities (e.g., RC impurity 1, 2, 3, 4, 5, 6, 7, 8, 9, 10, or 11) as identified in Example 5 (see e.g., FIGS. 13-15)) compared to the amount of (17-β)-3-Oxoandrost-4-en-17-yl tridecanoate in a sample as determined by HPLC (e.g., at about 240 nm or another appropriate wavelength) is no more than 2%, 1.5%, 1.0%, 0.50%, 0.40%, 0.30%, 0.20%, 0.10%, 0.075%, 0.050%, 0.025%, 0.020%, 0.010%, or 0.0050%.

Determination of Impurities and Potency

Impurities in the composition can be determined by any method suitable for identifying such impurities. Typical methods for determining impurities depend on the nature of the starting composition. For example, techniques suitable for examining bulk (17-β)-3-Oxoandrost-4-en-17-yl tridecanoate may be different or involve different condition as compared to examining impurities in a pharmaceutical composition or unit dosage form. The potency of bulk API, pharmaceutical compositions or unit dosage forms may also be determined via some of these techniques. Exemplary, non-limiting techniques are described in more detail below.

High Performance Liquid Chromatography (HPLC)

HPLC is a technique commonly used to identify impurities or levels thereof in substances (and may also be used to determine potency). HPLC can be used to quantitatively or to qualitatively assess impurities in samples (e.g., bulk (17-β)-3-Oxoandrost-4-en-17-yl tridecanoate or a composition containing (17-β)-3-Oxoandrost-4-en-17-yl tridecanoate) and potency. HPLC methods can also be used for assessing the potency of a particular sample. The ordinary skilled artisan is familiar with and capable of performing HPLC techniques. Typically, a chromatogram from known standard samples is compared to that of an unknown sample. The purity of the unknown can be estimated by comparing the area under the curve for the peak that corresponds to (17-β)-3-Oxoandrost-4-en-17-yl tridecanoate to other peaks in the chromatogram. Several appropriate HPLC techniques are described in the Examples. Other methods can be adapted to analyze purity or impurities of the compositions described herein (See e.g., Gonzalo-Lumbreras, et al, J. Pharm. Biomed. Anal. Volume 38, Issue 4, 15 Jul. 2005, Pages 757-762, Pozo et al. Biomed. Chrom. Volume 23, Issue 8, pages 873-880, August 2009).

Nuclear Magnetic Resonance (NMR)

NMR is a technique commonly used to identify impurities or levels thereof in substances and potency. NMR can be used to quantitatively or to qualitatively assess impurities in samples (e.g., bulk (17-β)-3-Oxoandrost-4-en-17-yl tridecanoate or a composition containing (17-β)-3-Oxoandrost-4-en-17-yl tridecanoate) and potency. NMR methods can also be used for assessing the potency of a particular sample. The ordinary skilled artisan is familiar with and capable of performing NMR techniques. Typically, proton NMR, $^{13}$C NMR, or both are used for assessing (17-β)-3-Oxoandrost-4-en-17-yl tridecanoate compositions for purity or potency (quantitative NMR). Webster et al. Appl Spectrosc. 2010 May; 64(5):537-42.

Other techniques are also useful for analyzing (17-β)-3-Oxoandrost-4-en-17-yl tridecanoate for purity and potency such as x-ray powder diffraction, mass spectrometry, fourier-transform infrared spectroscopy, raman spectroscopy, etc. See Bugay Adv Drug Deliv Rev. 2001 May 16; 48(1): 43-65.

Stabilized Compositions

Stabilized compositions are provided herein. Instability of bulk (17-β)-3-Oxoandrost-4-en-17-yl tridecanoate and composition containing (17-β)-3-Oxoandrost-4-en-17-yl tridecanoate can result in undesirable changes in performance (e.g., dissolution or bioavailability), changes in physical appearance, product failures, safety, toxicity, etc. Stabilization of compositions having (17-β)-3-Oxoandrost-4-en-17-yl tridecanoate depends on the nature of the composition and the nature of what type of stabilization is desired. For example, stabilization of bulk (17-β)-3-Oxoandrost-4-en-17-yl tridecanoate may involve a specific set of conditions ("stabilizing condition") e.g., storage and handling conditions that are different (although not necessarily) than for a pharmaceutical composition or a unit dosage form. Furthermore, stabilization of certain compositions can involve preventing or mitigating certain things in one composition whereas those same certain things may be desirable in another composition. For example, crystalline substantially pure and substantially free of impurity (17-β)-3-Oxoandrost-4-en-17-yl tridecanoate may be desirable for stabilization of (17-β)-3-Oxoandrost-4-en-17-yl tridecanoate, whereas in other compositions like a pharmaceutical compositions or unit dosage forms crystalline (17-β)-3-Oxoandrost-4-en-17-yl tridecanoate may not be desirable.

Thus, in one embodiment, substantially pure (17-β)-3-Oxoandrost-4-en-17-yl tridecanoate is provided that is stabilized. In one aspect of this embodiment, the stabilized substantially pure (17-β)-3-Oxoandrost-4-en-17-yl tridecanoate is stabilized by its high degree of purity in solid form (e.g., crystalline, amorphous, or a combination thereof). In one aspect, the (17-β)-3-Oxoandrost-4-en-17-yl tridecanoate is recrystallized from a solvent. In one aspect, the (17-β)-3-Oxoandrost-4-en-17-yl tridecanoate is recrystallized from a solvent which is an alcohol, alkane, oil, fatty acid or other solvent. In one aspect, the (17-β)-3-Oxoandrost-4-en-17-yl tridecanoate is recrystallized from a solvent which is an alcohol, alkane, oil, fatty acid or other solvent to provide substantially pure stabilized (17-β)-3-Oxoandrost-4-en-17-yl tridecanoate pharmaceutical ingredient. In another aspect, the substantially pure (17-β)-3-Oxoandrost-4-en-17-yl tridecanoate is stabilized in a composition e.g., pharmaceutical composition or unit dosage form that has a stabilizing agent. In a specific aspect, the stabilizing agent is an antioxidant. In another specific aspect, the stabilizing agent is ascorbate or a derivative thereof. In another specific aspect, the stabilizing agent is a fatty acid ester of ascorbate. In another specific aspect, the stabilizing agent is ascorbyl palmitate. In some aspects, compositions are provided (e.g., pharmaceutical composition, formulation or unit dosage form) having or prepared from substantially pure (17-β)-3-Oxoandrost-4-en-17-yl tridecanoate and ascorbyl palmitate. In one aspect of this embodiment, the stabilized substantial pure (17-β)-3-Oxoandrost-4-en-17-yl tridecanoate is substantially free of impurities.

In certain embodiments, the pharmaceutical compositions are substantial free of iodine or peroxides. For example, in some embodiments the pharmaceutical composition or components from which it is prepared have a peroxide of less than 100, 90, 80, 70, 60, 50, 40, 30, 25, 20, 15, 10 or 5.

Bulk API can also be stabilized by maintaining the substantially pure (17-β)-3-Oxoandrost-4-en-17-yl tridecanoate under stabilizing conditions which include, but are not limited to, temperature (e.g., less than 0, 5, 10, 15, 20, 25, 30, 35, 40, 45, 50, 55, 60° C.); relative humidity (e.g., less than 90, 80, 70, 60, 50, 40, 30, 20, 10 or 5%); light (e.g., controlling or minimizing exposure to light including UV, visible, or IR light); and oxidation (e.g., preventing or minimizing exposure to oxidizing agents or oxidizing conditions). In one aspect, bulk substantially pure (17-β)-3-Oxoandrost-4-en-17-yl tridecanoate in an amount of greater than 1 g, 5 g, 10 g, 50 g, 100 g, 500 g, 1 kg, 5 kg, 10 kg, 50 kg, 100 kg, 500 kg, 1000 kg, 5000 kg, or 10,000 kg is maintained under stabilizing conditions. In an aspect, the substantially pure (17-β)-3-Oxoandrost-4-en-17-yl tridecanoate is crystalline API. In a related aspect, methods of stabilizing (17-β)-3-Oxoandrost-4-en-17-yl tridecanoate are also provided herein. The method can depend on the composition (e.g., bulk substantially pure (17-β)-3-Oxoandrost-4-en-17-yl tridecanoate, pharmaceutical composition, formulation, or unit dosage form) that is to be stabilized. In one aspect, the method comprises storing substantially pure (17-β)-3-Oxoandrost-4-en-17-yl tridecanoate under conditions that prevent decomposition of the (17-β)-3-Oxoandrost-4-en-17-yl tridecanoate. According to a specific aspect, the condition is high purity (e.g., greater than 95%, greater than 98% or greater than 99% by total weight of the composition), maintaining the composition at a temperature of less than 60° C., less than 50° C., less than 40° C., less than 30° C., less than 20° C., less than 15° C., less than 10° C., less than 5° C., or less than 0° C., maintaining the composition in a non-oxidizing environment or minimal oxidizing environment. In yet another aspect, the method of stabilizing comprises combining (17-β)-3-Oxoandrost-4-en-17-yl tridecanoate with a carrier or agent (e.g., fatty acid ester of ascorbate (i.e., ascorbyl palmitate)) that prevents or minimizes decomposition of (17-β)-3-Oxoandrost-4-en-17-yl tridecanoate. These methods are suitable for providing substantially pure (17-β)-3-Oxoandrost-4-en-17-yl tridecanoate or a unit dosage form or pharmaceutical composition prepared from or comprising (17-β)-3-Oxoandrost-4-en-17-yl tridecanoate wherein there is less than 5%, 2%, or 1% total API related impurities after storage for a period of time of 1, 2, 3, 4, 5, 6, 7, 8, 9, 10, 12, 15, 17, 20, 25, or 30 months or longer. According to some aspects, the composition has a potency of 100% or 99.5% or more, 99% or more, 98% or more, 97% or more, 95% or more, or 90% or 80% or more after storage for a period of time. According to some aspects, the composition has a purity of 100% or 99.5% or more, 99% or more, 98% or more, 97% or more, 95% or more, or 90% or more after storage for a period of time.

Injectable Composition (e.g., Parenteral Composition or Subcutaneous) and Method of Use In one embodiment, a pharmaceutical composition is provided which is an injectable composition (e.g., for parenteral or subcutaneous administration) which comprises or is prepared from substantially pure (17-β)-3-Oxoandrost-4-en-17-yl tridecanoate and a pharmaceutically acceptable carrier. Associated methods of employing the composition are provided. For the treatment or prevention of a disease, disorder or a condition (e.g., hypogonadism). In one aspect, the substantially pure (17-β)-3-Oxoandrost-4-en-17-yl tridecanoate is substantially free of impurities.

In one embodiment, the composition and method relate to a depot or depot injection. A number of parameters influence the pharmacokinetic profile of substantially pure (17-β)-3-Oxoandrost-4-en-17-yl tridecanoate that is injected intramuscularly as a depot. A depot effect is achieved with substantially pure (17-β)-3-Oxoandrost-4-en-17-yl tridecanoate that slowly degrades (e.g., is de-esterified) into 17-β-Hydroxy-4-Androsten-3-one once it has entered into circulation. Another factor contributing to the depot effect is the diffusion rate of the substantially pure (17-β)-3-Oxoandrost-4-en-17-yl tridecanoate from the site of injection to the circulatory system. The diffusion rate can depend on the dose and the volume injected in that the concentration gradient of the substantially pure (17-β)-3-Oxoandrost-4-en-17-yl tridecanoate at the site of administration is thought to affect the diffusion rate. Furthermore, the type of vehicle injected together with substantially pure (17-β)-3-Oxoandrost-4-en-17-yl tridecanoate can influence the rate of diffusion of substantially pure (17-β)-3-Oxoandrost-4-en-17-yl tridecanoate from the vehicle into the surrounding tissues and the rate of absorption into the blood circulation. The partition coefficient (n-octanol-water partition coefficient) of the substantially pure (17-β)-3-Oxoandrost-4-en-17-yl tridecanoate in the vehicle as well as the viscosity of the vehicle can be considered for adapting a depot effect following intramuscular injection of substantially pure (17-β)-3-Oxoandrost-4-en-17-yl tridecanoate.

Thus, in one embodiment, the substantially pure (17-β)-3-Oxoandrost-4-en-17-yl tridecanoate is dissolved in a vehicle.

In one embodiment, a depot effect in vivo with of substantially pure (17-β)-3-Oxoandrost-4-en-17-yl tridecanoate, is provided by injecting intramuscularly the substantially pure (17-β)-3-Oxoandrost-4-en-17-yl tridecanoate in a vehicle comprising an oil (e.g., castor oil) and optionally a suitable co-solvent. In one aspect, the co-solvent may lower the viscosity of the castor oil and then solve the problem with high viscosity of the castor oil when being injected, although the co-solvent may increase the diffusion rate of the substantially pure (17-β)-3-Oxoandrost-4-en-17-yl tridecanoate, resulting in a lower depot effect following intramuscular injection. Thus, careful selection of the co-solvent and amounts is an important consideration. In one aspect, the (17-β)-3-Oxoandrost-4-en-17-yl tridecanoate is substantially free of impurities.

Thus, in one embodiment, a composition comprising substantially pure (17-β)-3-Oxoandrost-4-en-17-yl tridecanoate; and an oil vehicle (e.g., castor oil) comprising and a co-solvent.

In one embodiment, the composition is formulated for parenteral administration, preferably intramuscular injection. Alternatively, the composition is formulated for subcutaneous injection.

The term "castor oil" is meant to encompass castor oil refined for injectable (e.g., parenteral) use. It should also be understood that the castor oil are not hydrogenated or at least in part not hydrogenated. In some embodiments, some of the double bonds may be hydrogenated. For example, less than 20% w/w of the double bonds are hydrogenated. In one aspect, less than 10% w/w of the double bonds are hydrogenated, less than 5% w/w, less than 2% w/w, less than 1% w/w of the double bonds are hydrogenated.

Co-solvent(s) can be defined by the capability of reducing the viscosity of the oil (e.g., castor oil), as determined by a Doppler viscosimeter.

Injection of viscous vehicles, such as castor oil, is associated with technical limitations to the size of cannula due to the resistance of the vehicle when passing the cannula. In one aspect, the viscosity of an injection solution is below 100 mPas. In certain aspects, the viscosity of a final product, ready to be injected, such as a re-constituted product is, e.g., less than 100 mPas, such as 90 mPas, 80 mPas, 70 mPas at room temperature. In some aspects, the viscosity of the vehicle is less than 60 mPas, 50 mPas, 40 mPas or 30 mPas at room temperature.

Thus, some embodiments relate to those wherein the co-solvent is selected from those that when being mixed with castor oil in an oil:co-solvent volume ratio of between 1:0.2 to 1:3, the viscosity drops from 950-1100 mPas to 20 mPas at room temperature. In one aspect, the co-solvent is selected from those, wherein the viscosity drops from 950-1100 mPas to about 80-100 mPas, when the co-solvent is being mixed with castor oil in an oil:co-solvent volume ratio of about 1:1 to 1:3. The viscosity of the vehicle can be determined with a Floppier type viscometer. The viscosity is measured at a fixed temperature, often room temperature such as 20° C. or 25° C. The co-solvent can be characterized by its ability to reduce the viscosity of a vehicle, such as castor oil, of the solvent in a ratio dependent manner.

In one embodiment, the viscosity of a mixture of castor oil and a co-solvent in a volume ratio of 1:0.1 to 1:1.7 is reduced from 60% to 5% of that of castor oil alone.

In another embodiment, the viscosity of a mixture of castor oil and a co-solvent is in a ratio of 1:0.02 by volume and is reduced by about 10% relatively to the viscosity of castor oil. In other aspects, when the ratio between the oil and co-solvent is 1:0.04 by volume the viscosity is reduced by 20% relatively to the viscosity of castor oil, when the ratio is of 1:0.08 by volume the viscosity is reduced by 25%, when the ratio is of 1:0.1 by volume the viscosity is reduced by 40%, when the ratio is of 1:0.2 by volume the viscosity is reduced by 50%, when the ratio is 1:0.35 by volume the viscosity is reduced by 75%, when the ratio is of 1:0.5 by volume the viscosity is reduced by 80%, when the ratio is of 1:1 by volume the viscosity is reduced by 90%, or when the ratio is 1:1.6 by volume the viscosity is reduced by 95%.

In further embodiments, the viscosity of the composition is below 100 mPas. In some aspects, the viscosity of vehicle, such as the mixture of castor oil and a co-solvent, such as benzyl benzoate is below 90 mPas, the viscosity of the vehicle is about 60-100 mPas, 70 to 100 mPas, or 80-90 mPas at room temperature (20° C. to 25° C.).

The viscosity of the injected vehicle may dictate to a certain extent the pharmacokinetic profile of an injected substance. Thus, in order to obtain a final product with a suitable depot effect in vivo, the castor oil and co-solvent, in some aspects, is in a volume ratio ranging between 1:0.2 to 1:3, between 1:0.5 to 1:3, or between 1:0.75 to 1:2.5. In one aspect, the volume ratio is in the range from 1:1 to 1:2.

In some embodiments, the co-solvent is benzyl benzoate. Other types of co-solvents are applicable for use in combination with the oil (e.g., castor oil), for example ethanol or benzyl alcohol. In one aspect, co-solvents are those which are capable of dissolving the substantially pure (17-β)-3-Oxoandrost-4-en-17-yl tridecanoate and is miscible with castor oil. Co-solvents suitable for dissolving about 100-500 mg, such as 250 mg of substantially pure (17-β)-3-Oxoandrost-4-en-17-yl tridecanoate in 1 mL of the co-solvent within 50 minutes at 40° C. or within 20 minutes at 60° C. are useful in some aspects.

The solubility of the substantially pure (17-β)-3-Oxoandrost-4-en-17-yl tridecanoate can be affected upon adding a co-solvent to the oil (e.g., castor oil) vehicle. In one aspect, the solubility may be improved. Thus, in some embodiments, the substantially pure (17-β)-3-Oxoandrost-4-en-17-yl tridecanoate is completely dissolved in the composition (vehicle with co-solvent(s)), and in other embodiments the substantially pure (17-β)-3-Oxoandrost-4-en-17-yl tridecanoate is partly dispersed in the composition. In one aspect, the substantially pure (17-β)-3-Oxoandrost-4-en-17-yl tridecanoate is fully dissolved in the vehicle. In one aspect, no particles of (17-β)-3-Oxoandrost-4-en-17-yl tridecanoate are detected by X-ray diffraction analysis of the composition comprising (17-β)-3-Oxoandrost-4-en-17-yl tridecanoate and vehicle.

Provided herein are compositions, wherein the co-solvent is present in the vehicle at concentrations ranging from 10 to 90 volume % ("v %"). In one aspect, the concentration of the co-solvent in the vehicle ranges between 15 to 85 v %, between 20 to 80 v %, such as between 45 to 85 v % or 55 to 85 v %.

In one embodiment, the vehicle comprises a plant oil (e.g., castor oil) in a volume concentration ranging between 20 to 85 v %. In one aspect, the concentration of castor oil in the vehicle ranges between 25 to 60 v % or 25 to 55 v %. In some aspects, the concentration of castor oil in the vehicle ranges between 25 to 50 v %, 25 to 45 v % or 25 to 40 v %.

In some embodiments, the composition does not comprise another plant oil, e.g., tea seed oil. In one aspect, the only plant oil present in the composition is castor oil or that castor oil is at least 50% by volume of the total content of the plant oil in the vehicle, e.g., at least 60%, 70%, 80% or 90% by volume.

The selection of a co-solvent depends on a number of factors, such as i) the amount of (17-β)-3-Oxoandrost-4-en-17-yl tridecanoate in the injection vehicle, ii) the required reduction of viscosity and iii) the release properties of the injection vehicle with respect to the (17-β)-3-Oxoandrost-4-en-17-yl tridecanoate at the site of injection (diffusion rate). In some aspects, the co-solvent is at least 10 v % of the vehicle, at least 15 v %, at least 25 v %, least 40 v %, or at least 50 v %. In some aspects, the co-solvent is in an amount ranging from about 40 to 80 v % of the vehicle, 50 to 70 v %, or 55 to 65 v % of the vehicle.

In one embodiment, the concentration of the co-solvent in the vehicle is chosen to reduce the diffusion rate of the substantially pure (17-β)-3-Oxoandrost-4-en-17-yl tridecanoate, for instance at the site of injection. Therefore in some aspects, the concentration of co-solvent in the vehicle is less than 90 v %, less than 85 v %, less than 80 v %, or less than 75 v %.

In one embodiment, the volume injected intramuscularly is chosen to affect the release rate of the substantially pure (17-β)-3-Oxoandrost-4-en-17-yl tridecanoate from the vehicle. In one aspect, an injection volume of 5 mL is provided for administration by one single intramuscular injection to one injection site. If an intramuscular injection of a volume greater than 5 mL is required, the injection volume can be divided into two or more separate injections to different injection sites. In one aspect, the injection volume is 4-5 mL or less, 3-4 mL or less, 2-3 mL or less, 1-2 mL or less, or 1 mL or less.

A single dose to one injection site offers advantages in controlling the release rate of an active principle, rather than multiple injections of divided single doses. Thus, in some embodiments, an injection scheme wherein a single dose of substantially pure (17-β)-3-Oxoandrost-4-en-17-yl tridecanoate is divided into no more than two separate injections to one or more injection sites is provided. In one aspect, a single dose of substantially pure (17-β)-3-Oxoandrost-4-en-17-yl tridecanoate is injected as one single injection to one injection site, Therefore, in one aspect, the dose of the substantially pure (17-β)-3-Oxoandrost-4-en-17-yl tridecanoate is administered as a single injection to one injection site, wherein the injected volume is from 1 to 5 mL, of 1 to 4 mL, or 1.5 to 4 mL. Suitable injection volumes for ensuring reproducible administration volumes and uniform release of the substantially pure (17-β)-3-Oxoandrost-4-en-17-yl tridecanoate is lower than 5 mL, e.g., about 5 mL, about 4 mL, about 3 mL, about 2 mL and about 1 mL.

In order for using single injections and low injection volumes, the concentration of the substantially pure (17-β)-3-Oxoandrost-4-en-17-yl tridecanoate in the compositions can be relatively high. Thus, the substantially pure (17-β)-3-Oxoandrost-4-en-17-yl tridecanoate is in a concentration of 50 mg to 1000 mg per mL of the vehicle. Thus, in some aspects, the substantially pure (17-β)-3-Oxoandrost-4-en-17-yl tridecanoate is in a concentration of 100 to 750 mg per mL of the vehicle, 150 to 500 mg per mL, 175 to 400 mg per mL, or about 250 mg/mL of the vehicle.

The composition, in some aspects, is formulated as a unit dose form such as a unit dose for injection as one single dose. In some embodiments, the substantially pure (17-β)-3-Oxoandrost-4-en-17-yl tridecanoate is in a dose of 500 to 4000 mg, 500 mg to 3000 mg, 750 mg to 2000 mg, 750 mg to 1500 mg, or about 250 mg, about 500 mg, about 750 mg or about 1000 mg.

The injectable compositions can further comprise another therapeutically active agent, such as a progestin and/or a further gonadotropin suppressive agent other than (17-β)-3-Oxoandrost-4-en-17-yl tridecanoate.

The compositions some embodiments (e.g., injectable) are chemically stable with respect to the substantially pure (17-β)-3-Oxoandrost-4-en-17-yl tridecanoate. For example, in some aspects, degradation products are not detected after long term storage (such as after 7 weeks, 10 weeks or 17 weeks or even longer) at conditions normally known to accelerate degradation processes, such as variations in temperatures, high and low temperatures and various relative humidity. For example, less than 1% by weight of degradation products of substantially pure (17-β)-3-Oxoandrost-4-en-17-yl tridecanoate is present after storage of the composition for at least 7 weeks, such as for 16 or 17 weeks, for 6 months, or for 9 or 12 months at 40° C. and 25% r.h. (relative humidity) in darkness. In one aspect, less than 0.5% w/w, such as less than 0.2% w/w of degradation products of substantially pure (17-β)-3-Oxoandrost-4-en-17-yl tridecanoate is present after storage at the above-mentioned conditions.

Oral Pharmaceutical Compositions Having Substantially Pure (17-β)-3-Oxoandrost-4-en-17-yl Tridecanoate The pharmaceutical compositions and dosage forms (e.g. capsule or tablet) described herein prepared from or comprising substantially pure (17-β)-3-Oxoandrost-4-en-17-yl tridecanoate (as described in the embodiments above) can include a variety of pharmaceutically acceptable carriers or additives known in the art. Non-limiting examples of components that can be included as components of the pharmaceutical carrier include lipophilic surfactants, hydrophilic surfactants, triglycerides, fatty acid (C8 to C22), fatty acid glycerides (mono-, di-, tri-, or a combination thereof), or a combination thereof.

In one embodiment, the pharmaceutical composition or dosage form comprises, or is prepared with, substantially pure (17-β)-3-Oxoandrost-4-en-17-yl tridecanoate as described herein.

In one embodiment, the pharmaceutical composition or unit dosage form is characterized by its dissolution or release profile (e.g., at least 75% in 4 hours). In one aspect, the oral pharmaceutical composition or unit dosage form can be formulated as a tablet or capsule (e.g., hard gel or soft gel). According to this embodiment, a pharmaceutical composition or unit dosage form having a particular amount of substantially pure (17-β)-3-Oxoandrost-4-en-17-yl tridecanoate (e.g., 3 mg or more, 4 mg or more, 5 mg or more, 10 mg or more, 15 mg or more, 20 mg or more, 30 mg or more, 40 mg or more, 50 mg or more, 75 mg or more, 100 mg or more, 125 mg or more, 150 mg or more, 175 mg or more, 200 mg or more, 225 mg or more, 250 mg or more, 275 mg or more, or 300 mg or more).

In one embodiment, the pharmaceutical composition or unit dosage form having (or prepared from) substantially pure (17-β)-3-Oxoandrost-4-en-17-yl tridecanoate has a release profile (e.g., a profile comprising 2, 3, 4, 5, or 6 or more time points each at least 5, 10, or 15 minutes apart or a single time point) of (17-β)-3-Oxoandrost-4-en-17-yl tridecanoate that does not change substantially as a function of storage time using a USP type 2 apparatus in about 1000 mL 8% Triton X100 solution in water at a specific temperature (e.g., 20.0, 37.0 or 40.0° C. (±0.5)) at 100 rpm. In one aspect, the release profile does not substantially change over a period of 1, 2, 3, 4, 5, 6, 7, 8, 9, 10, 11, 12, 13, 14, 15, or 16 weeks. In one aspect, the release profile does not substantially change over a period of 1, 2, 3, 4, 5, 6, 7, 8, 9, 10, 11, 12, 13, 14, 15, or 16 months.

In one embodiment, the pharmaceutical composition or unit dosage form having (or prepared from) substantially pure (17-β)-3-Oxoandrost-4-en-17-yl tridecanoate has a release profile (e.g., a profile comprising 2, 3, 4, 5, or 6 or more time points each at least 5, 10, or 15 minutes apart or a single time point) of (17-β)-3-Oxoandrost-4-en-17-yl tridecanoate using a USP type 2 apparatus in about 1000 mL 8% Triton X100 solution in water at a specific temperature (e.g., 20.0, 37.0 or 40.0° C. (±0.5)) at 100 rpm that release at least 10, 20, 30, 40, 50, 60, 70, 75, 80, 85, 90, 95, 96, 97, 98, or 99% at 15, 20, 30, 40, 45, 50, 60, 90, 120, 180, 240, or 300 minutes.

In one embodiment, the pharmaceutical composition or unit dosage form having (or prepared from) substantially pure (17-β)-3-Oxoandrost-4-en-17-yl tridecanoate has a release profile (e.g., a profile comprising 2, 3, 4, 5, or 6 or more time points each at least 5, 10, or 15 minutes apart or a single time point) of (17-β)-3-Oxoandrost-4-en-17-yl tridecanoate using a USP type 2 apparatus in about 1000 mL 8% Triton X100 solution in water at a specific temperature (e.g., 20.0, 37.0 or 40.0° C. (±0.5)) at 100 rpm that release less than 10, 20, 30, 40, 50, 60, 70, 75, 80, 85, 90, 95, 96, 97, 98, or 99% at 15, 20, 30, 40, 45, 50, 60, 90, 120, 180, 240, or 300 minutes.

In some embodiments, the pharmaceutically acceptable carrier of the composition (e.g., pharmaceutical composition, formulation or unit dosage form) can include a lipophilic additive. In some embodiments, the lipophilic additive can comprise at least about 10, 20, 30, 40, 50, 60, 70, 80, 90 or 95 wt % of the pharmaceutically acceptable carrier. Non-limiting examples of lipophilic additives can include lipophilic surfactants, triglycerides, tocopherol, tocopherol derivatives and combinations thereof. In one embodiment, the lipophilic additive can include a fatty acid or fatty acid glyceride. In another embodiment, lipophilic additive can include the fatty acid glyceride, and the fatty acid glyceride can be a monoglyceride, a diglyceride, or mixtures thereof. In one aspect, the fatty acid is oleic acid, stearic acid or a combination thereof. In one aspect, the fatty acid glyceride is glyceryl palmitostearate. Non-limiting examples of fatty acid glycerides that can be used in the oral pharmaceutical compositions and dosage forms of the present invention include monoglycerides and/or diglycerides derived from sources such as maize oil, poppy seed oil, safflower oil, sunflower oil, borage seed oil, peppermint oil, coconut oil, palm kernel oil, castor oil, and mixtures thereof. In one embodiment, the pharmaceutical composition or dosage form thereof comprises 50%, 40%, 30%, 20%, 15%, 10%, 5% by weight or less of a triglyceride. In a specific embodiment, the pharmaceutical composition or dosage form thereof, comprises less than 50% by weight of castor oil. In another embodiment, the composition includes 10 wt % or less of triglycerides. In a further embodiment, the composition includes 5 wt % or less of triglycerides. In a still a further embodiment, the composition includes about 3 wt % or less of triglycerides. In still a further embodiment, the composition includes about 1 wt % or less of triglycerides. In another embodiment, the composition is free or substantially free of triglycerides. In another embodiment, the composition and dosage forms are free of phytosterols and phytosterol fatty acid esters.

In another embodiment, the lipophilic additive can include a lipophilic surfactant. As used herein a surfactant is considered to be a lipophilic surfactant when it has an HLB value of 10 or less. Various lipophilic surfactants can be used including, but not limited to mono-, diglycerides of fatty acids like glyceryl monolinoleate (e.g. Maisine® 35-1), mono- and di glycerides of caprylic, capric acid (e.g. Capmul® MCM), glyceryl monooleate, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g. Labrafil® M 2125 CS), PEG-6 almond oil (e.g. Labrafil®M 1966 CS), PEG-6 apricot kernel oil (e.g. Labrafil®M 1944 CS), PEG-6 olive oil (e.g. Labrafil®M 1980 CS), PEG-6 peanut oil (e.g. Labrafil®M 1969 CS), PEG-6 hydrogenated palm kernel oil (e.g. Labrafil®. M 2130 BS), PEG-6 palm kernel oil (e.g. Labrafil® M 2130 CS), PEG-6 triolein (e.g. Labrafil® M 2735 CS), PEG-8 corn oil (e.g. Labrafil® WL 2609 BS), PEG-20 corn glycerides (e.g. Crovol® M40), PEG-20 almond glycerides (e.g. Crovol® A40), lipophilic polyoxyethylene-polyoxypropylene block co-polymers (e.g. Pluronic® L92, L101, L121 etc.); propylene glycol fatty acid esters, such as propylene glycol monolaurate (e.g. Lauroglycol FCC), propylene glycol ricinoleate (e.g. Propymuls), propylene glycol monooleate (e.g. Myverol P-O6), propylene glycol dicaprylate/dicaprate (e.g. Captex® 200), and propylene glycol dioctanoate (e.g. Captex® 800), propylene glycol monocaprylate (e.g. Capryol® 90); propylene glycol oleate (e.g. Lutrol OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g. Arlacel® 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g. Arlacel 20), sorbitan monopalmitate (e.g. Span-40), sorbitan monooleate (e.g. Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, and the like, and mixtures thereof. It is important to note that some lipophilic surfactants may also function as the solubilizer component of the compositions and oral dosage forms.

In one embodiment, the lipophilic surfactant can be selected from the group consisting of glyceryl monolinoleate (e.g. Maisine® 35-1), mono- and di glycerides of caprylic, capric acid (e.g. Capmul® MCM), glyceryl monooleate, propylene glycol mono caprylate, propylene glycol oleate, propylene glycol monostearate, propylene glycol monolaurate, propylene glycol mono-oleate, propylene glycol dicaprylate/dicaprate, sorbitan monooleate, PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, sorbitan monolaurate (e.g. Arlacel 20), sorbitan monopalmitate, sorbitan monooleate, sorbitan monostearate, sorbitan tristearate, sorbitan monolaurate, sorbitan monopalmitate, sorbitan monooleate, sorbitan trioleate, sorbitan sesquioleate, sorbitan tristearate, sorbitan monoisostearate, and combinations thereof. In some embodiments, the lipophilic surfactants can comprise at least about 10, 20, 30, 40, 50, 60, 70, 80, 90 or 95 wt % of the total pharmaceutically acceptable carrier. It should be noted that the combinations of two or more lipophilic surfactants from the same or different classes therein are also within the scope of this invention and are together can be referred to as the lipophilic surfactant, unless otherwise stated.

In some embodiments of the present invention, the oral pharmaceutical compositions or dosage forms (e.g. capsule or tablet) can include a hydrophilic additive. In one embodiment, hydrophilic additive is a selected from the group consisting of hydrophilic surfactant, celluloses—such as hydroxypropyl celluloses low molecular weight, low viscosity types (e.g. Methocel® E5, E6, E15, LV100 etc. grades) and hydroxypropyl celluloses having higher molecular weight, medium to high viscosity (e.g. Methocel® K4M, K15M, K100M etc); polyvinylpyrrolidones (e.g. Kollidon k17, K30 etc); polyvinyl acetates and combinations thereof.

In one embodiment, the hydrophilic additive can be a hydrophilic surfactant. A surfactant is considered to be a hydrophilic surfactant when it has an HLB value of greater than 10. Non-limiting examples of hydrophilic surfactants include non-ionic surfactants, ionic surfactants and zwitterionic surfactants. Specifically the hydrophilic surfactants suitable for the current invention include, but not limited to alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol and the like It should be noted that the combinations of two or more hydrophilic surfactants from the same or different classes are within the scope of this invention and are together can be referred to as the hydrophilic surfactant unless explicitly specified. In one embodiment, the hydrophilic additive can be a hydrophilic surfactant. Non-limiting examples of hydrophilic surfactants can include PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, and mixtures thereof.

In some embodiments, surfactants utilized in the pharmaceutical compositions described herein include sterols and derivatives of sterols. In various embodiments, these surfactants are hydrophilic or lipophilic. Examples of hydrophilic sterol surfactants are lanosterol PEG-24 cholesterol ether (e.g. Solulan C-24, Amerchol), PEG-30 soya sterol (e.g. Nikkol BPS-30, from Nikko), PEG-25 phyto sterol (e.g. Nikkol BPSH-25 from Nikko), PEG-30 cholestanol (e.g. Nikkol DHC, from Nikko). Examples of Lipophilic Sterol Surfactants are Cholesterol, sitosterol, Phytosterol (e.g. GENEROL series from Henkel), PEG-5 soya sterol (e.g. Nikkol BPS-S, from Nikko), PEG-10 soya sterol (e.g. Nikkol BPS-10 from Nikko), PEG-20 soya sterol (e.g. Nikkol BPS-20 from Nikko).

In one embodiment, the oral pharmaceutical composition or the dosage form comprises or is prepared from substantially pure (17-β)-3-Oxoandrost-4-en-17-yl tridecanoate and a pharmaceutically acceptable carrier, wherein substantially pure (17-β)-3-Oxoandrost-4-en-17-yl tridecanoate comprises about 0.5 wt % to about 50 wt %, 5 wt % to about 45 wt %, 15 wt % to about 40 wt %, 25 wt % to about 35 wt %, or 26 wt % to about 32 wt % of the composition or dosage form. In another embodiment, the compositions or the dosage form of the current invention includes substantially pure (17-β)-3-Oxoandrost-4-en-17-yl tridecanoate and a pharmaceutically acceptable carrier, wherein substantially pure (17-β)-3-Oxoandrost-4-en-17-yl tridecanoate comprises about 0.5 wt % to about 50 wt %, 5 wt % to about 45 wt %, 15 wt % to about 40 wt %, 25 wt % to about 35 wt %, or 26 wt % to about 32 wt % of the composition or dosage form, and wherein the carrier includes at least 50 wt % of the composition or the dosage form and wherein the substantially pure (17-β)-3-Oxoandrost-4-en-17-yl tridecanoate is not solubilized at 30° C., or above 30° C., or at a temperature range above 30° C., including 30° C. to about 40° C. In an additional more specific embodiment, the substantially pure (17-β)-3-Oxoandrost-4-en-17-yl tridecanoate is not fully dissolved in the carrier at human body temperature. In one aspect, the substantially pure (17-β)-3-Oxoandrost-4-en-17-yl tridecanoate is substantially free of impurities. In one aspect, the pharmaceutical composition or unit dosage form is formulated as a tablet or capsule (e.g., soft gel or hard gel). In one aspect, the pharmaceutical composition or unit dosage form further comprises one or more additives (e.g., 2, 3, 4, 5, 6, 7, 8, 9, or 10). In one aspect, the pharmaceutical composition or unit dosage form comprises a particular amount of substantially pure (17-β)-3-Oxoandrost-4-en-17-yl tridecanoate (e.g., 3 mg or more, 4 mg or more, 5 mg or more, 10 mg or more, 15 mg or more, 20 mg or more, 30 mg or more, 40 mg or more, 50 mg or more, 75 mg or more, 100 mg or more, 125 mg or more, 150 mg or more, 175 mg or more, 200 mg or more, 225 mg or more, 250 mg or more, 275 mg or more, or 300 mg or more) and typically less than 600 mg. In one aspect, the substantially pure (17-β)-3-Oxoandrost-4-en-17-yl tridecanoate is substantially free of impurities specifically disclosed herein or in any of the Figures.

In another embodiment, the compositions or the dosage forms includes or is prepared from substantially pure (17-β)-3-Oxoandrost-4-en-17-yl tridecanoate and a pharmaceutically acceptable carrier, wherein the substantially pure (17-β)-3-Oxoandrost-4-en-17-yl tridecanoate comprises about 0.5 wt % to about 50 wt %, 5 wt % to about 45 wt %, 15 wt % to about 40 wt %, 25 wt % to about 35 wt %, or 26 wt % to about 32 wt % of the composition or the dosage form, and wherein the carrier includes about 50 wt % to about 100 wt % of lipophilic surfactant and 0 wt % to about 50 wt % of hydrophilic surfactant. In a further embodiment, the substantially pure (17-β)-3-Oxoandrost-4-en-17-yl tridecanoate is not solubilized at 30° C., or above 30° C., or at a temperature range above 30° C., including 30° C. to about 40° C. In an additional more specific embodiment, the substantially pure (17-β)-3-Oxoandrost-4-en-17-yl tridecanoate is not fully dissolved in the carrier at human body temperature. In one aspect, the pharmaceutical composition or unit dosage form is formulated as a tablet or capsule (e.g., soft gel or hard gel). In one aspect, the pharmaceutical composition or unit dosage form further comprises one or more additives (e.g., 2, 3, 4, 5, 6, 7, 8, 9, or 10). In one aspect, the pharmaceutical composition or unit dosage form comprises a particular amount of substantially pure (17-β)-3-Oxoandrost-4-en-17-yl tridecanoate (e.g., 3 mg or more, 4 mg or more, 5 mg or more, 10 mg or more, 15 mg or more, 20 mg or more, 30 mg or more, 40 mg or more, 50 mg or more, 75 mg or more, 100 mg or more, 125 mg or more, 150 mg or more, 175 mg or more, 200 mg or more, 225 mg or more, 250 mg or more, 275 mg or more, or 300 mg or more) and typically less than 600 mg. In one aspect, the substantially pure (17-β)-3-Oxoandrost-4-en-17-yl tridecanoate is substantially free of impurities specifically disclosed herein or in any of the Figures.

In another specific embodiment, the composition or the dosage form includes or is prepared from substantially pure (17-β)-3-Oxoandrost-4-en-17-yl tridecanoate and a pharmaceutically acceptable carrier, wherein substantially pure (17-β)-3-Oxoandrost-4-en-17-yl tridecanoate comprises about 0.5 wt % to about 50 wt %, 5 wt % to about 45 wt %, 15 wt % to about 40 wt %, 25 wt % to about 35 wt %, or 26 wt % to about 32 wt % of the composition or the dosage form, and the carrier includes about 50 wt % to about 95 wt % a lipophilic surfactant and a hydrophilic surfactant 5 wt % to about 30 wt %. In one aspect, the lipophilic additive is a C16 to C18 fatty acid (saturated or having 1, 2, or 3 unsaturations), or a mono-, di-, or triglyceride thereof. In one aspect, mono-, di-, or tri glyceride is glyceryl palmitostearate. In one aspect, the hydrophilic component is a hydrogenated oil. In one aspect, the hydrophilic component is a polyoxylated hydrogenated oil. In a further more specific embodiment, the substantially pure (17-β)-3-Oxoandrost-4-en-17-yl tridecanoate is not solubilized at 30° C., or above 30° C., or at a temperature range above 30° C., including 30° C. to about 40° C. In an additional more specific embodiment, the ester is not fully dissolved in the carrier at human body temperature. In another more specific embodiment, the composition or the dosage form can optionally contain about 10 wt % or less of ethyl alcohol. In an additional more specific embodiment, the substantially pure (17-β)-3-Oxoandrost-4-en-17-yl tridecanoate is not fully dissolved in the carrier at human body temperature. In one aspect, the pharmaceutical composition or unit dosage form is formulated as a tablet or capsule (e.g., soft gel or hard gel). In one aspect, the pharmaceutical composition or unit dosage form further comprises one or more additives (e.g., 2, 3, 4, 5, 6, 7, 8, 9, or 10). In one aspect, the pharmaceutical composition or unit dosage form comprises a particular amount of substantially pure (17-β)-3-Oxoandrost-4-en-17-yl tridecanoate (e.g., 3 mg or more, 4 mg or more, 5 mg or more, 10 mg or more, 15 mg or more, 20 mg or more, 30 mg or more, 40 mg or more, 50 mg or more, 75 mg or more, 100 mg or more, 125 mg or more, 150 mg or more, 175 mg or more, 200 mg or more, 225 mg or more, 250 mg or more, 275 mg or more, or 300 mg or more) and typically less than 600 mg. In one aspect, the substantially pure (17-β)-3-Oxoandrost-4-en-17-yl tridecanoate is substantially free of impurities specifically disclosed herein or in any of the Figures.

In one embodiment, the hydrophilic surfactant can comprise at least about 20% of the total pharmaceutical carrier. In another embodiment, the hydrophilic surfactant can comprise at least about 5 wt % of the carrier. In another embodiment, the hydrophilic surfactant can comprise less than 5, 4, 3, 2, or 1 wt % of the carrier.

In another embodiment, the composition or the dosage form includes or is prepared from substantially pure (17-β)-3-Oxoandrost-4-en-17-yl tridecanoate, wherein the substantially pure (17-β)-3-Oxoandrost-4-en-17-yl tridecanoate comprises about 0.5 wt % to about 50 wt %, 5 wt % to about 45 wt %, 15 wt % to about 40 wt %, 25 wt % to about 35 wt %, or 26 wt % to about 32 wt % of the composition or the dosage form, and wherein the composition includes about 50 wt % to about 100 wt % of lipophilic additive and 0 wt % to about 50 wt % of hydrophilic additive. In a specific embodiment, the lipophilic additive can be lipophilic surfactant and the hydrophilic additive can be hydrophilic surfactant. In one aspect, the lipophilic additive is a C16 to C18 fatty acid (saturated or having 1, 2, or 3 unsaturations), or a mono-, di-, or triglyceride thereof. In one aspect, mono-, di-, or tri glyceride is glyceryl palmitostearate. In one aspect, the hydrophilic component is a hydrogenated oil. In one aspect, the hydrophilic component is a polyoxylated hydrogenated oil. In a further embodiment, the substantially pure (17-β)-3-Oxoandrost-4-en-17-yl tridecanoate is not solubilized at 30° C., or above 30° C., or at a temperature range above 30° C., including 30° C. to about 40° C. In an additional more specific embodiment, the substantially pure (17-β)-3-Oxoandrost-4-en-17-yl tridecanoate is not fully dissolved in the lipophilic additive or the composition at human body temperature. In an additional more specific embodiment, the substantially pure (17-β)-3-Oxoandrost-4-en-17-yl tridecanoate is not fully dissolved in the carrier at human body temperature. In one aspect, the pharmaceutical composition or unit dosage form is formulated as a tablet or capsule (e.g., soft gel or hard gel). In one aspect, the pharmaceutical composition or unit dosage form further comprises one or more additives (e.g., 2, 3, 4, 5, 6, 7, 8, 9, or 10). In one aspect, the pharmaceutical composition or unit dosage form comprises a particular amount of substantially pure (17-β)-3-Oxoandrost-4-en-17-yl tridecanoate (e.g., 3 mg or more, 4 mg or more, 5 mg or more, 10 mg or more, 15 mg or more, 20 mg or more, 30 mg or more, 40 mg or more, 50 mg or more, 75 mg or more, 100 mg or more, 125 mg or more, 150 mg or more, 175 mg or more, 200 mg or more, 225 mg or more, 250 mg or more, 275 mg or more, or 300 mg or more) and typically less than 600 mg. In one aspect, the substantially pure (17-β)-3-Oxoandrost-4-en-17-yl tridecanoate is substantially free of impurities specifically disclosed herein or in any of the Figures.

In one embodiment, the hydrophilic surfactant can comprise at least about 20% of the composition. In another embodiment, the hydrophilic surfactant can comprise at least about 5 wt % of the composition. In another embodiment, the hydrophilic surfactant can comprise less than 5 wt % of the composition.

In some embodiments, the oral pharmaceutical composition or the dosage form can include both a lipophilic surfactant and hydrophilic surfactant. In one embodiment, the lipophilic surfactant and hydrophilic surfactant can be present in amounts such that the ratio of amount (wt %) of lipophilic surfactant to amount (wt %) of hydrophilic surfactant is greater than 2:1. In another embodiment, the lipophilic surfactant and hydrophilic surfactant can be present in amounts such that the ratio of amount (wt %) of lipophilic surfactant to amount (wt %) of hydrophilic surfactant is greater than 2.5:1. In another embodiment, the lipophilic surfactant and hydrophilic surfactant can be present in amounts such that the ratio of amount (wt %) of lipophilic surfactant to amount (wt %) of hydrophilic surfactant is greater than 3.5:1. In still another embodiment, the lipophilic surfactant and hydrophilic surfactant can be present in amounts such that the ratio of amount (wt %) of lipophilic surfactant to amount (wt %) of hydrophilic surfactant is at least 6.5:1.

Methods of Use

Subjects that can be treated by pharmaceutical compositions and unit dosage forms of the present disclosure (e.g., prepared from or comprising substantially pure (17-β)-3-Oxoandrost-4-en-17-yl tridecanoate substantially free of impurities) can be any mammal (e.g., male or female) in need thereof. In particular, in one embodiment, the human male is at least 14, 16, or 18 years of age. In another embodiment, the human male is at least age 20, 21, 25 or 30. In a further embodiment, the subject is an adult male of at least age 40 or 50. In yet a further embodiment, the subject can be an adult male of at least age 60. Subjects that can be treated by pharmaceutical compositions and unit dosage forms of the present disclosure prepared from or comprising substantially pure (17-β)-3-Oxoandrost-4-en-17-yl tridecanoate substantially free of impurities) can be any human male in need thereof. In particular, in one embodiment, the human female may be at least 14 years of age. In some embodiments, the human subject is a female. For example, in another embodiment, the human female is an adult of at least 20 or 30 years of age. In a further embodiment, the subject can be an adult female of at least age 40 or 50. In a further embodiment, the subject can be an adult female who is deficient in the endogenous serum testosterone levels. In a further embodiment, the subject can be an adult female who has undergone unilateral or bilateral oophorectomy. In yet a further embodiment, the subject can be an adult female who has undergone unilateral or bilateral oophorectomy. In yet another embodiment, the subject can be a post-menopausal woman.

As discussed above, a method of treating a human subject in need of testosterone therapy is provided. The method can include the steps of administering any of the pharmaceutical compositions or dosage forms (e.g., capsule or tablet) disclosed herein. The pharmaceutical compositions and the dosage forms of the present invention can be used to treat any condition associated with testosterone deficiency, including complete absence, of endogenous testosterone in male or female subjects. Examples of conditions associated with testosterone deficiency that can be treated using the dosage forms (e.g., capsule or tablet) or compositions described herein include, but are not limited to congenital or acquired primary hypogonadism, hypogonadotropic hypogonadism, cryptorchidism, bilateral torsion, orchitis, vanishing testis syndrome, orchidectomy, Klinefelter's syndrome, post castration, eunuchoidism, hypopituitarism, endocrine impotence, infertility due to spermatogenic disorders, impotence, male sexual dysfunction (MSD) including conditions such as premature ejaculation, erectile dysfunction, decreased libido, and the like, micropenis and constitutional delay, penile enlargement, appetite stimulation, testosterone deficiency associated with chemotherapy, testosterone deficiency associated with toxic damage from alcohol, testosterone deficiency associated with toxic damage from heavy metal, osteoporosis associated with androgen deficiency, or a combination thereof.

Other conditions that can be treated by the compositions and dosage forms disclosed herein include idiopathic gonadotropin, LHRH deficiency, or pituitary hypothalamic injury from tumors, trauma, or radiation. Typically, these subjects have low serum testosterone levels but have gonadotropins in the normal or low range. In one embodiment, the composition or oral dosage form can be used to stimulate puberty in carefully selected males with clearly delayed puberty not secondary to pathological disorder. In another embodiment, the composition or oral dosage form can be used in female-to-male transsexuals in order to maintain or restore male physical and sexual characteristics including body muscle mass, muscle tone, bone density, body mass index (BMI), enhanced energy, motivation and endurance, restoring psychosexual activity etc. In some embodiments, pharmaceutical composition or unit dosage form of the present disclosure (e.g., prepared from or comprising substantially pure (17-β)-3-Oxoandrost-4-en-17-yl tridecanoate substantially free of impurities) can be useful in providing hormonal male contraception. In some embodiments, the pharmaceutical composition or unit dosage form of the present disclosure (e.g., prepared from or comprising substantially pure (17-β)-3-Oxoandrost-4-en-17-yl tridecanoate substantially free of impurities) can be used to provide treatment of one or more symptoms associated with female sexual dysfunction, anorgasmia, osteoarthritis, hormonal male contraception. Additionally, the pharmaceutical composition or unit dosage form of the present disclosure (e.g., prepared from or comprising substantially pure (17-β)-3-Oxoandrost-4-en-17-yl tridecanoate substantially free of impurities) can be used to treat and/or improve the patient related outcomes including the quality of life or wellbeing a subject suffering from deficiency of endogenous testosterone or who can otherwise benefit from the treatment. In some embodiments, the pharmaceutical composition or unit dosage form of the present disclosure (e.g., prepared from or comprising (17-β)-3-Oxoandrost-4-en-17-yl tridecanoate substantially free of impurities) can be used to treat or improve one or more symptoms of a subject suffering from conditions such as decreased libido, diminishing memory, anemia due to marrow failure, renal failure, chronic respiratory or cardiac failure, steroid-dependent autoimmune disease, muscle wasting associated with various diseases such as AIDS, preventing attacks of hereditary angioedema or urticaria; andropause, and palliating cancer. In some situations, certain biomarkers such as for example, increased SHBG levels, can be used to diagnose a subject who may be in need of testosterone therapy. These biomarkers can be associated with conditions/disease states such as anorexia nervosa, hyperthyroidism, hypogonadism, androgen insensitivity/deficiency, alcoholic hepatic cirrhosis, primary biliary cirrhosis, and the like.

Methods of Using Substantially Pure (17-β)-3-Oxoandrost-4-en-17-yl Tridecanoate and Products Derived Therefrom In one embodiment, a pharmaceutical composition prepared by synthesizing (17-β)-3-Oxoandrost-4-en-17-yl tridecanoate to produce substantially pure (17-β)-3-Oxoandrost-4-en-17-yl tridecanoate solid and mixing the substantially pure (17-β)-3-Oxoandrost-4-en-17-yl tridecanoate with one or more pharmaceutically acceptable carriers to provide a pharmaceutical composition which is substantially free of impurities. In a related embodiment, a pharmaceutical composition is prepared by providing substantially pure (17-β)-3-Oxoandrost-4-en-17-yl tridecanoate solid and mixing the substantially pure (17-β)-3-Oxoandrost-4-en-17-yl tridecanoate with one or more pharmaceutically acceptable carriers to provide a pharmaceutical composition which is substantially free of impurities.

The compositions and unit dosage forms can be prepared by any suitable method known to the skilled artisan or developed in view of the teachings herein.

In one specific aspect, the carrier(s) and API are brought to or maintained at a temperature at which they are flowable (e.g., above 10° C., 20° C., 25° C., 30° C., 35° C., or 40° C.). In one aspect, the mixture of carrier and API is a clear solution at a specified temperature (e.g., above 10° C., 20° C., 25° C., 30° C., 35° C., or 40° C.). In one aspect, the mixture of carrier and API is a cloudy or hazy solution at a specified temperature (e.g., below 10° C., 20° C., 25° C., 30° C., 35° C., or 40° C.).

In one example, the composition is prepared by weighing all of the components, except the API into a clean stainless steel container and mixed together at ambient temperature or at elevated temperatures e.g., at about 25° C. to about 30° C., at about 30° C. to about 35° C., at about 35° C. to about 40° C., at about 40° C. to about 45° C., at about 45° C. to about 45° C., or 50° C. to about 70° C., using a stirrer. The API is added and stirred into the mixture of other components until the API dissolves. A predetermined quantity of this "liquid fill material" is disposed into a capsule (for example, hard gelatin capsule) to get the required API dose per dosage unit. The capsules are allowed to cool at room temperature, banded (if required) and packaged in a HDPE bottle and tightly closed with an appropriate lid. It is noted that various capsule sizes (e.g., hard gel or soft gel) are available to the skilled artisan and allow for variations in the amount of loading of API in mg per unit dosage form. Typically, soft gel capsules for oral administration have fill volumes of less than 1.5 mL, 1.3 mL or 1.25 mL with numerous incremental fill volumes in these ranges. Similarly, hard gel capsules typically have fill volumes of less than 1.25 mL, 1.10 mL or 1 mL. Due to the nature of some hard gel capsules, the total fill volume may not be useable. There is a practical limit on the temperature at which capsules can be filled for example temperature above 40° C. typically melt, deform, or otherwise damage soft gel capsules typically employed in the industry. Hard gel capsules are typically less sensitive to temperature and can be filled at higher temperatures e.g., above 40° C.

In certain embodiments, any pharmaceutical composition described herein, e.g., a can be prepared by (i) combining and heating all ingredients until a molten mixture is obtained (e.g., 50-70° C.); and (ii) encapsulating an amount of molten mixture comprising a select dose (e.g., a therapeutically effective amount or a partial dose of a therapeutically effective amount) API to obtain an oral dosage form. In certain instances, the molten mixture is spray-congealed to obtain beads. In some instances, the molten mixture is sprayed onto inert cores (e.g., sugar spheres) to obtain coated cores. In certain embodiments, such beads, cores, or similar forms are encapsulated or otherwise formulated to provide an oral dosage form. In some instances, the molten mixture is admixed, uniformly dispersed, or granulated over a carrier and compressed into a tablet dosage form. In certain embodiments, prior to compression, the molten mixture/carrier composition is further mixed with one or more pharmaceutical aid including, by way of non-limiting example, glidants, lubricants, binders, or the like. In some embodiments, the carrier is a therapeutically inert carrier such as, by way of non-limiting example, microcrystalline cellulose, starch, lactose, or the like.

In various embodiments, pharmaceutical compositions described herein are formulated as oral dosage forms. Oral dosage forms are prepared by any suitable process including one or more steps of, by way of non-limiting example, agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, pan coating, solvent dehydration, sonication, spheronization, spray chilling, spray congealing, spray drying, or the like.

In some embodiments, a pharmaceutical composition described herein is formulated with a substrate to form an oral dosage form. In various embodiments, substrates useful for formulating pharmaceutical compositions described herein as oral dosage forms include or comprise, by way of non-limiting example, a powder or a multiparticulate (e.g., one or more granule, one or more pellet, one or more bead, one or more spherule, one or more beadlet, one or more microcapsule, one or more millisphere, one or more mini capsule, one or more microcapsule, one or more nanocapsule, one or more nanosphere, one or more microsphere, one or more minitablet, one or more tablet, one or more capsule, or one or more combinations thereof). In certain instances, a powder constitutes a finely divided (milled, micronized, nanosized, precipitated) form of an active ingredient or additive molecular aggregates or a compound aggregate of multiple components or a physical mixture of aggregates of an active ingredient and/or additives.

The following examples are provided to promote a more clear understanding of certain embodiments of the present invention, and are in no way meant as a limitation thereon.

Example 1

Preparation of Substantially Pure Pharmaceutical Ingredient, (17-β)-3-Oxoandrost-4-en-17-yl tridecanoate 1) (17-β)-Hydroxy-4-Androsten-3-one (0.1 mol) is weighed into a 1000 mL 4N RB flask containing a stir bar;
2) Pyridine (160 mL) is added to the flask;
3) The flask is placed in an ice-water bath and fitted with a nitrogen inlet, addition funnel, thermocouple, and stopper. Stirring and nitrogen flow are started;
4) The funnel is charged with a solution of acid chloride (1.56 equiv e.g., acid chloride of tridecanoic acid) in heptane (160 mL), then fitted with an adapter connected to a bubbler;
5) The contents of the funnel are added dropwise over 30-40 min (Note: the internal temperature increases 5-7° C. during the addition);
6) When the addition is complete, the bath is removed and stirring is continued;
7) After 1 h, the reaction mixture is transferred to a large separatory funnel and diluted with heptane (1000 mL) (Note: Thin layer chromatography ("TLC") can be used to monitor the reaction e.g., after one hour);
8) The heptane solution is washed successively with 800 mL portions of: cold water (2×), 0.05 N NaOH, saturated NaHCO$_3$ (2×), water, brine, then dried over anhydrous Na$_2$SO$_4$ (~50 g). Then concentrated to dryness (rotavap/Tbath:S; 30° C.).

Example 2

Preparation of Solid State Pharmaceutical Ingredient Crystals

A reaction mixture of Example 1 can be transferred to water, ethanol, or methanol (or any other suitable solvent) and allowed to crystallize. The crystalline mass can be filtered by suction, washed with water, dried over phosphorous pentoxide and re-crystallized from another solvent e.g., oleic acid, hexane, heptanes, etc.

Example 3

Purification of (17-β)-3-Oxoandrost-4-en-17-yl tridecanoate Pharmaceutical Ingredient by Liquid Chromatograph Liquid chromatography can be used to purify or analyze the purity of samples having (17-β)-3-Oxoandrost-4-en-17-yl tridecanoate.

One exemplary liquid chromatographic method is as follows.

Column: size 0.3 m, diameter 4.0 mm; stationary phase end-capped octadecylsilyl silca gel for chromatography (5 uM); Temperature 40 C.
Mobile Phase water: acetonitrile (5:95 V/V)
Flow rate 1.0 mL/min
Detector—240 nm
Dissolve sample in mobile phase (e.g., 20 mg in 50 mL).
Injection: 20 uL.
Run time twice the ion time of (17-β)-3-Oxoandrost-4-en-17-yl tridecanoate.

Order of retention time of impurities and (17-β)-3-Oxoandrost-4-en-17-yl tridecanoate starting with first eluting is expected as follows:
(1) Tridecanoate;
(2) (17-β)-3-Oxoandrost-4-en-3-one;
(3) (17-β)-3-Oxoandrost-4-en-17-yl decanoate;
(4) (17-β)-3-Oxoandrost-4-en-17-yl undecanoate;
(5) (17-β)-3-Oxoandrost-4-en-17-yl dodecanoate;
(6) (17-β)-3-Oxoandrost-4-en-17-yl tridecanoate; and
(7) (17-β)-3-Oxoandrost-4-en-17-yl tetradecanoate.

According to this procedure, these impurities (and others) be analyzed and identified. For example, mass spectrometry in conjunction with liquid chromatography can be used to assess or identify impurities in a sample having (17-β)-3-Oxoandrost-4-en-17-yl tridecanoate.

Example 4

Figure 9:
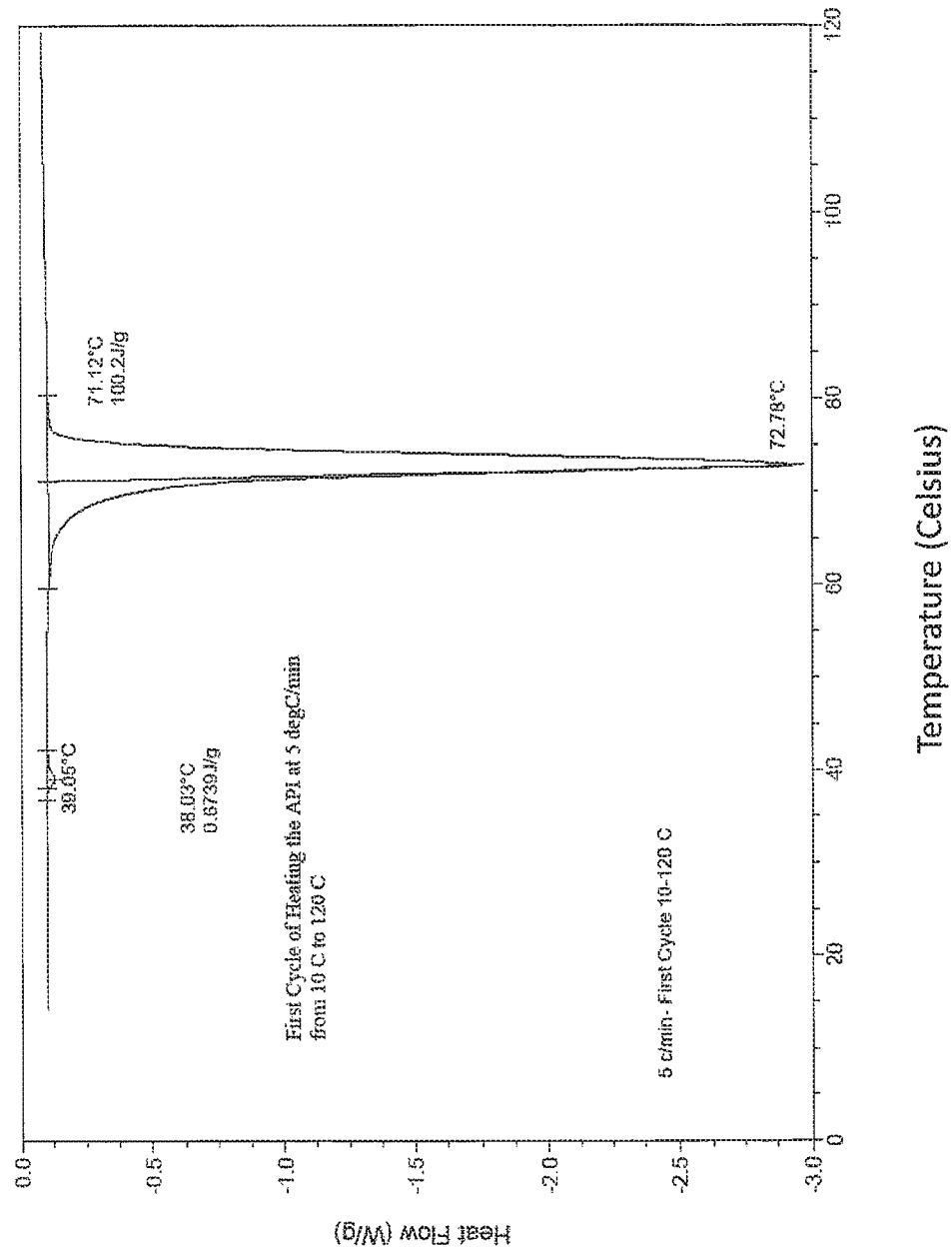
FIG. 9 shows a differential scanning calorimetery first heat cycle plot for a (17-β)-3-Oxoandrost-4-en-17-yl tridecanoate sample.
Figure 10:
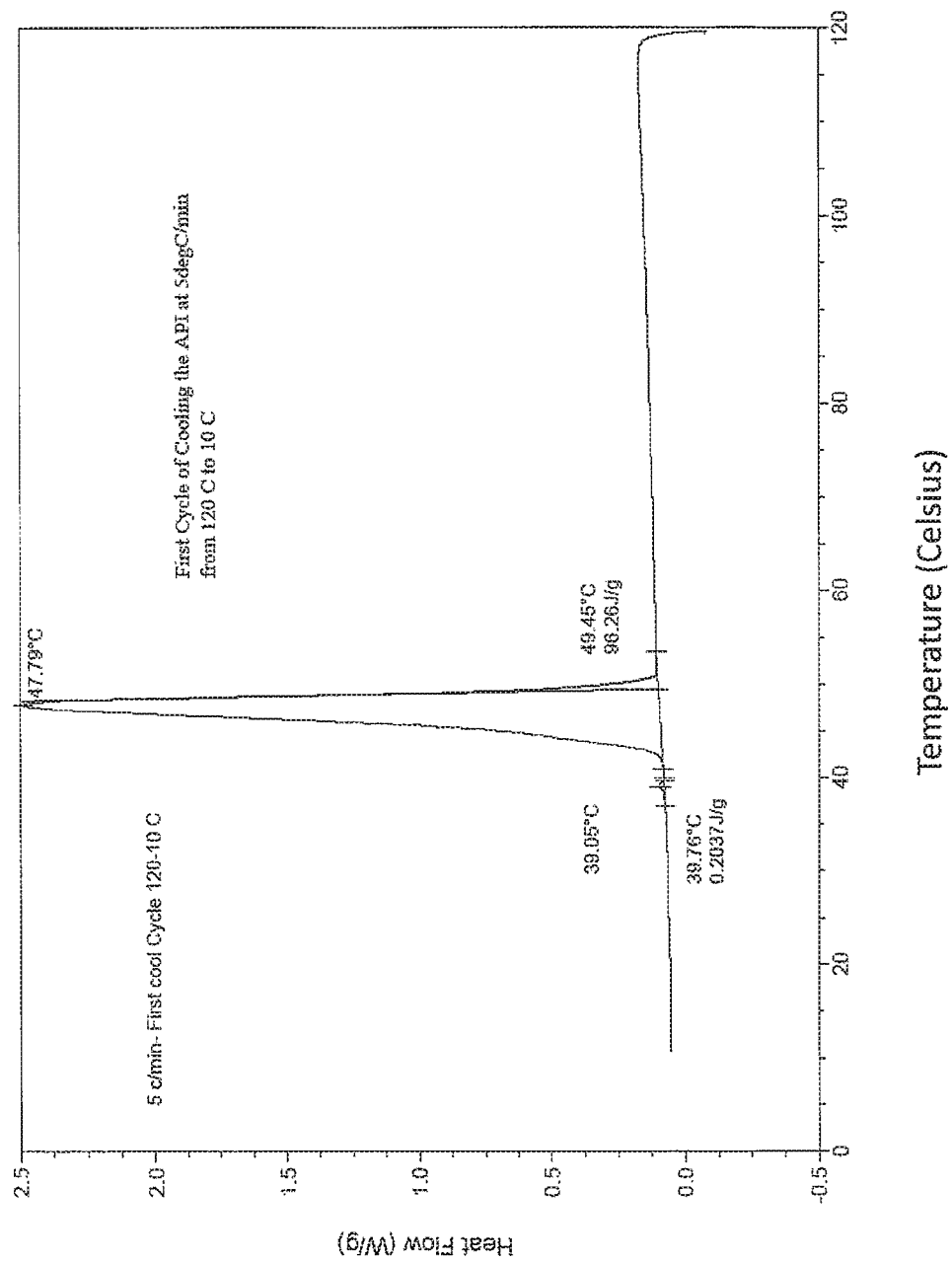
FIG. 10 shows a differential scanning calorimetry first cool cycle plot for a (17-β)-3-Oxoandrost-4-en-17-yl tridecanoate sample.
Figure 11:
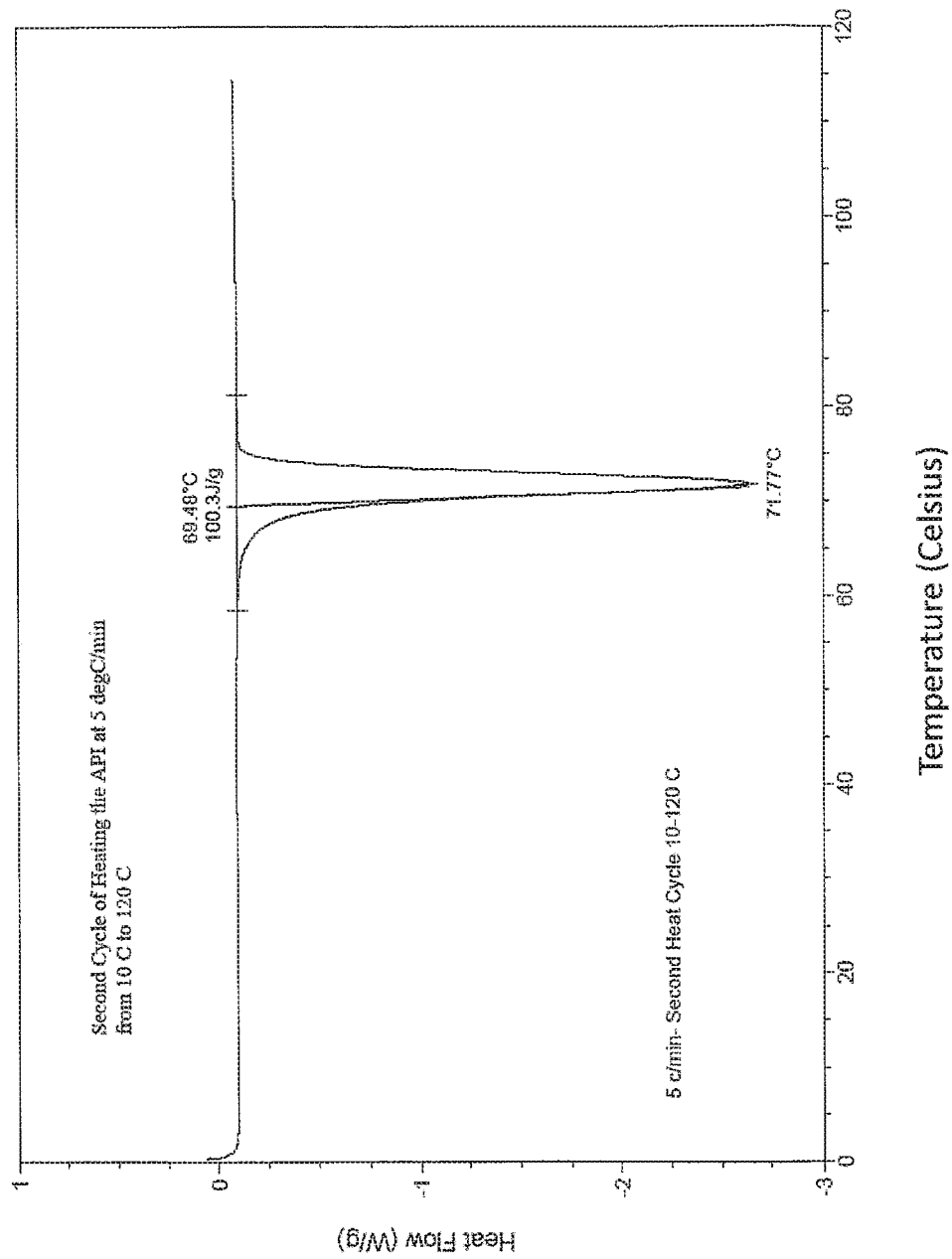
FIG. 11 shows a differential scanning calorimetry second heat cycle plot for a (17-β)-3-tridecanoate sample.
Figure 12:
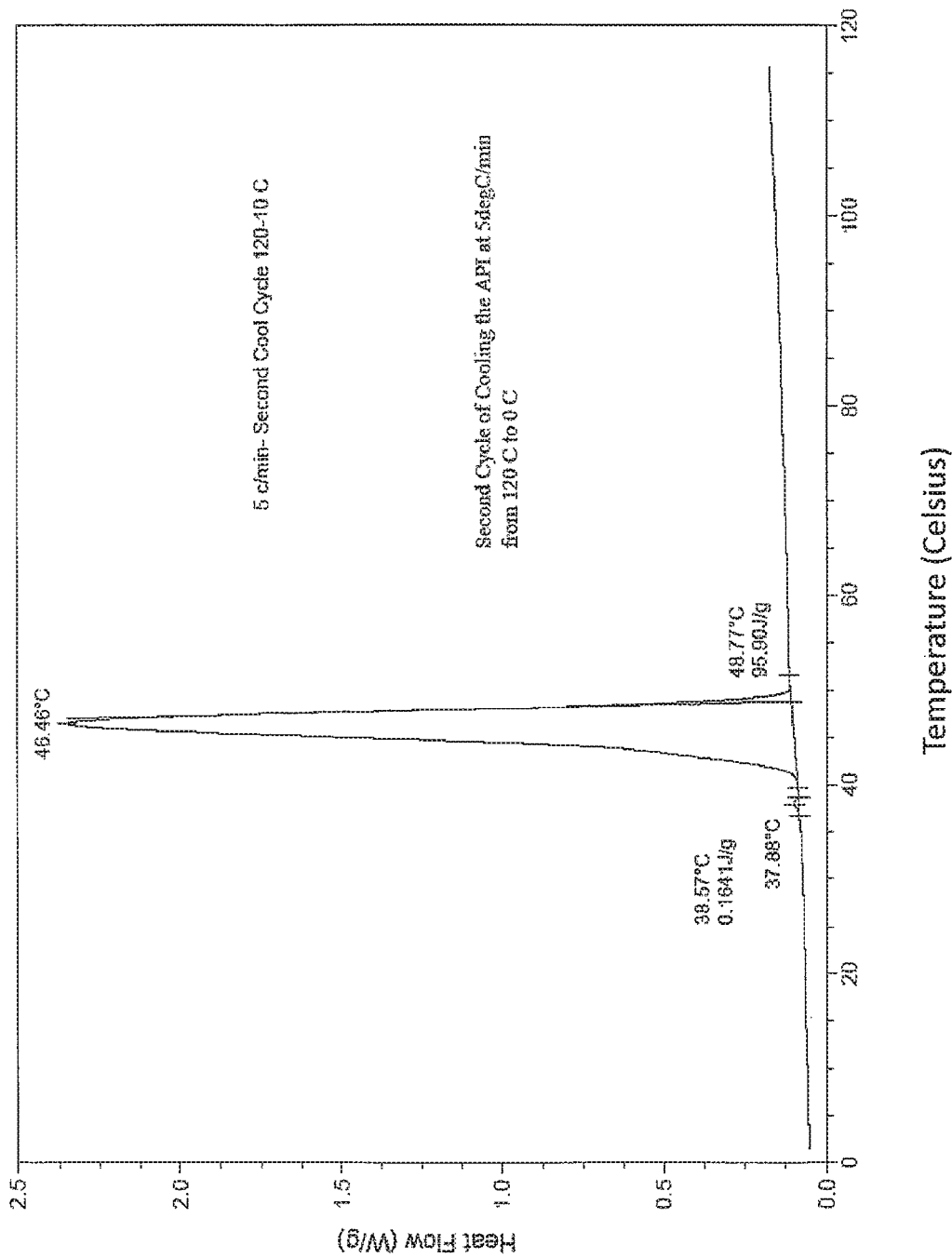
FIG. 12 shows a differential scanning calorimetry second cool cycle plot for a (17-β)-3-Oxoandrost-4-en-17-yl tridecanoate sample.

Differential Scanning Calorimetry (DSC) of Substantially Pure (17-β)-3-Oxoandrost-4-en-17-yl tridecanoate This example demonstrates that (17-β)-3-Oxoandrost-4-en-17-yl tridecanoate is substantially pure by DSC e.g., the (17-β)-3-Oxoandrost-4-en-17-yl tridecanoate has a distinct melting point as determined using a differential scanning calorimeter. 5.9 mg of solid state substantially pure (17-β)-3-Oxoandrost-4-en-17-yl tridecanoate was placed in the chamber of a DSC instrument and was heated from 10 to 120° C. The result is shown in FIG. 9, which shows a peak at 72.78° C. The second heating run of this sample is show in FIG. 11 which shows a single peak at 71.77. It is expected that (17-β)-3-Oxoandrost-4-en-17-yl tridecanoate having impurities will not have as distinct (sharp) a melting point or that it would be shifted depending on the amount and type of impurities. FIG. 10 and FIG. 12 show the first and cycle cooling cycles respectively.

Example 5

Separation of Impurities

Impurities in (17-β)-3-Oxoandrost-4-en-17-yl tridecanoate or composition containing (17-β)-3-Oxoandrost-4-en- 17-yl tridecanoate can be separated and/or identified according to the following procedure Column: C18
Mobile Phase: acetonitrile; alcohol; and deionized water.
Detector Wavelength: about 240 nm (e.g., 242 nm)
Flow Rate: 1.0 mL per minute
Column Temperature: 29° C.

Figure 13:
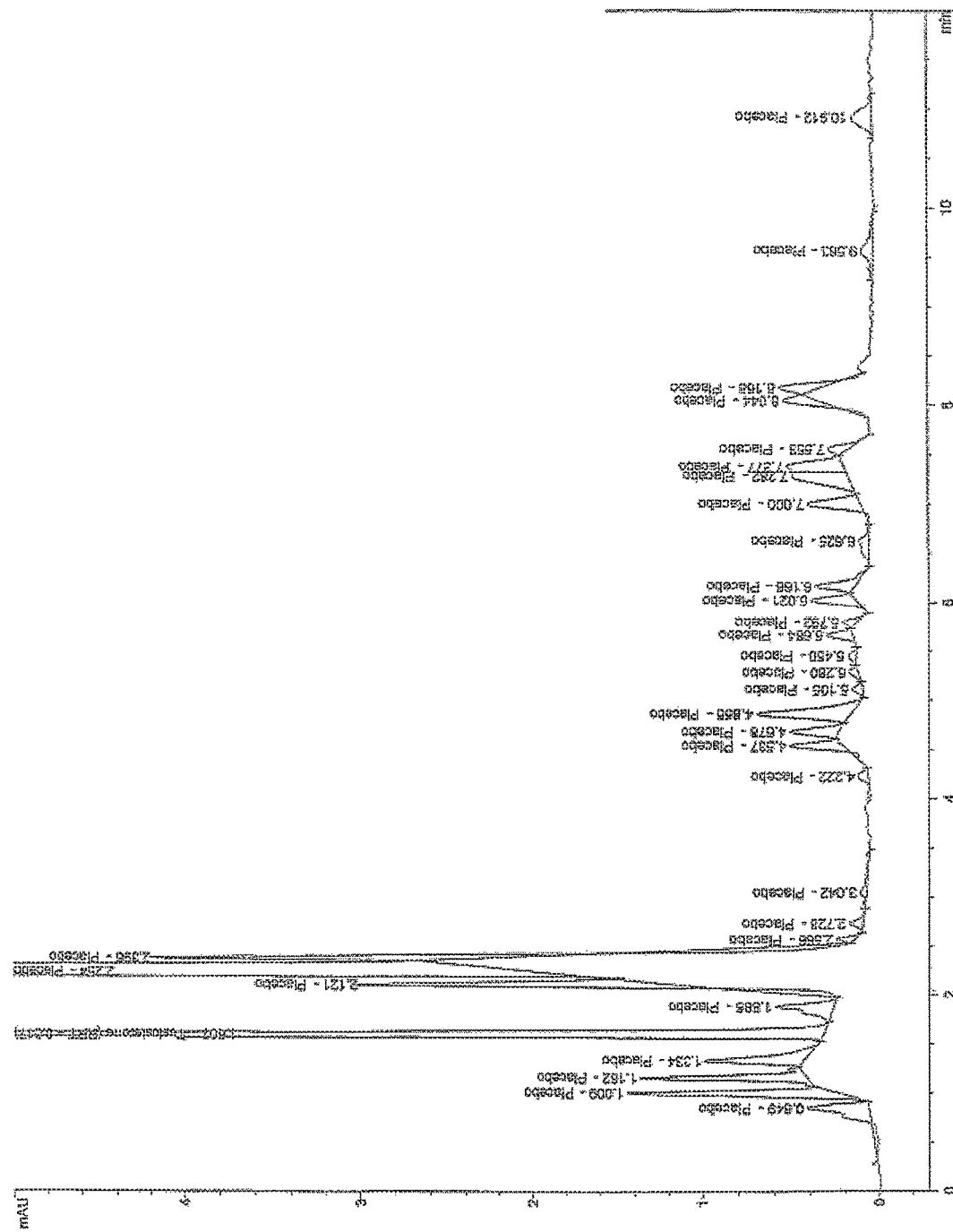
FIG. 13 shows a portion on an HPLC trace of a (17-β)-3-Oxoandrost-4-en-17-yl tridecanoate sample having impurities.
Figure 14:
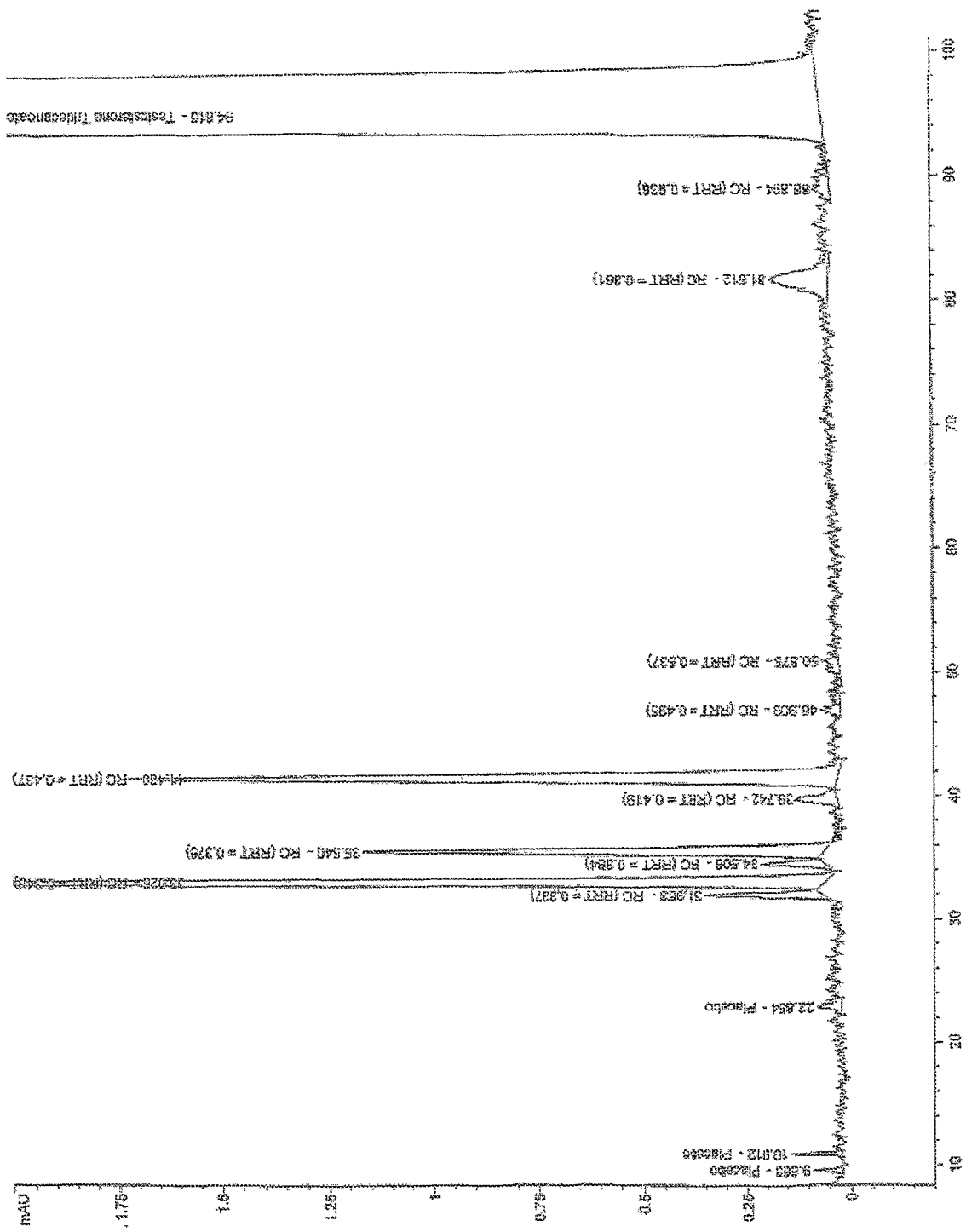
FIG. 14 shows a portion on an HPLC trace of a (17-β)-3-Oxoandrost-4-en-17-yl tridecanoate sample having impurities.
Figure 15:
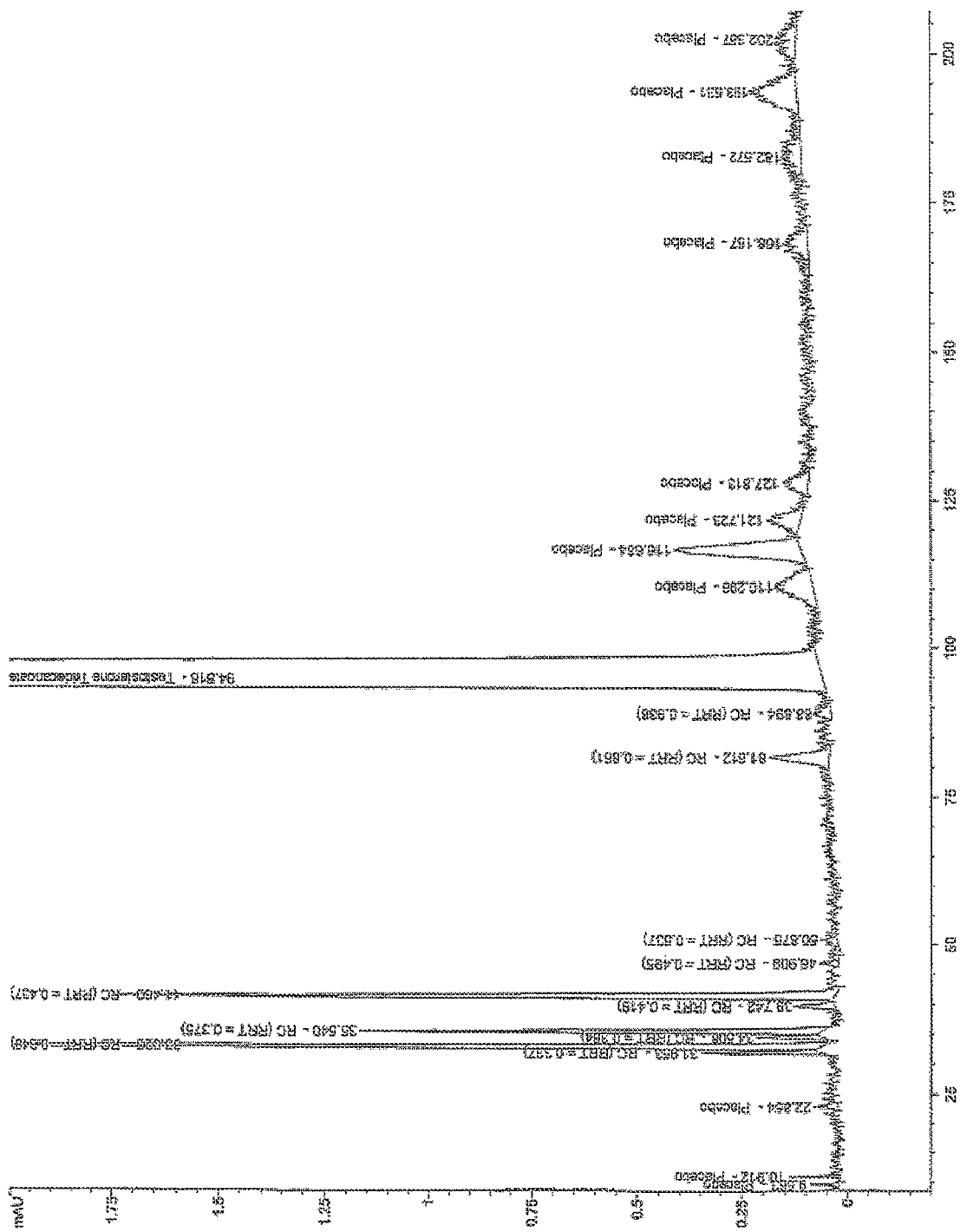
FIG. 15 shows a portion on an HPLC trace of a (17-β)-3-Oxoandrost-4-en-17-yl tridecanoate sample having impurities.

The sample used in this example was derived from a (17-β)-3-Oxoandrost-4-en-17-yl tridecanoate (89.9 mg) formulation/composition stored at 40° C. for 17 months. FIGS. 13-15 show different portions of the HPLC trace. Placebo labeled peaks were identified from a similar formulations not having (17-β)-3-Oxoandrost-4-en-17-yl tridecanoate. RC peaks are impurities believed to be related to (17-β)-3-Oxoandrost-4-en-17-yl tridecanoate. FIG. 13 shows the trace from about time zero to about 12 minutes with RC 1 identified as testosterone. FIG. 14 shows the trace from 8-105 minutes with RC 2-11 (from shortest to longest RRT) identified and the API. FIG. 15 shows trace from 8 minutes to 210 minutes with RC 2-11 shown and (17-β)-3-Oxoandrost-4-en-17-yl tridecanoate. RRT refers to the relative retention time to API.

The formulation in this Example is as follows:

| Ingredient Name | Weight Percent of Fill Pharmaceutical Composition (±1%) % w/w | Quantity Fill Material per Hard Gel Capsule (±1%) mg |
|---|---|---|
| API | 15 | 110 |
| Glyceryl Monolinoleate, NF | 63 | 463 |
| Polyoxyl 40 Hydrogenated Castor Oil, NF | 15 | 114 |
| Ascorbyl Palmitate, NF | 0.2 | 1.5 |
| Polyethylene Glycol 8000, NF | 6 | 44 |
| Total | 100 | 733.3 |

Figure 6:
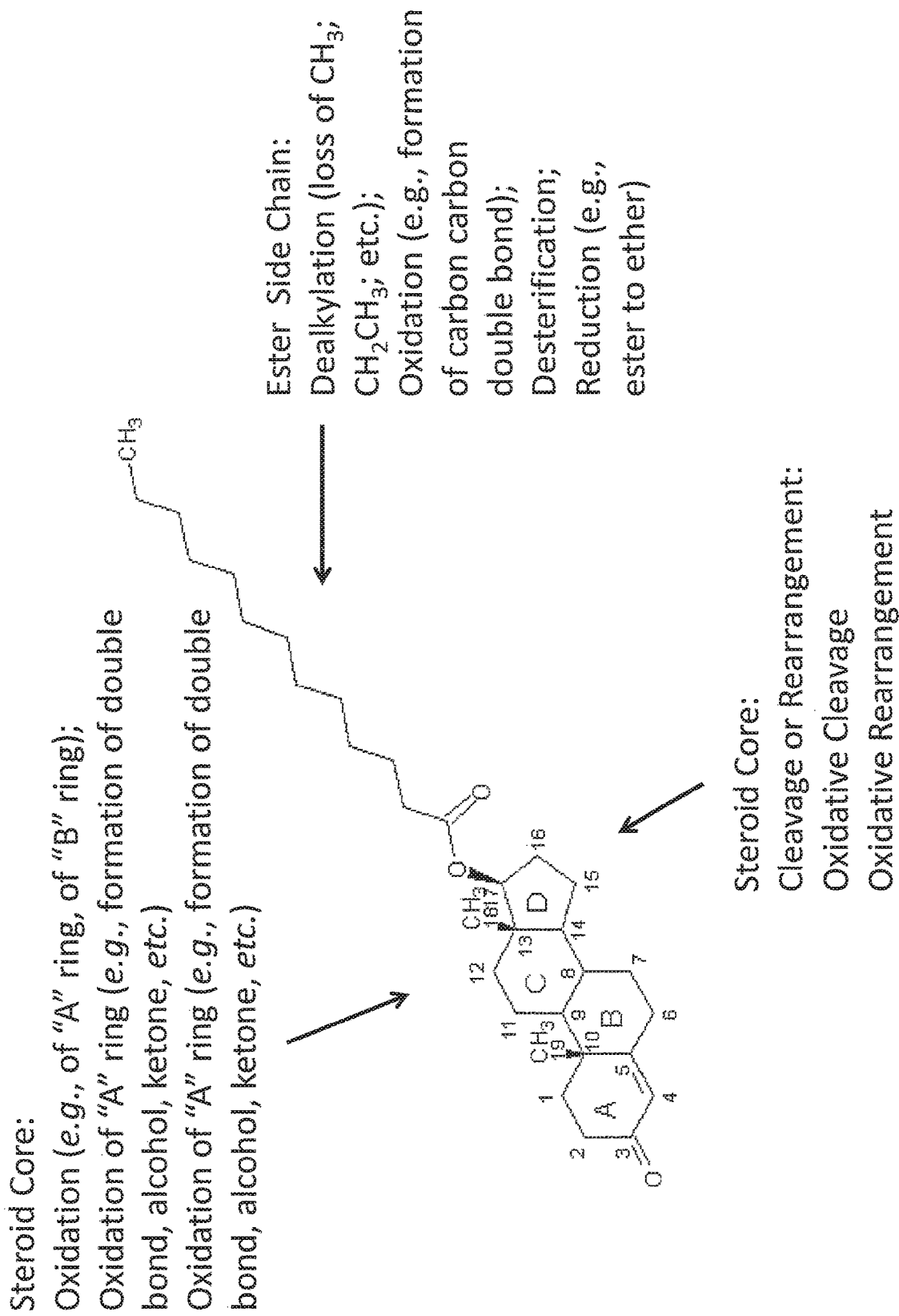
FIG. 6 shows a classification of potential impurities related to (17-β)-3-Oxoandrost-4-en-17-yl tridecanoate.
Figure 7:
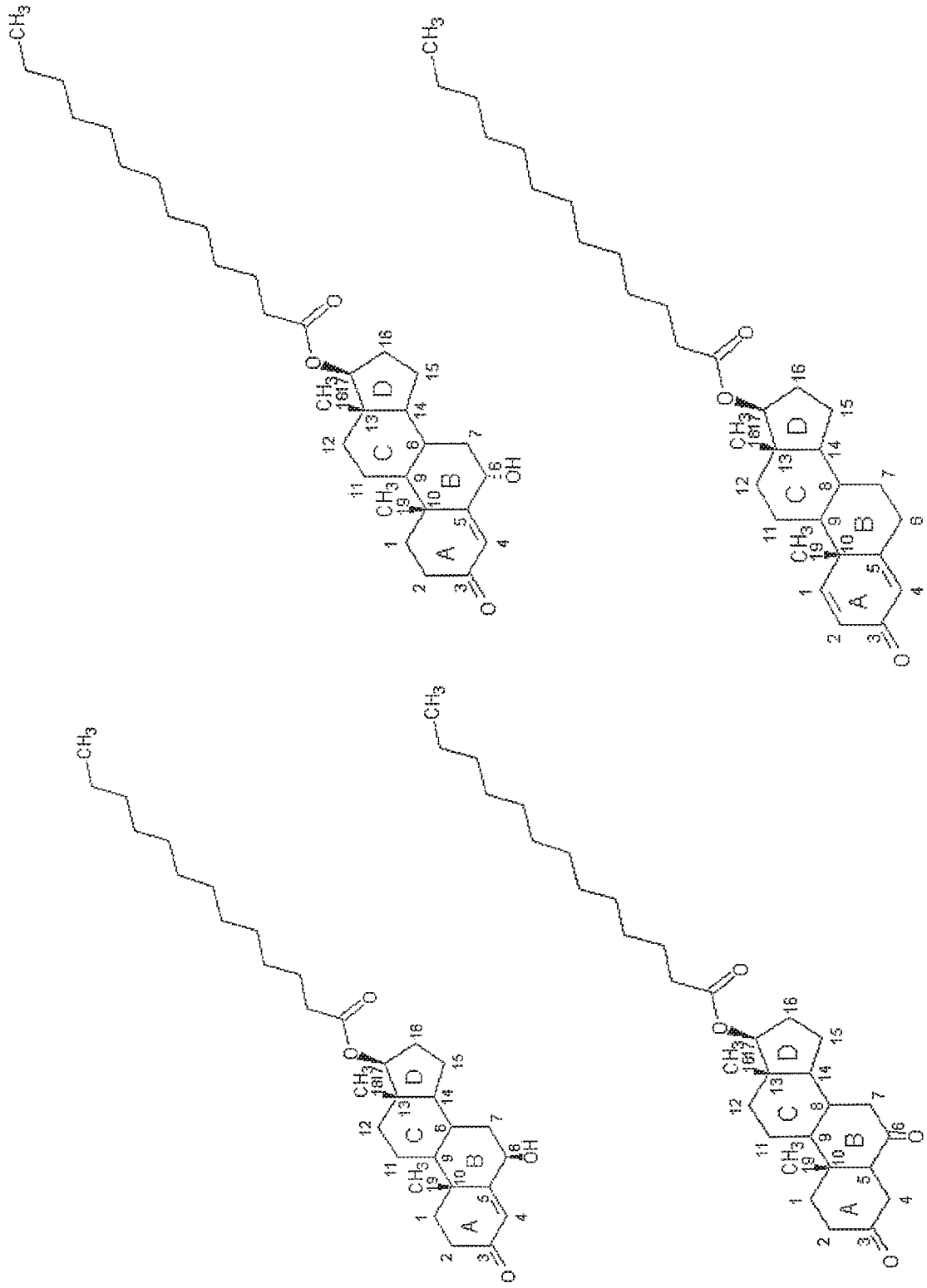
FIG. 7 shows the structures of several potential impurities related to (17-β)-3-Oxoandrost-4-en-17-yl tridecanoate.
Figure 8:
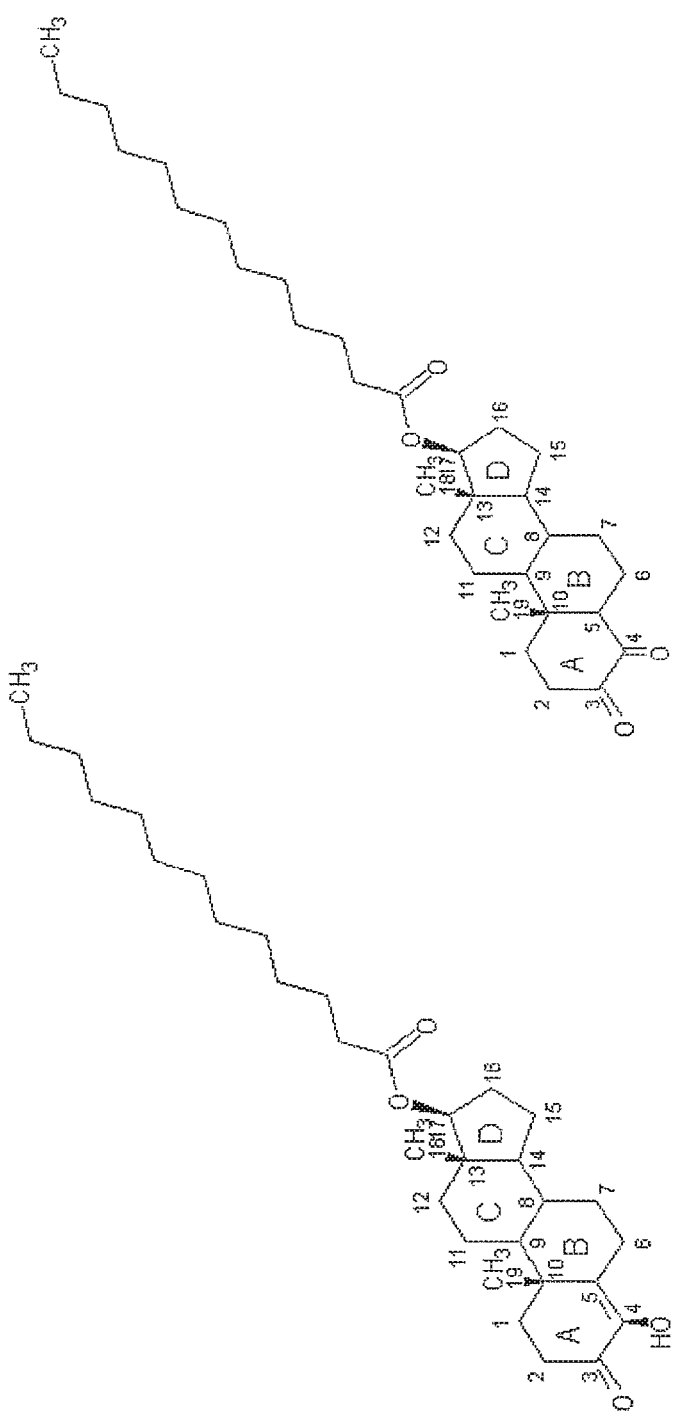
FIG. 8 shows the structures of several potential impurities related to (17-β)-3-Oxoandrost-4-en-17-yl tridecanoate.

It is believed that formulations without a stabilizing agent e.g., antioxidant (e.g., ascorbyl palmitate) had the buildup over time of the impurities putatively identified as hydroxylated at position 6 of the compound in FIG. 6 in the "out of the plane", "in the plane", or both. For example after two years storage of the composition without ascorbyl palmitate up to about 0.5% of these compounds could form.

Example 6

Identification of Impurities by LC/MS

Figure 16:
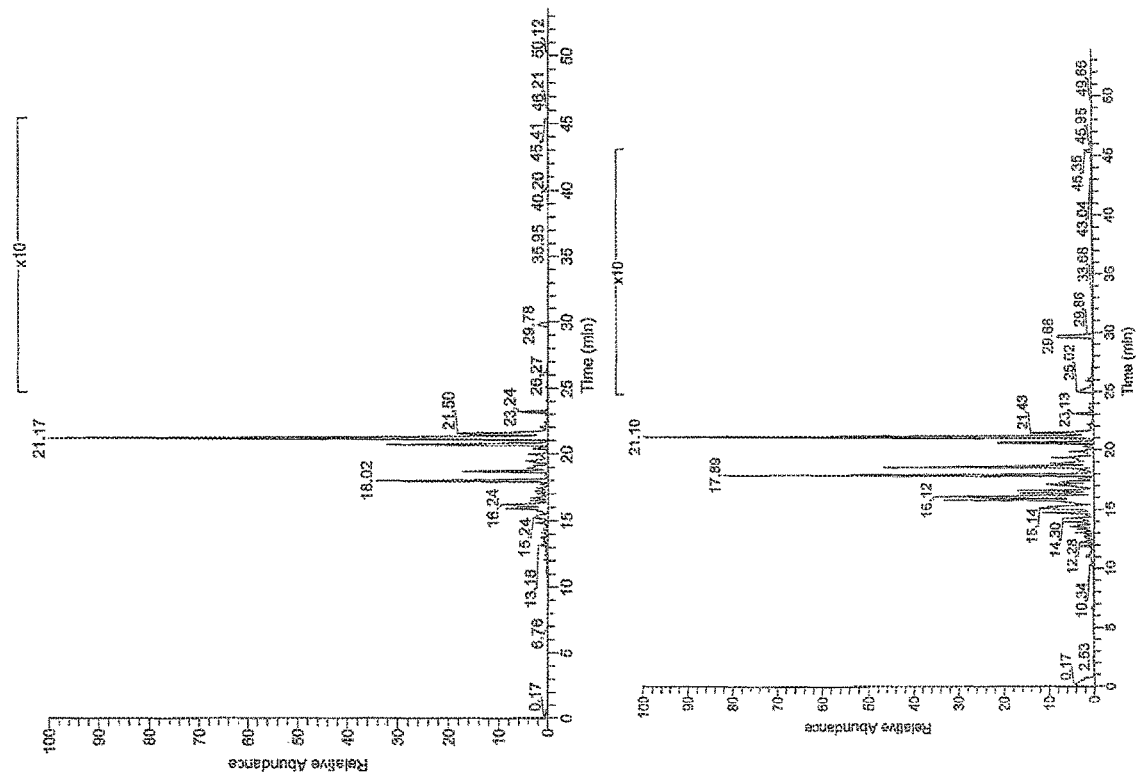
FIG. 16 shows the two mass spectrum from LCMS traces of (17-β)-3-Oxoandrost-4-en-17-yl tridecanoate sample from kept at elevated temperatures for 24 hours (lower trace) and 48 hours (upper trace). See example 6. The mass spectra of compounds corresponding to some of these peaks are shown in FIG. 18 through FIG. 28. The retention times are listed about the peaks in the traces.
Figure 17:
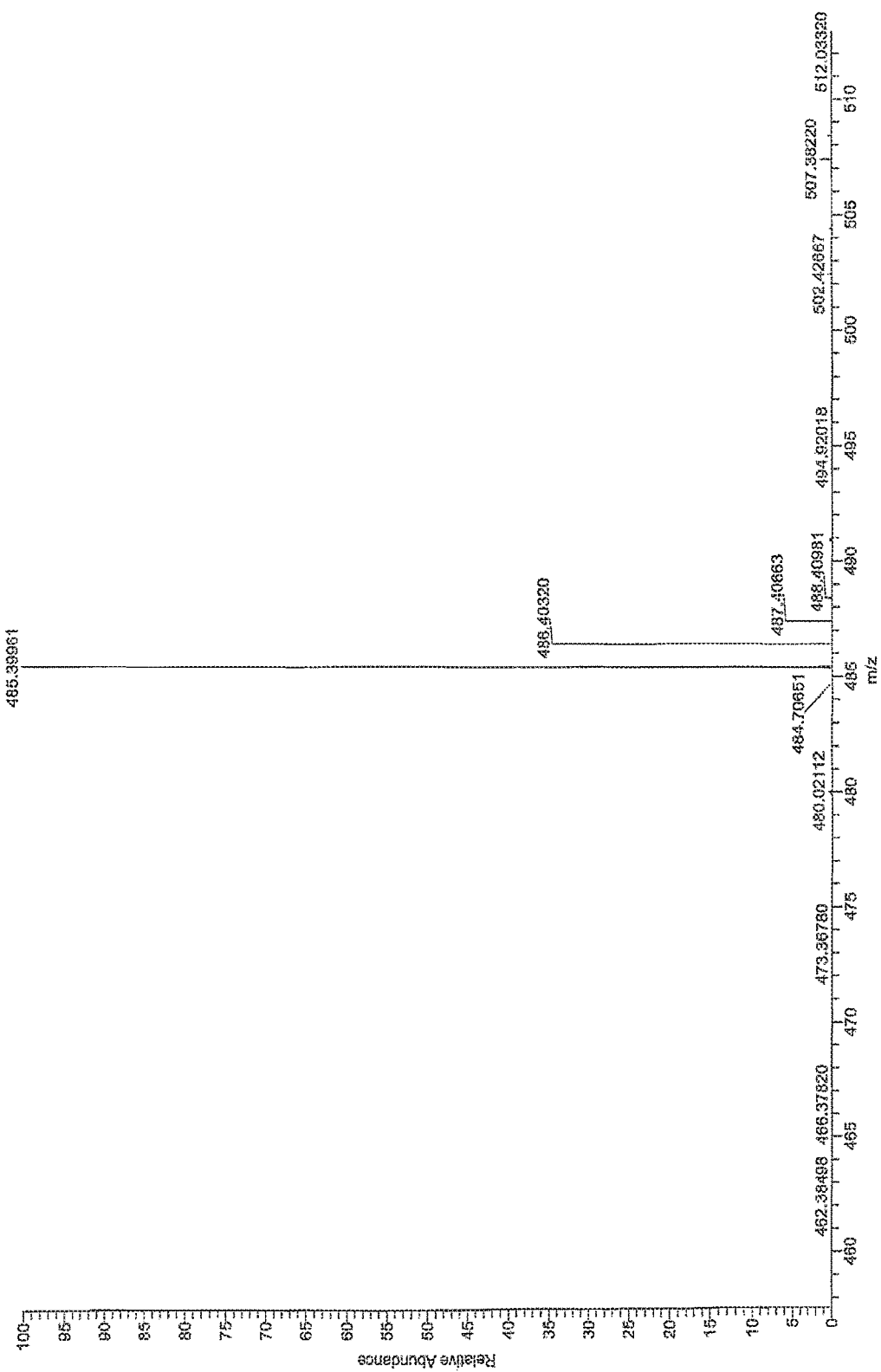
FIG. 17 shows a mass spectrum of peaks corresponding to a retention time 29.58-29.92 from the 48 hour sample.
Figure 18:
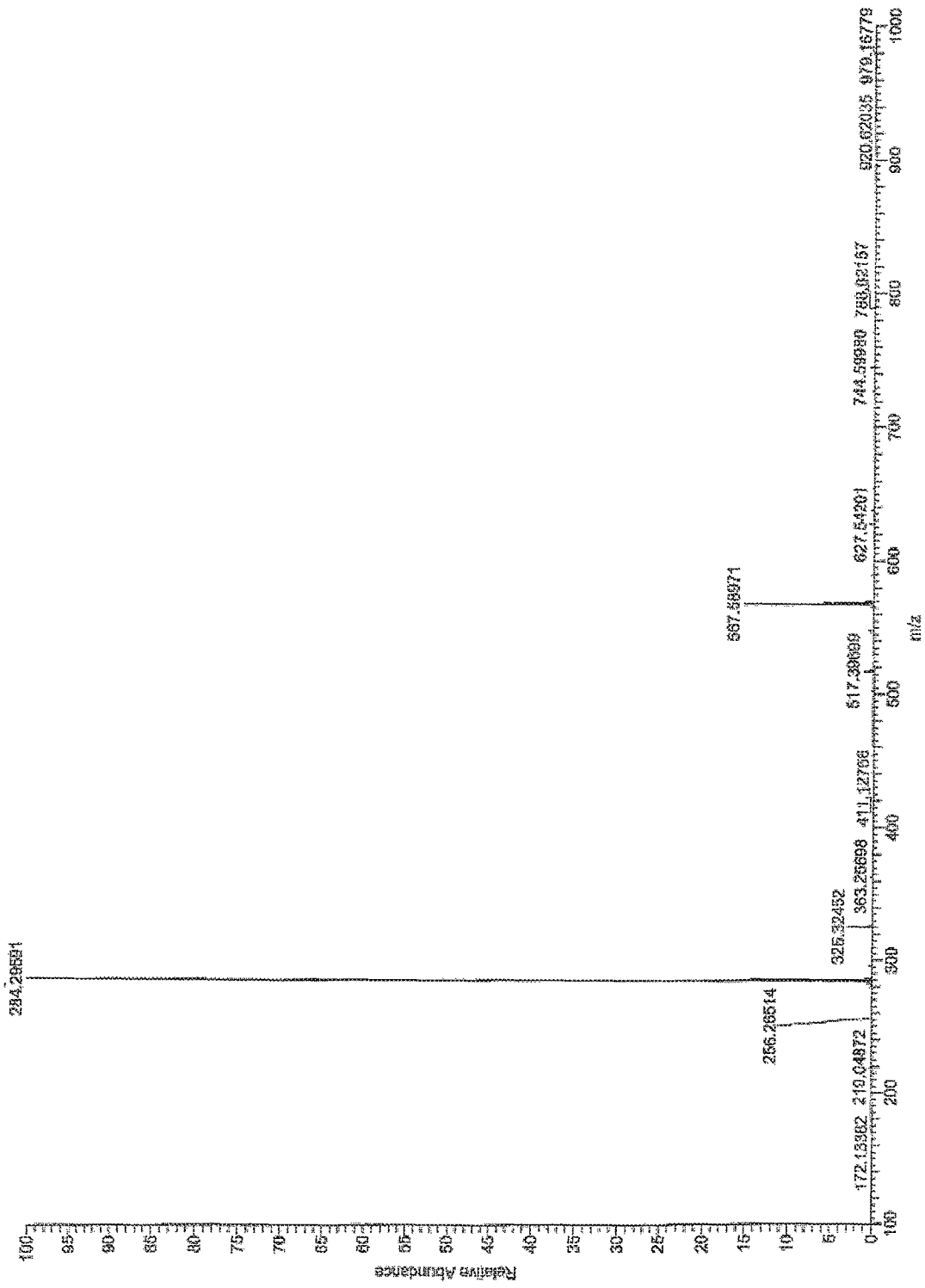
FIG. 18 shows a mass spectrum of peaks corresponding to a retention time 23.12-23.24 from the 48 hour sample.
Figure 19:
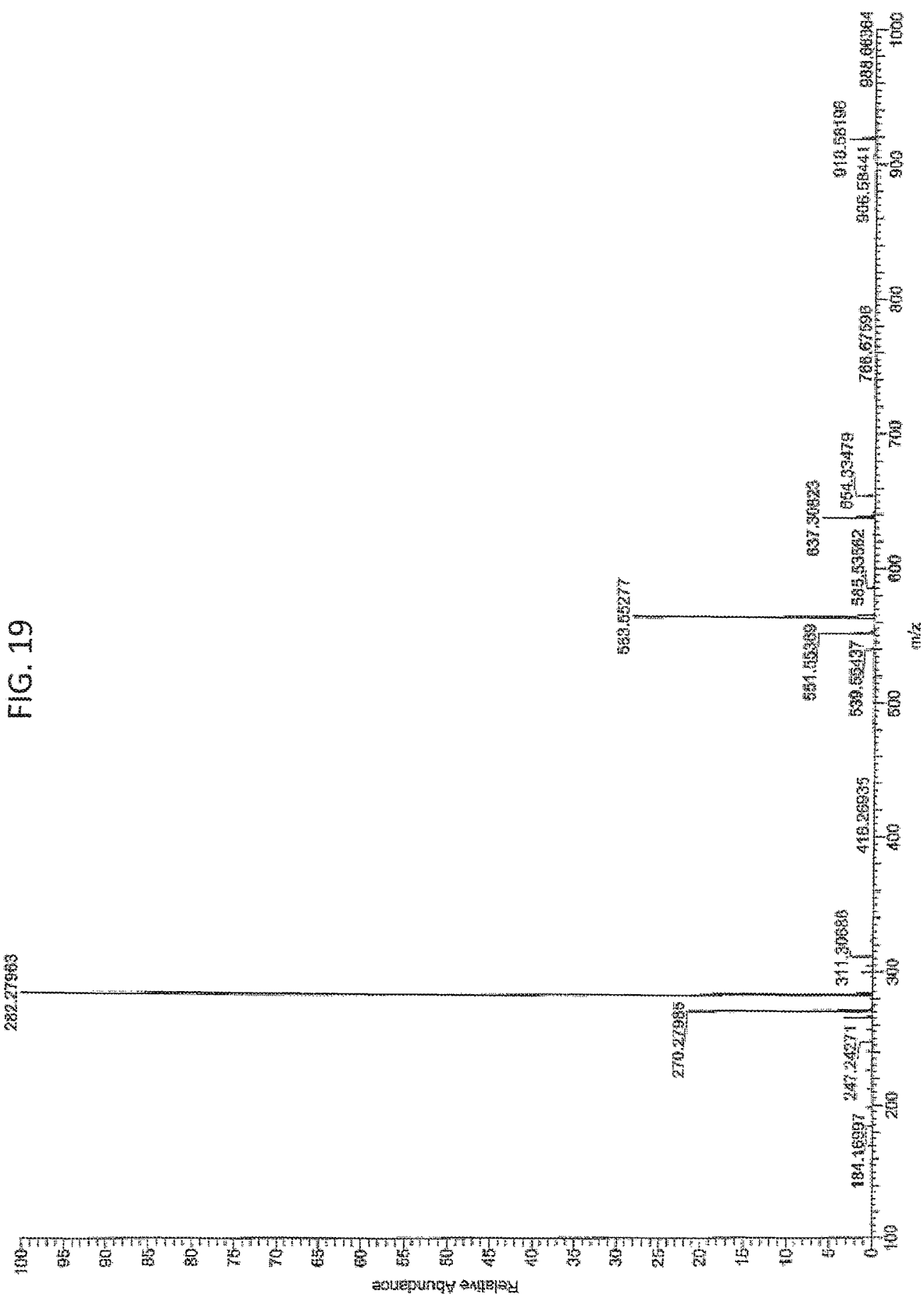
FIG. 19 shows a mass spectrum of peaks corresponding to a retention time 21.45-21.60 from the 48 hour sample.
Figure 20:
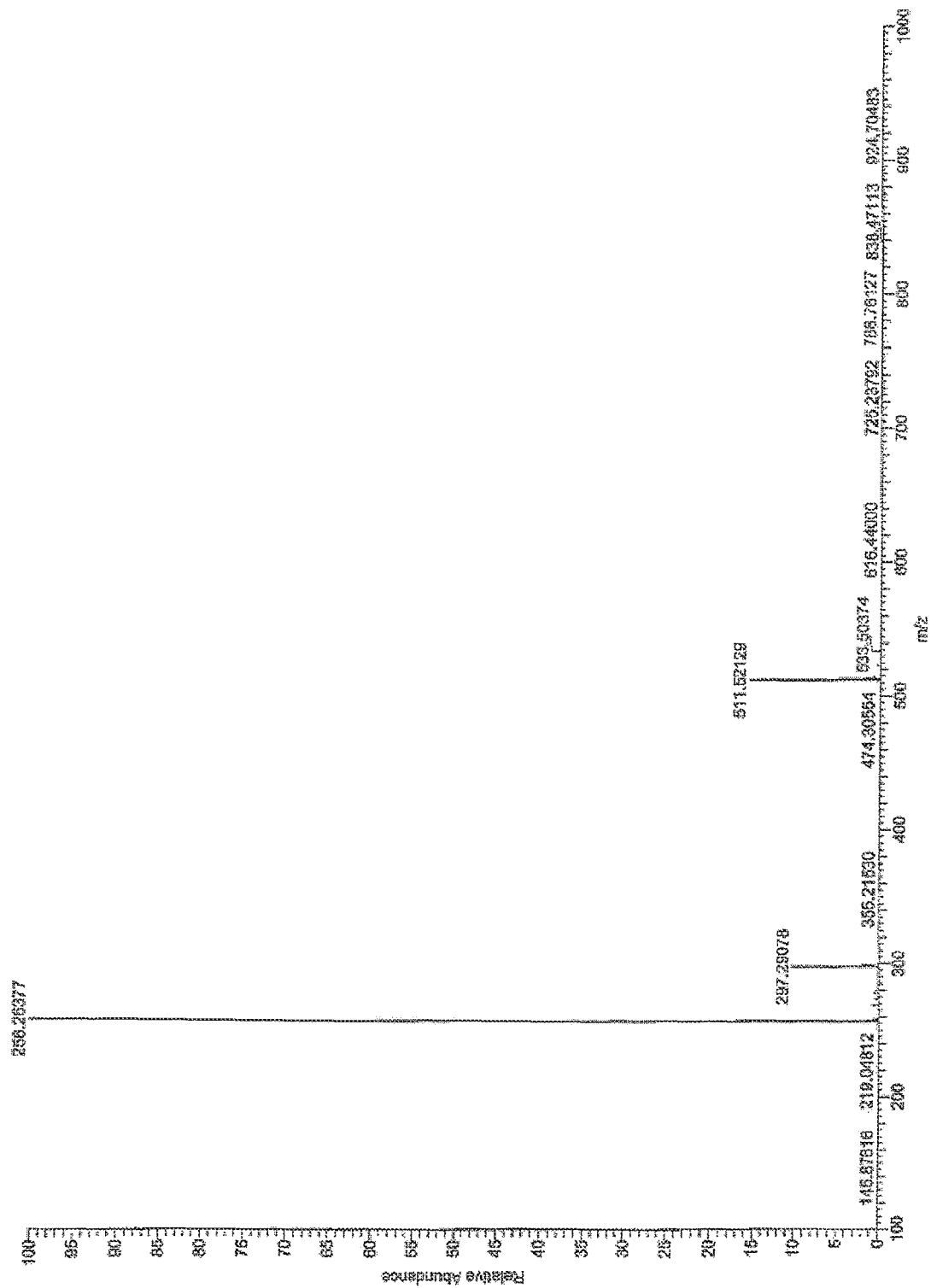
FIG. 20 shows a mass spectrum of peaks corresponding to a retention time 20.57-20.59 from the 48 hour sample.
Figure 21:
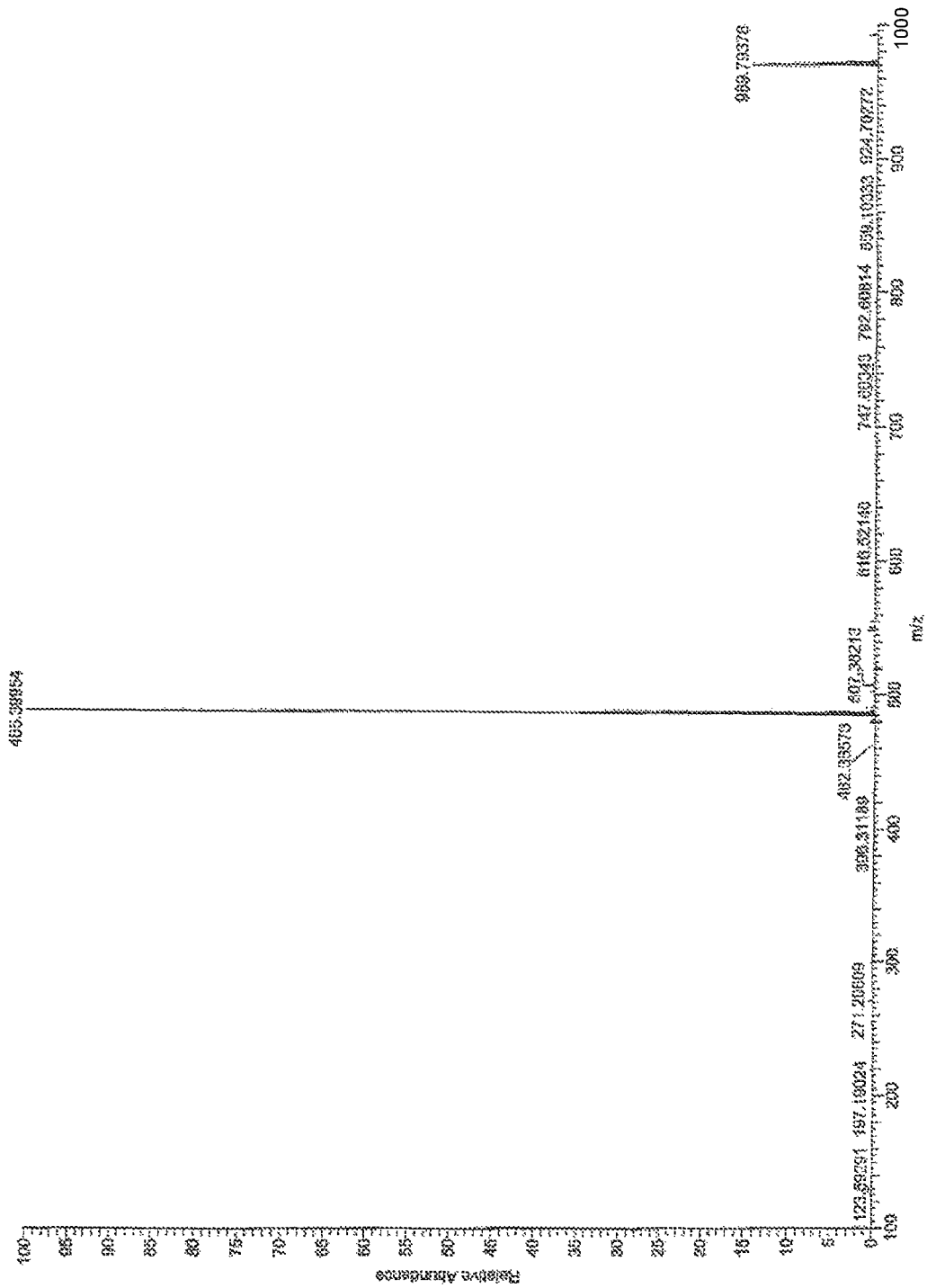
FIG. 21 shows a mass spectrum of peaks corresponding to a retention time 29.78-29.78 from the 24 hour sample.
Figure 22:
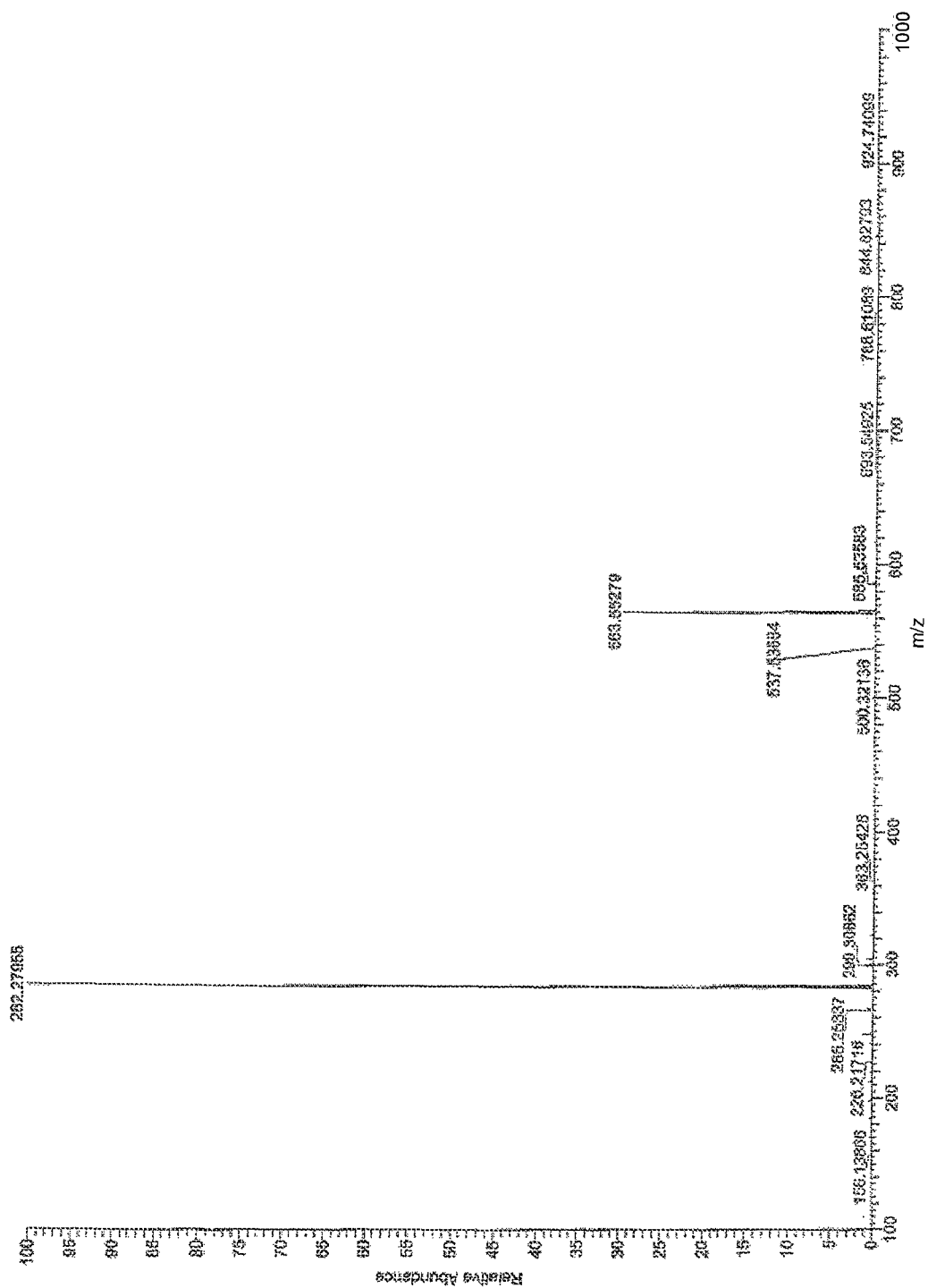
FIG. 22 shows a mass spectrum of peaks corresponding to a retention time 20.99-21.25 from the 24 hour sample.
Figure 23:
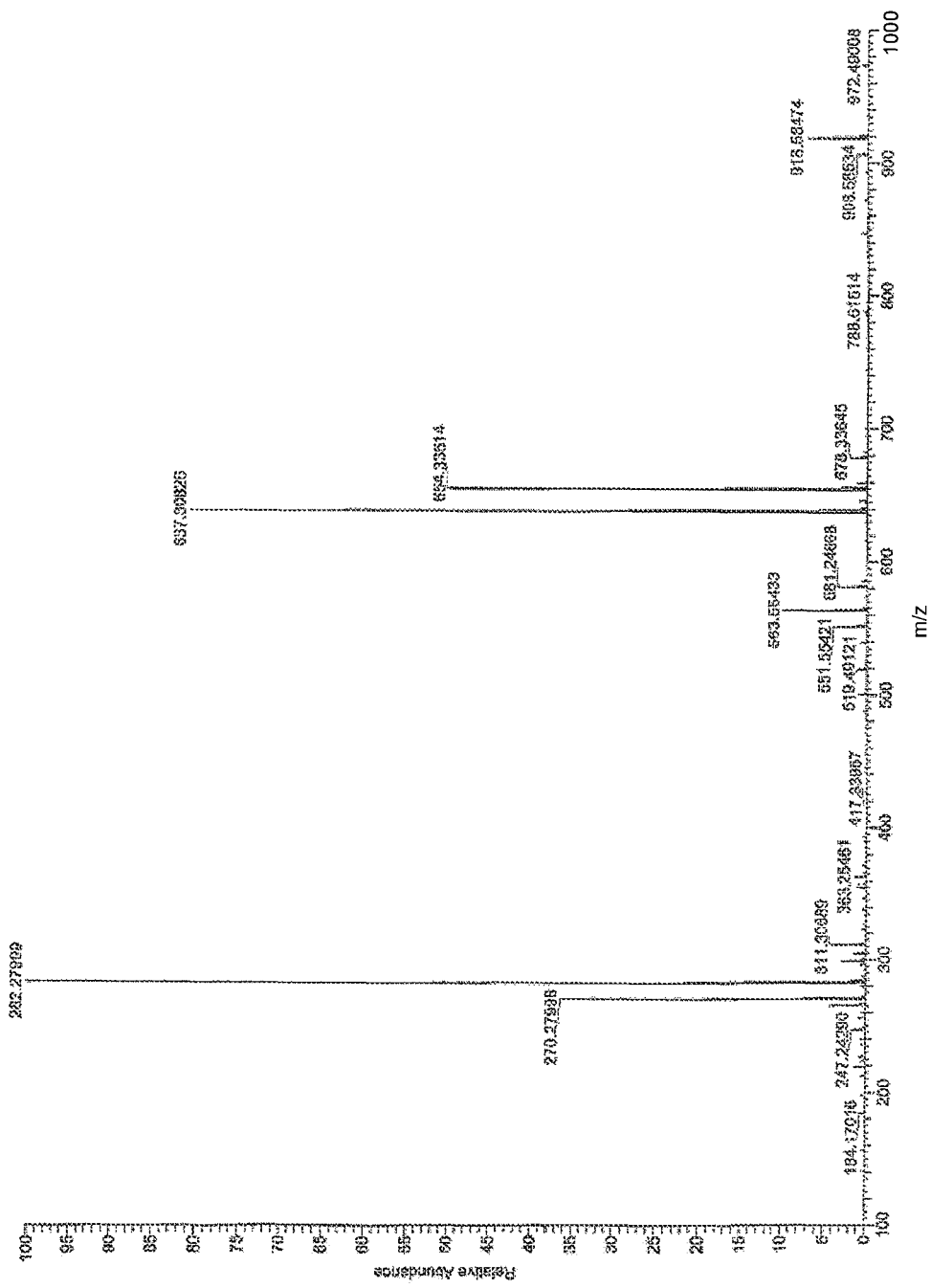
FIG. 23 shows a mass spectrum of peaks corresponding to a retention time 21.37-21.54 from the 24 hour sample.
Figure 24:
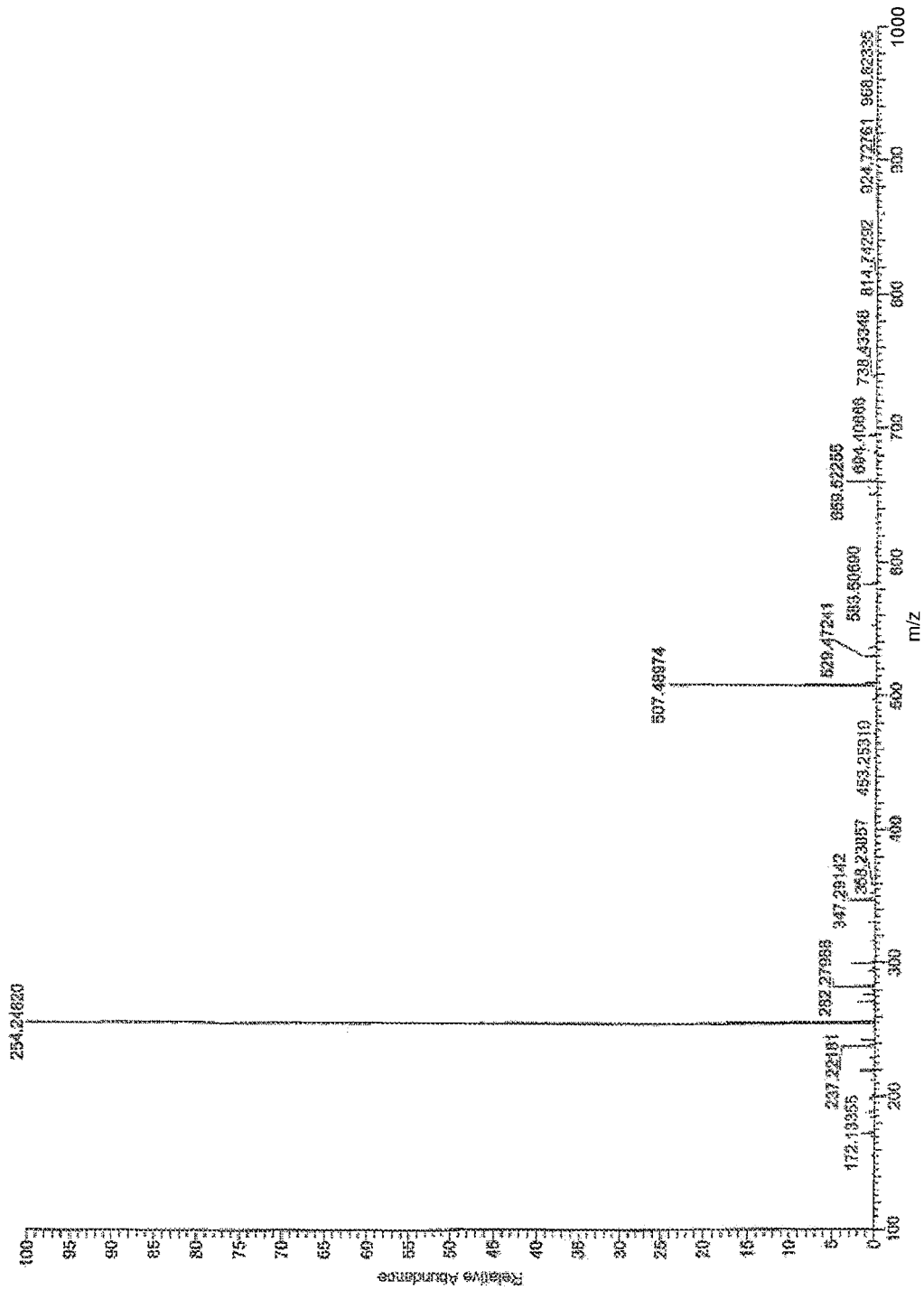
FIG. 24 shows a mass spectrum of peaks corresponding to a retention time 18.47-18.76 from the 24 hour sample.
Figure 25:
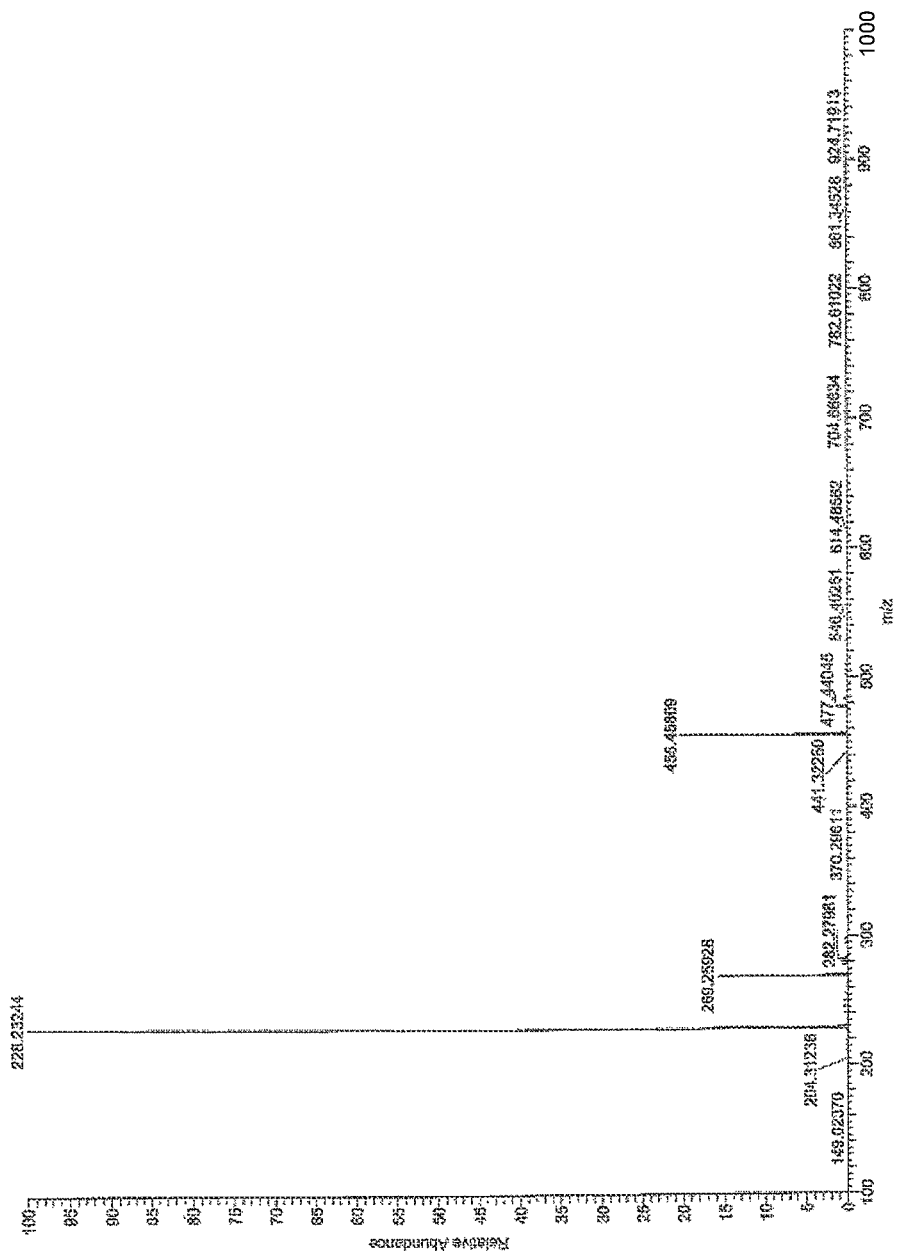
FIG. 25 shows a mass spectrum of peaks corresponding to a retention time 17.77-18.07 from the 24 hour sample.
Figure 26:
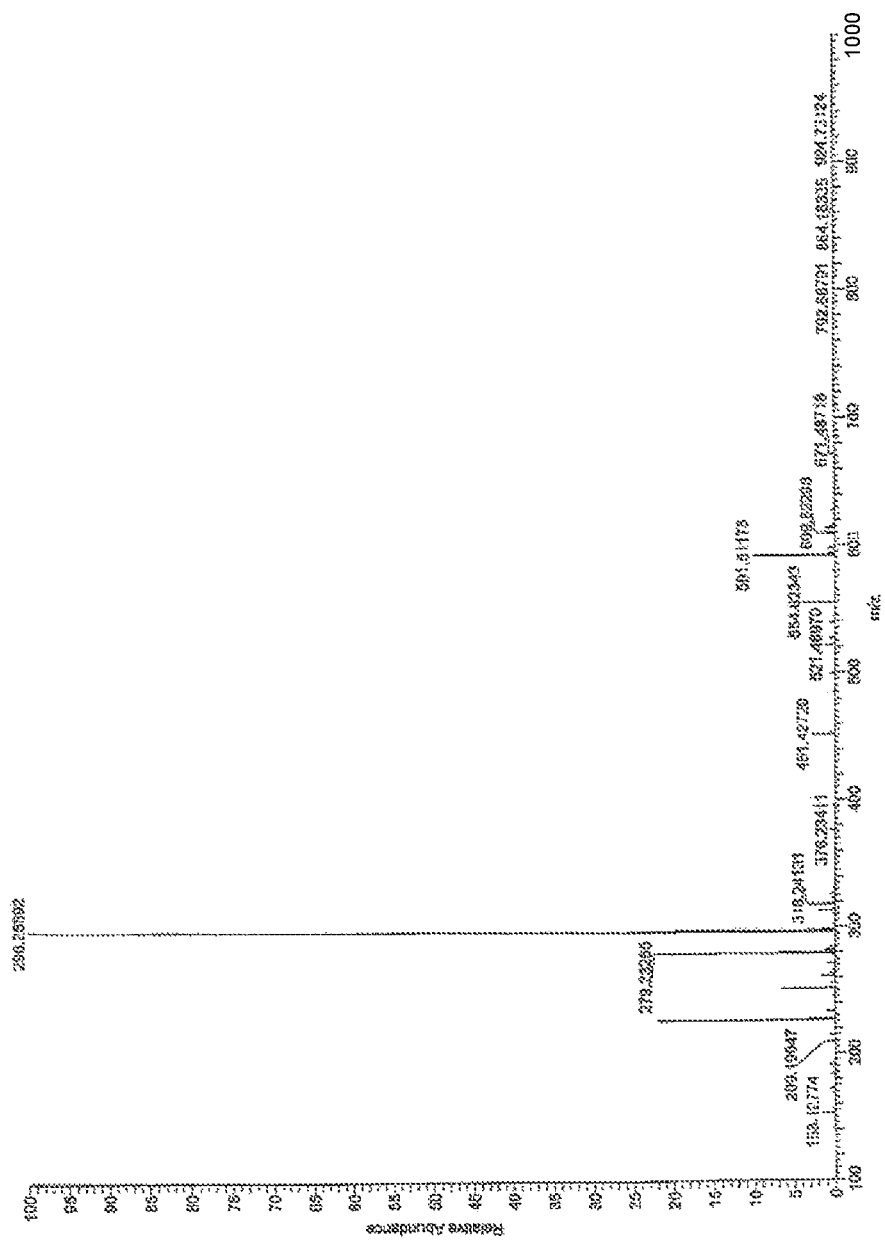
FIG. 26 shows a mass spectrum of peaks corresponding to a retention time 16.01-16.23 from the 24 hour sample.
Figure 27:
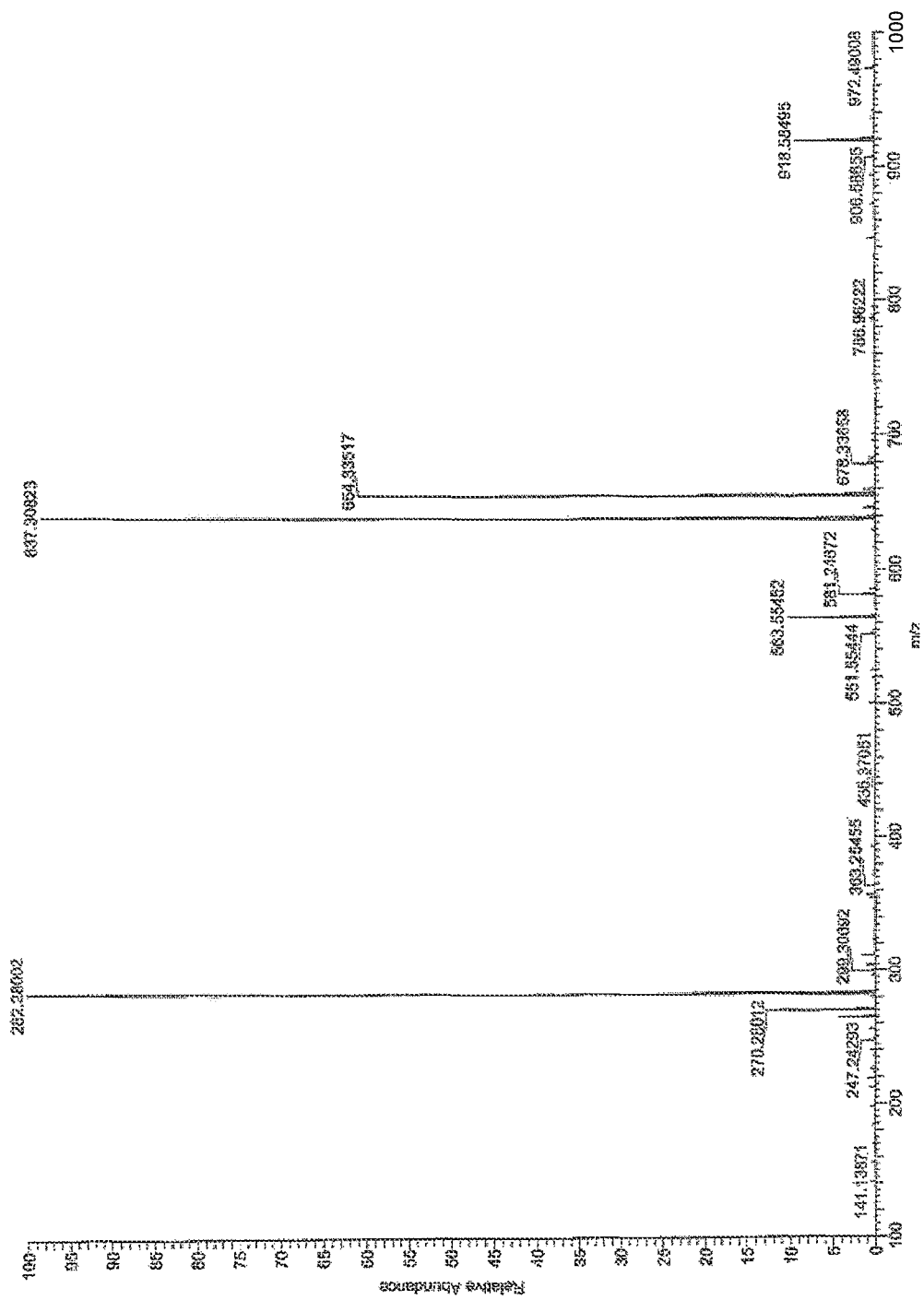
FIG. 27 shows a mass spectrum of peaks corresponding to a retention time 21.37-21.43 from the 24 hour sample.

Samples related to (17-β)-3-Oxoandrost-4-en-17-yl tridecanoate can be analyzed by LC/MS. In one specific example, substantial pure (17-β)-3-Oxoandrost-4-en-17-yl tridecanoate was exposed to elevated temperatures for 24 hours or 48 hours. The samples were dissolved in a solvent after exposure to elevated temperatures. The samples were then prepared for the LC/MS experiments by a 1:10,000 dilution into (20:80 acetonitrile:distilled/deionized water) by first dilution into the acetonitrile and then by bringing the volume up to the final volume by dilution with the distilled/deionized water. FIG. 16 shows the result trace from the column (C18 Atlantis; injection volume).

FIGS. 17-27 show the mass spectra corresponding to peaks from the HPLC trace.

Example 7

Stability of API in Compositions Described Herein

The tables below represents the results from a stability study of the indicated compositions at the indicated times and conditions. The results were obtained from HPLC analysis of the samples.

| Composition (A) | | | |
|---|---|---|---|
| Ingredient Name | Weight Percent of Fill Pharmaceutical Composition (±1%) % w/w | Quantity Fill Material per Hard Gel Capsule (±1%) mg | Quantity Fill Material per Soft Gel Capsule (±1%) mg |
| API | 24 | 183 | 300 |
| Oleic Acid, NF | 41 | 308 | 513 |
| Peppermint Oil, NF | 18 | 136 | 225 |
| Polyoxyl 40 Hydrogenated Castor Oil, NF | 4 | 30 | 50 |
| Ascorbyl Palmitate, NF | 0.2 | 1.5 | 2.5 |
| Glyceryl Palmitostearate (Glyceryl Distearate, NF) | 12 | 90 | 150 |
| Total | 100 | 750 | 1241 |

| Composition (B) | | | |
|---|---|---|---|
| Ingredient Name | Weight Percent of Fill Pharmaceutical Composition (±1%) % w/w | Quantity Fill Material per Hard Gel Capsule (±1%) mg | Quantity Fill Material per Soft Gel Capsule (±1%) mg |
| API | 28 | 183 | 350 |
| Oleic Acid, NF | 55 | 365 | 688 |
| Polyoxyl 40 Hydrogenated Castor Oil, NF | 4 | 26 | 50 |
| Stearic Acid, NF | 4 | 26 | 50 |
| Glyceryl Palmitostearate (Glyceryl Distearate, NF; Precirol ATO 5) | 8 | 52 | 100 |
| Ascorbyl Palmitate, NF | 0.2 | 1.3 | 2.5 |
| Total | 100 | 654 | 1241 |

| Composition (A) RRT | T = 0 Ambient | T = 1 month | | T = 3 months | |
|---|---|---|---|---|---|
| | | 25° C./ 60% RH | 40° C./ 75% RH | 25° C./ 60% RH | 40° C./ 75% RH |
| Assay (API) | 102.7% | 99.7% | 99.2% | 102.7% | 99.4% |
| Testosterone | ND | <0.05% | 0.34% | 0.09% | 1.14% |
| 0.39 | ND | ND | ND | ND | ND |
| 0.46 | ND | ND | 0.07 | 0.06 | 0.09 |
| 0.88 | 0.06 | 0.06 | 0.05 | 0.06 | 0.05 |
| 1.36 | ND | 0.05 | ND | ND | 0.05 |
| 2.52 | NR | NR | ND | ND | 0.3 |
| Total Unspecified | 0.06% | 0.11% | 0.12% | 0.12% | 0.49% |

ND = None Detected at expected retention times above 0.05%
NR = Peaks Not observed or Reported

| | | T = 1 month | | T = 3 months | |
|---|---|---|---|---|---|
| Composition (B) | T = 0 Ambient | 25° C./ 60% RH | 40° C./ 75% RH | 25° C./ 60% RH | 40° C./ 75% RH |
| Assay (API) | 102.7% | 99.7% | 99.2% | 98.8% | 97.4% |
| Known Impurity | | | | | |
| Testosterone | ND | <0.05% | 0.34% | 0.10% | 0.98% |
| Unspecified RC - RRT | | | | | |
| 0.39 | ND | ND | ND | ND | ND |
| 0.46 | ND | ND | 0.07 | ND | ND |
| 0.88 | 0.06 | 0.06 | 0.05 | 0.06 | 0.05 |
| 1.36 | ND | 0.05 | ND | 0.05 | 0.05 |
| 2.43 | NR | NR | NR | NR | 0.07 |
| 2.52 | NR | NR | NR | ND | 0.12 |
| Total Unspecified | 0.06% | 0.11% | 0.12% | 0.10% | 0.27% |

ND = None Detected at expected retention times above 0.05%
NR = Peaks Not observed or Reported RRT stands for relative retention time compared to API when analyzed by HPLC. Exemplary HPLC conditions are a C18 column (5 μm), 150×3.9 mm, 90% methanol:10% deionized water at a flow rate of 1.0 mL/min with the column at 25° C.

Example 8

Release Profile

The compositions, dosage forms described herein containing API can subjected to in vitro dissolution (release) testing using USP type 2 apparatus in about 1000 mL aqueous medium. The composition (e.g., dosage form) is subjected to in vitro dissolution testing using USP type 2 apparatus in about e.g., 1000 mL 8% Triton X100 solution in water at a specific temperature (e.g., 37° C.) at 100 rpm for a specific time (e.g., 1, 2, 3, 4, 5, 10, 15, 30, 45, 60, 75, 90, 120, 180, or 240 minute time point where a sample is withdrawn and analyzed for API content (e.g., via HPLC)).

Example 9

Release Profile Stability

Figure 28:
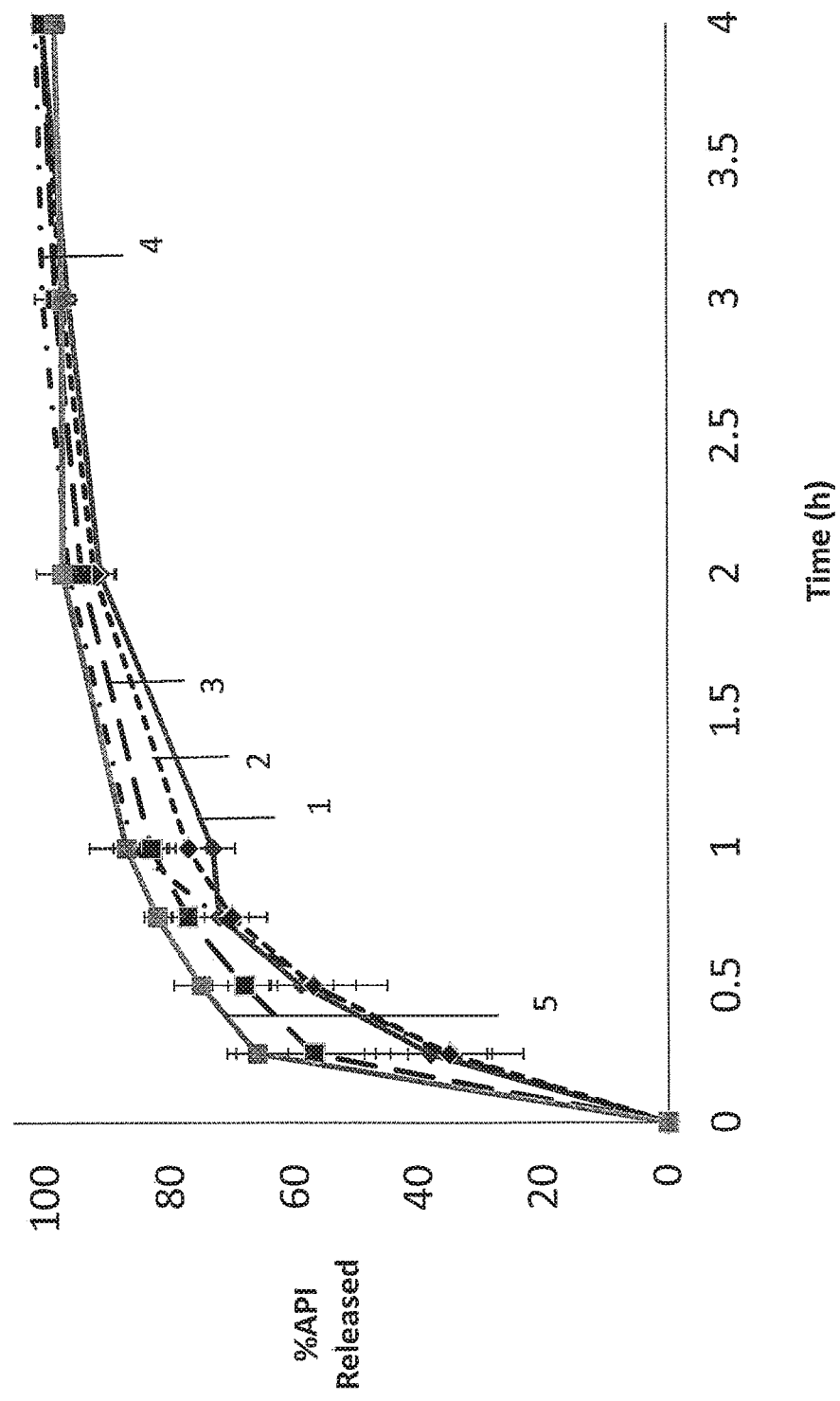
FIG. 28 shows the release profile stability of a pharmaceutical composition having (17-β)-3-Oxoandrost-4-en-17-yl tridecanoate. See Examples 8 and 9.

The compositions, dosage forms described herein containing API can subjected to in vitro dissolution (release) testing using USP type 2 apparatus in about 1000 mL aqueous medium as described in the above example after storage for particular amounts of time under specific conditions. FIG. 28 shows the release profile stability of composition (B) composition (e.g., unit dosage form of composition (B) described herein. The diamonds with solid line labeled 1 represents time point 0; the diamond with dotted line represents 1 month storage at 25° C. and 60% relative humidity (labeled 2); the square with long dashed line represents 1 month storage at 40° C. and 75% relative humidity (labeled 3); the square with dash dot line represents 3 month storage at 25° C. and 60% relative humidity (labeled 4); and the square with lighter solid line represents 3 month storage at 40° C. and 75% relative humidity (labeled 5). The X-axis represents time in hours with measurements made at 15 min, 30 min, 45 min, 1 hour, 2 hours and 4 hours. The Y-axis represents percent API released in 1000 mL 8% Triton X-100 media at 37° C. with a USP Type 2 Apparatus at 100 RPM.

Figure 29:
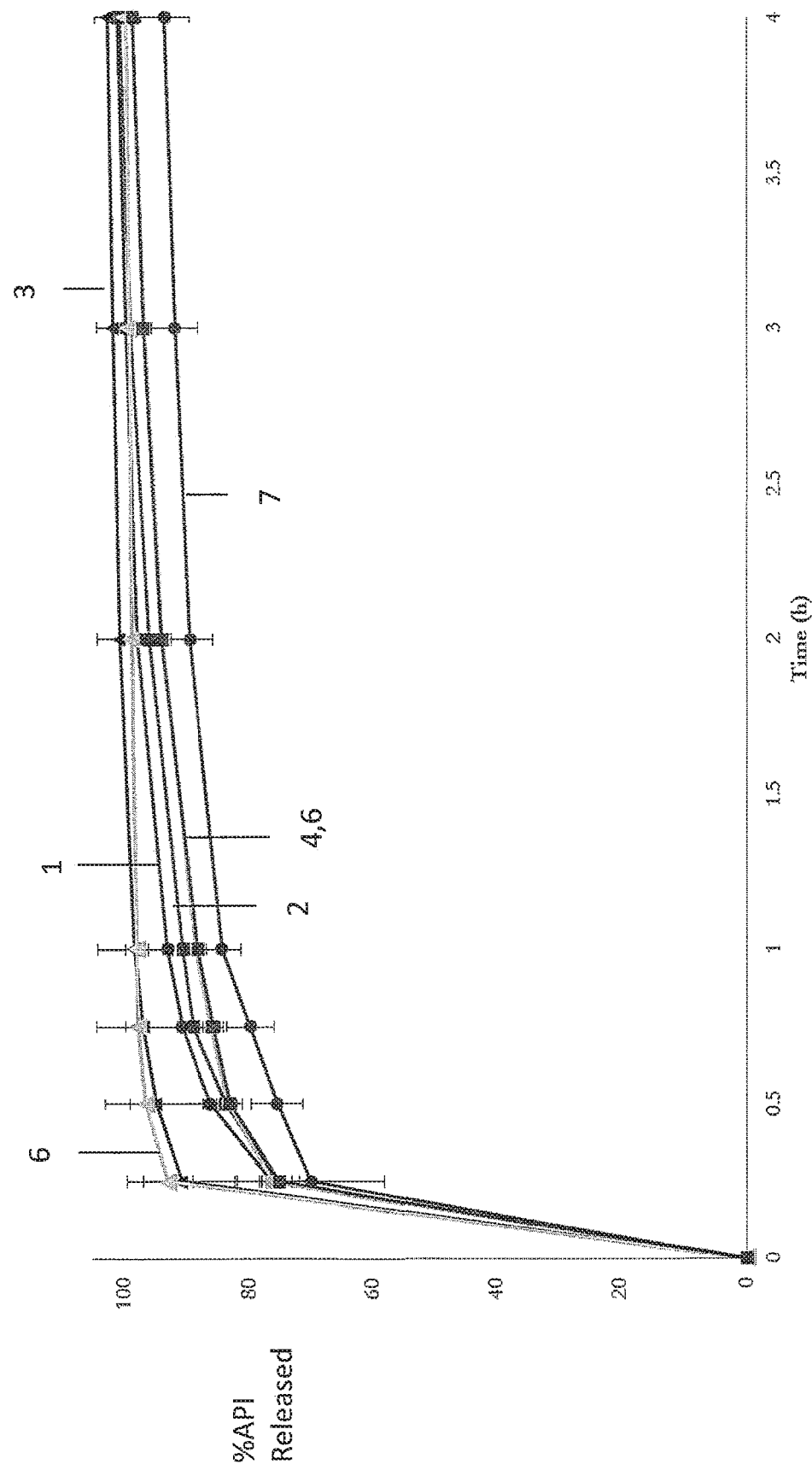
FIG. 29 shows the release profile stability of a pharmaceutical composition having (17-β)-3-Oxoandrost-4-en-17-yl tridecanoate. See Example 8 and 9.

FIG. 29 shows the release profile stability for composition (A) at time 0 (1), 1 month stored at either 25° C. 60% RH (2) or 40° C. 75% RH (3), 2 months stored at either at either 25° C. 60% RH (4) or 40° C. 75% RH (5), and 3 months stored at either at either 25° C. 60% RH (6) or 40° C. 75% RH (7). RH is relative humidity. The X-axis represents time in hours with measurements made at 15 min, 30 min, 45 min, 1 hour, 2 hours and 4 hours. The Y-axis represents percent API released in 1000 mL 8% Triton X-100 media at 37° C. with a USP Type 2 Apparatus at 100 RPM.

Example 10

Methods of Use—Pharmacokinetic Study

Some of the dosage forms of compositions described herein comprising or prepared from substantially pure (17-β)-3-Oxoandrost-4-en-17-yl tridecanoate were administered to human subjects as a single dose of the esters to subjects. Serial blood samples were drawn at predetermined time (e.g., t=0, 12, 24, etc.) and analyzed for testosterone concentration using a validated HPLC-MS/MS analytical method. The $C_{max}$, $C_{avg\ t1-t2}$, $T_{max}$ and $AUC_{t1-t2}$ are calculated for testosterone in the serum of the subjects. Pharmacokinetic and statistical analyses are performed on the data obtained from the subjects. The pharmacokinetic parameters are defined as follows:

$AUC_{t1-t2}$: The area under the serum concentration versus time curve, from time t1 (in hours) to time t2 (in hours) measurable concentration of the administered drug, as calculated by the linear trapezoidal method. For e.g., $AUC_{t0-t24}$ refers to the area under the serum concentration versus time curve, from time 0 (zero) hours to time 24 hours post-administration of dose.

$C_{max}$: The maximum measured serum concentration of the administered drug.

$C_{avg\ t1-t2}$: The average serum concentration of testosterone obtained by dividing the $AUC_{t1-t2}/|t2-t1|$, where in t is time post-administration of dose expressed in hours.

$T_{max}$: The time (in hours) at which the maximum measured plasma concentration of the administered drug is achieved.

Mean: Average value of measured parameter of all individual subjects.

$C_{avg\ t0-t24}$: The average serum concentration of testosterone obtained by dividing the $AUC_{t0-t24}$ value by 24. This represents the average serum testosterone level over a period starting from time 0 (zero) hours to time 24 hours post-administration of dose. It should also be noted that $C_{avg\ t0-t24}$ is also referred to as simply "$C_{avg}$" in this invention.

$C_{avg\ t0-t12}$: The average serum concentration of testosterone obtained by dividing the $AUC_{t0-t24}$ value by 12. This represents the average serum testosterone level over a period starting from time 0 (zero) hours to time 24 hours post-administration of dose.

$C_{avg\ t12-t24}$: The average serum concentration of testosterone obtained by dividing the $AUC_{t12-t24}$ value by 12. This represents the average serum testosterone level over the second half of the 24-hours post-administration of dose period; i.e., from a period starting from time 12 hours to time 24 hours post-administration of dose.

Some of the pharmacokinetic results for the compositions are summarized in the Tables below.

TABLE 1

| Starting Total mg T Equivalent Dose (±dose adjustment in mg T equivalent)* | | % Responders with $C_{ave\ t0-t24}$ (ng/dL) 300-1140 | % Responders with $C_{max}$ (ng/dL) | | |
|---|---|---|---|---|---|
| | | | ≤1500 | 1800-2500 | >2500 |
| (17-β)-3-Oxoandrost-4-en-17-yl tridecanoate | 300 (±50) QD | 100 | 100 | 0-5 | 0-1 |
| | 350 (±100) BID | 100 | 100 | 0-5 | 0-1 |
| | 1000 (±200) QD or BID | 100 | 0 | 20-30 | 60-80 |
| (12-20% EAPI, 55-70% lipophilic additive (e.g., lipophilic surfactant) Hydrophilic additive 12-20% (e.g. Hydrophilic surfactant)) | 100 (±50) QD or BID | 50-65 | 100 | 0-5 | 0-1 |

TABLE 2

| | Composition (weight %) Composition No. | | |
|---|---|---|---|
| Components | 12 | 13 | 14 |
| (17-β)-3-Oxoandrost-4-en-17-yl tridecanoate | 10-30 | 10-30 | 10-30 |
| Lipophilic additive [e.g. surfactant of HLB <10 such as mono- or di- or tri-glyceride of fatty acid or fatty acid] | 55-80 | 55-80 | 55-80 |
| Hydrophilic additive (e.g. Surfactant with HLB >10 such as Cremophor RH40) | 0-20 | 0-20 | 0-20 |
| Adjuvant | q.s. | q.s | q.s. |
| PK parameter | Serum T pharmacokinetic results | | |
| Daily dose as mg T Equivalent | 250-400 | 250-500 | 250-400 |
| % of T-ester not dissolved in lipophilic additive at body temperature | 0 | >12 | >40 |
| % of T-ester not dissolved in lipophilic additive at 20° C. | 0 | >15 | >50 |
| No. of capsules/daily T dose | 4-5 | 3-7 | 1-3 |
| Mean serum T $C_{avg\ t0-t24}$/mg T equivalent [ng/dL/mg] | 1.65 | 1-2-2.2 | 1.86 |

It is also notable that Compositions 12-14 can be formulated as a capsule or tablet dosage form. Further, each of the capsule dosage forms can be formulated to contain from about 50 mg to about 450 mg of the ester (or more or less). For instance, the Compositions 12-14 can be formulated as a capsule or tablet dosage form.

Total daily ester dose administered is 300 to 1500 mg for Compositions 12-14. Specifically, for Compositions 12-14 the total daily (17-β)-3-Oxoandrost-4-en-17-yl dose administered is from about 3000 mg to about 1500. However, it is notable that unlike Composition 12 that has no "not dissolved" ester, Compositions 13 and 14 require fewer dosage units per administration.

Table 2 shows that the higher the fraction of the lipobalanced ester not dissolved or not solubilized, the fewer the number of daily dosage form units (e.g., capsules) that need to be administered to achieve the desirable serum testosterone levels when treating hypogonadism in a male with (17-β)-3-oxoandrost-4-en-17-yl tridecanoate. It should be noted that to provide the total daily dose of about 420 mg-850 mg of the (17-β)-3-Oxoandrost-4-en-17-yl tridecanoate for a hypogonadal subject, no more than four oral dosage form units are required; even more preferred is that no more than two oral dosage form units per day are required for administration.

Compositions 12-14 can be prepared with the lipophilic surfactant and hydrophilic surfactant in amounts such that the ratio of amount (wt %) of lipophilic surfactant to amount (wt %) of hydrophilic surfactant is greater than 2:1. Specifically, the ratio of amount (wt %) of lipophilic surfactant to amount (wt %) of hydrophilic surfactant can be greater than 2.5:1. Further, the ratio of amount (wt %) of lipophilic surfactant to amount (wt %) of hydrophilic surfactant can be greater than 3.5:1. Even further, the ratio of amount (wt %) of lipophilic surfactant to amount (wt %) of hydrophilic surfactant can be greater than 6.5:1.

Compositions 12-14 can be prepared with hydrophilic surfactant present at 20 wt % or more of the total carrier. Compositions 12-14 can be prepared with hydrophilic surfactant present at 5 wt % or less of the total carrier. The lipophilic additives, the hydrophilic additives, and the adjuvant for the representative inventive compositions shown in Table 7 can be similar to those described for compositions in Table 2. The pharmacokinetic (PK) evaluation procedure is given under Example 2. The PK results for the Compositions 13 and 14 or related capsule dosage forms thereof, following oral administration of single dose, two consecutive doses or steady state to a group of subjects, for example, hypogonadal males, along with a meal, are summarized in Table 3A, 3B and 3C.

TABLE 3A

Serum T pharmacokinetics for Compositions 13 and 14 following single administration

| PK parameter | Results |
|---|---|
| Range of mean $C_{max}$/mg of T equivalent dose, [ng/dL/mg] | 1.4-4.5 |
| Range of mean $C_{avg\ t0-t24}$/mg of T equivalent dose, [ng/dL/mg] | 1.2-2.2 |
| Range of the $C_{avg\ t12-t24}$ as % of the $C_{avg\ t0-t24}$ | 35-70 |
| Duration of post-dosing time with serum T at > 300 ng/dL | 12 to 24 hours |

TABLE 3B

Serum T pharmacokinetics for Compositions 13 and 14 following two consecutive dose administration

| PK parameter | Results |
| --- | --- |
| Time of T concentration below 300 ng/dL following two consecutive administrations 24 hours apart (once daily) within 48 hour time period | 2 to 7 hours |
| Time of T concentration below 300 ng/dL following two consecutive administrations about 12 hours apart (twice daily) within 24 hours | 0.5 to 3.5 hours |

TABLE 3C

Steady state serum T pharmacokinetics for Compositions 13 and 14 following at least 7 days continuous administration to a group of at least 12 subjects

| PK parameter | Results |
| --- | --- |
| Time of T concentration below 300 ng/dL following once daily administration | 3.5-6.5 hours |
| % of patients with serum T < 300 ng/dL for more than 7 hours following once daily administration | <50% |
| Time of T concentration below 300 ng/dL following twice daily administration | 0.3 to 3.5 hours |
| % of patients with serum T < 300 ng/dL for more than 7 hours following twice daily administration | <20% |

It is noteworthy that unlike Composition 12, Compositions 13 and 14 are not fully dissolved nor solubilized in the composition or dosage form thereof. Further, Compositions 13 and 14 provide, upon single administration with a meal to a human subject, a serum T mean $C_{avg\ t0-t24}$/mg of T equivalent dose administered in a range between the 1.2 to 2.2 ng/dL/mg. Additionally, Compositions 13 and 14 enable a patient-friendly dosing regimen, for instance via fewer dosage units per administration.

It is understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. A stable pharmaceutical composition comprising (17-β)-3-Oxoandrost-4-en-17-yl tridecanoate and a pharmaceutically acceptable carrier suitable for administration to a human subject in need of (17-β)-hydroxy androst-4-en-3-one, said carrier comprising oleic acid, ascorbyl palmitate, polyoxyl 40 hydrogenated castor oil and glyceryl palmitostearate, wherein when stored for at least 1 month at no less than 25° C. and no less than 60% relative humidity the composition is substantially free of (17-β)-3-Oxoandrost-4-en-17-yl tridecanoate impurities.

2. The pharmaceutical composition of claim 1, wherein the (17-β)-3-Oxoandrost-4-en-17-yl tridecanoate has 10% or less of total impurities.

3. The pharmaceutical composition of claim 2, wherein the (17-β)-3-Oxoandrost-4-en-17-yl tridecanoate has 10% or less of at least one of total known impurities and total unknown impurities.

4. The pharmaceutical composition of claim 2, wherein the (17-β)-3-Oxoandrost-4-en-17-yl tridecanoate has 10% or less of any single known impurity.

5. The pharmaceutical composition of claim 4, wherein the (17-β)-3-Oxoandrost-4-en-17-yl tridecanoate has 10% or less of beta-hydroxy androst-4-en-3-one.

6. The pharmaceutical composition of claim 3, wherein the (17-β)-3-Oxoandrost-4-en-17-yl tridecanoate has 2% or less of any single unknown impurity.

7. The pharmaceutical composition of claim 1, comprising less than 50,000 PPM organic solvent.

8. The pharmaceutical composition of claim 1, wherein the human subject is a male.

9. A stable pharmaceutical composition comprising (17-β)-3-Oxoandrost-4-en-17-yl tridecanoate and a pharmaceutically acceptable carrier suitable for administration to a human subject in need of (17-β)-hydroxy androst-4-en-3-one, said carrier comprising oleic acid, ascorbyl palmitate, polyoxyl 40 hydrogenated castor oil and glyceryl palmitostearate, wherein when stored for at least 1 month at no less than 40° C. and no less than 75% relative humidity the composition is substantially free of (17-β)-3-Oxoandrost-4-en-17-yl tridecanoate impurities.

10. The pharmaceutical composition of claim 9, wherein the (17-β)-3-Oxoandrost-4-en-17-yl tridecanoate has 10% or less of total impurities.

11. The pharmaceutical composition of claim 10, wherein the (17-β)-3-Oxoandrost-4-en-17-yl tridecanoate has 10% or less of at least one of total known impurities and total unknown impurities.

12. The pharmaceutical composition of claim 10, wherein the (17-β)-3-Oxoandrost-4-en-17-yl tridecanoate has 10% or less of any single known impurity.

13. The pharmaceutical composition of claim 12, wherein the (17-β)-3-Oxoandrost-4-en-17-yl tridecanoate has 10% or less of beta-hydroxy androst-4-en-3-one.

14. The pharmaceutical composition of claim 11, wherein the (17-β)-3-Oxoandrost-4-en-17-yl tridecanoate has 2% or less of any single unknown impurity.

15. The pharmaceutical composition of claim 9, comprising less than 50,000 PPM organic solvent.

16. The pharmaceutical composition of claim 9, wherein the human subject is a hypogonadal male.

* * * * *